United States Patent
Hu et al.

(10) Patent No.: US 8,778,972 B2
(45) Date of Patent: *Jul. 15, 2014

(54) 5-PYRIDIN-3-YL-1, 3-DIHYDRO-INDOL-2-ON DERIVATIVES AND THEIR USE AS MODULATORS OF ALDOSTERONE SYNTHASE AND/OR CYP11B1

(75) Inventors: Qi-Ying Hu, Needham, MA (US); Sylvie Chamoin, Saint Louis (FR); Christopher M. Adams, Somerville, MA (US); Chun Zhang, Waltham, MA (US)

(73) Assignee: Novartis AG, Basel (CH)

( * ) Notice: Subject to any disclaimer, the term of this patent is extended or adjusted under 35 U.S.C. 154(b) by 180 days.

This patent is subject to a terminal disclaimer.

(21) Appl. No.: 13/319,786

(22) PCT Filed: May 12, 2010

(86) PCT No.: PCT/EP2010/056569
§ 371 (c)(1),
(2), (4) Date: Nov. 10, 2011

(87) PCT Pub. No.: WO2010/130794
PCT Pub. Date: Nov. 18, 2010

(65) Prior Publication Data
US 2012/0071512 A1 Mar. 22, 2012

Related U.S. Application Data

(60) Provisional application No. 61/178,684, filed on May 15, 2009, provisional application No. 61/327,218, filed on Apr. 23, 2010.

(51) Int. Cl.
*A61K 31/4439* (2006.01)
*C07D 401/04* (2006.01)

(52) U.S. Cl.
USPC ....................................... 514/339; 546/277.7

(58) Field of Classification Search
USPC ....................................... 546/277.7; 514/339
See application file for complete search history.

(56) References Cited

U.S. PATENT DOCUMENTS

| 6,831,175 B2 | 12/2004 | Li et al. |
| 2003/0187026 A1 | 10/2003 | Li et al. |
| 2003/0199511 A1 | 10/2003 | Li et al. |
| 2006/0247441 A1 | 11/2006 | Wilk |
| 2007/0027327 A1 | 2/2007 | Wu et al. |
| 2009/0048322 A1 | 2/2009 | Chow et al. |

FOREIGN PATENT DOCUMENTS

| EP | 1719761 A1 | 11/2006 |
| WO | 00/64872 A1 | 11/2000 |
| WO | 03/051366 A2 | 6/2003 |
| WO | 03/086467 A1 | 10/2003 |
| WO | 2005/080334 A1 | 9/2005 |
| WO | 2006/066133 A2 | 6/2006 |
| WO | 2007/024949 A2 | 3/2007 |
| WO | 2009/023179 A2 | 2/2009 |
| WO | 2009/135651 A1 | 11/2009 |
| WO | 2009/156462 A2 | 12/2009 |
| WO | 2010/130773 A2 | 11/2010 |
| WO | 2010/130794 A1 | 11/2010 |
| WO | 2010/130796 A1 | 11/2010 |

OTHER PUBLICATIONS

Lucas et al., "In Vivo Active Aldosterone Synthase Inhibitors with Improved Selectivity: Lead Optimization Providing a Series of Pyridine Substituted 3, 4-Dihydro-1H-quinolin-2-one Derivatives," Journal of Medicinal Chemistry 51 (24):8077-8087 (Dec. 25, 2008).
Adams et al.; "Mapping the Kinase Domain of Janus Kinase 3"; Bioorganic & Medicinal Chemistry Letters; 13:3105-3110 (2003).
Ellis et al.; "A Versatile Synthesis of Unsymmetrical 3,3'-Bioxindoles: Stereoselective Mukaiyama Aldol Reactions of 2-Siloxyindoles with Isatins"; J. Org. Chem.; 73:9151-9154 (2008).
McAllister et al.; "A Fluorous-Phase Pummerer Cyclative-Capture Strategy for the Synthesis of Nitrogen Heterocycles"; Angew. Chem. Int. Ed.—Communications; 44:452-455 (2005).
McAllister et al.; "A Fluorous, Pummerer Cyclative-Capture Strategy for the Synthesis of N-Heterocycles"; Chem. Eur. J.; 13:1032-1046 (2007).
Zhu et al.; "Discovery and SAR of oxindole—pyridine-based protein kinase B/Akt inhibitors for treating cancers"; Bioorganic & Medicinal Chemistry Letters; 16:3424-3429 (2006).

*Primary Examiner* — Patricia L Morris
(74) *Attorney, Agent, or Firm* — Sophie Binet Cross

(57) ABSTRACT

The present invention provides a compound of formula I;

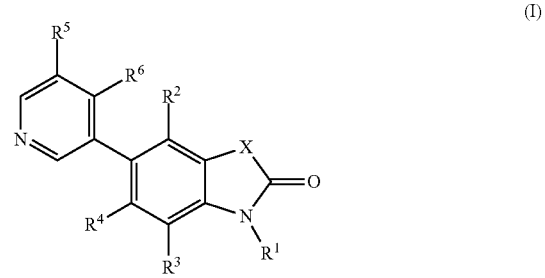

a method for manufacturing the compounds of the invention, and its therapeutic uses. The present invention further provides a combination of pharmacologically active agents and a pharmaceutical composition.

9 Claims, No Drawings

5-PYRIDIN-3-YL-1, 3-DIHYDRO-INDOL-2-ON DERIVATIVES AND THEIR USE AS MODULATORS OF ALDOSTERONE SYNTHASE AND/OR CYP11B1

This application is a U.S. National Phase filing of International Serial No. PCT/EP2010/056569 filed May 12, 2010, and claims priority to U.S. provisional application Ser. No. 61/327,218 filed Apr. 23, 2010 and Ser. No. 61/178,684 filed May 15, 2009, the contents of which are incorporated herein by reference in their entirety.

BACKGROUND OF THE INVENTION

The mineralocorticoid hormone aldosterone is produced by the adrenal gland and acts on the distal tubules and collecting ducts of the kidney to increase reabsorption of ions and water in the kidney. Aldosterone causes conservation of sodium, secretion of potassium, increased water retention, and increased blood pressure.

Aldosterone has been implicated in the pathogenesis of cardiovascular diseases such as hypertension and heart failure. In clinical trials, treatment with the nonselective mineralocorticoid receptor antagonist (MRA) spironolactone or the selective MRA eplerenone significantly reduced morbidity and mortality among patients with heart failure or myocardial infarction already taking an angiotensin-converting enzyme inhibitor or a β-blocker. However, significant side effects such as gynecomastia and impotence were observed in male patients receiving spironolactone while hyperkalemia was seen in patients taking either drug.

SUMMARY OF THE INVENTION

The invention pertains to the compounds, methods for using them, and uses thereof as described herein. Examples of compounds of the invention include the compounds according to any one of Formulae I-VIII, or pharmaceutically acceptable salt thereof, and the compounds of the examples.

The invention therefore provides a compound of the Formula I:

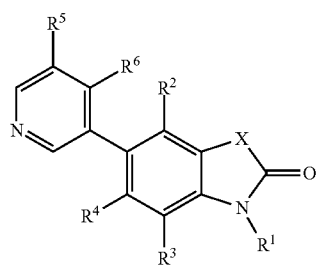

(I)

or a pharmaceutically acceptable salt thereof, wherein:

X is $CH_2$, O, S or $-NR^1$;

each $R^1$ are independently $C_{1-7}$alkyl or $C_{3-8}$cycloalkyl;

each of $R^2$ and $R^6$ are independently hydrogen, halogen, cyano, $C_{1-7}$alkyl, hydroxy-$C_{1-7}$alkyl, $-OR^7$, $C_{3-8}$cycloakyl, halo-$C_{1-7}$alkyl or $-CH_2-NR^8-SO_2-R^{10}$;

$R^3$ and $R^4$ are independently hydrogen, halogen or cyano;

$R^5$ is hydrogen, $C_{1-7}$alkyl, halogen, cyano, hydroxy, hydroxy-$C_{1-7}$alkyl, hydroxy-$C_{3-8}$cycloalkylalkyl, $C_{1-7}$alkoxy-$C_{3-8}$alkyl, $-OR^7$, $C_{6-10}$aryl, heteroaryl, heterocyclyl, $C_{3-8}$cycloalkyl, halo-$C_{1-7}$alkyl, $-NR^8R^9$, $-CH_2-NR^8-C(O)NR^8R^9$, $-CH_2-NR^8-SO_2-R^{10}$, $-C(O)-R^{10}$, $-SO_2R^{10}$, $-C(O)-NR^8R^9$, $-SO_2-NR^8R^9$, $-NR^8C(O)-R^{10}$, $-CH_2CN$ or $-NR^8-SO_2-R^{10}$;

$R^7$ is $C_{1-7}$alkyl, $C_{3-8}$cycloalkyl-$C_{1-7}$alkyl, heterocyclyl-$C_{1-7}$alkyl, $C_{8-10}$aryl-$C_{1-7}$alkyl, heteroaryl-$C_{1-7}$alkyl or $-C(O)-R^{10}$; in which $C_{6-10}$aryl, heteroaryl, $C_{1-7}$alkyl, heterocyclyl and $C_{3-8}$cycloalkyl are optionally substituted with $C_{1-7}$alkoxy, halo, halo-$C_{3-8}$alkoxy, $C_{1-7}$alkyl, OH or halo-$C_{1-7}$alkyl;

each of $R^8$, $R^9$ are independently hydrogen, $C_{1-7}$alkyl, halo-$C_{1-7}$alkyl, $C_{6-10}$aryl-$C_{1-7}$alkyl or heterocyclyl; or $R^8$ and $R^9$ can form together with the nitrogen atom to which they are attached a 5- or 6-membered ring heterocyclyl, wherein said heterocyclyl optionally contain an additional heteroatom selected from N, O or S and is optionally substituted with $C_{1-7}$alkyl; and $R^{10}$ is hydrogen, $C_{1-7}$alkyl, halo $C_{1-7}$alkyl, $C_{6-10}$aryl-$C_{1-6}$alkyl, $-NR^8R^9$, or heterocyclyl;

wherein each heteroaryl is a mono- or bicyclic aromatic moiety comprising 5-10 ring atoms selected from carbon atoms and 1 to 5 heteroatoms, and each heterocyclyl is a mono- or bicyclic saturated or partially saturated but non-aromatic moiety comprising 4-10 ring ring atoms selected from carbon atoms and 1 to 5 heteroatoms; and each heteroatoms being O, N or S, and with the proviso that when $R^5$ is halogen or hydrogen than at least one of $R^2$ and $R^6$ is other than H.

In another embodiment, the invention pertains, at least in part, to a method for treating a disorder or disease mediated by aldosterone synthase and/or 11-beta hydroxylase (CYP11B1) in a subject by administering to the subject a therapeutically effective amount of a compound according to anyone of Formulae or a pharmaceutically acceptable salt thereof, such that the disorder or disease mediated by aldosterone synthase and/or CYP11B1 in the subject is treated.

In yet another embodiment, the invention pertains, at least in part, to a method for treating a subject for hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess, comprising administering to the subject a therapeutically effective amount of a compound according to anyone of Formulae I-VIII, or a pharmaceutically acceptable salt thereof, such that the subject is treated.

In yet another embodiment, the invention pertains, at least in part, to pharmaceutical compositions, comprising an effective amount of a compound according to anyone of Formulae I-VIII, or a pharmaceutically acceptable salt thereof, wherein said effective amount is effective to treat a disorder or disease mediated by aldosterone synthase and/or CYP11B1.

In still another embodiment, the invention pertains, at least in part, to combinations including pharmaceutical combinations of one or more therapeutically active agents.

In another embodiment, the invention pertains, at least in part, to a method for inhibiting aldosterone synthase and/or CYP11B1 in a subject by administering to the subject a therapeutically effective amount of a compound according to anyone of Formulae I-VIII, or a pharmaceutically acceptable salt thereof such that aldosterone synthase and/or CYP11B1 is inhibited.

An alternative approach to ameliorate the deleterious effects of aldosterone, provided by the present invention, is the suppression of aldosterone production by aldosterone synthase inhibitors. Aldosterone synthase is an enzyme responsible for the final steps of the biosynthesis of aldosterone from deoxycorticosterone, via conversion of corticosterone to form 18-OH-corticosterone, which is then converted to aldosterone.

Accordingly, the invention pertains, at least in part, to compounds, pharmaceutical compositions containing the compound and methods of use thereof. The present invention also relates to novel compounds which may be used, for example, as modulators and/or inhibitors of aldosterone synthase and/or CYP11B1.

The compounds of the present invention may, for example, be used to treat various diseases or disorders hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, fibrinoid necrosis of coronary arteries, Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess.

DETAILED DESCRIPTION OF THE INVENTION

Compounds of the Invention

References hereinafter to compounds of Formula I apply equally to compounds of Formulae II-VIII.

References hereinafter to embodiments of the invention apply equally to compounds of Formula I and compounds of Formulae II-VIII, insofar as the embodiments are present.

Various embodiments of the invention are described herein. It will be recognized that features specified in each embodiment may be combined with other specified features to provide further embodiments.

In one embodiment the invention provides a compound of the Formula I

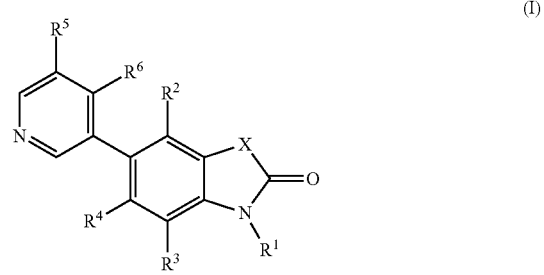

a pharmaceutically acceptable salt thereof, wherein:

X is $CH_2$, O, S or $-NR^1$;

each $R^1$ are independently $C_{1-7}$alkyl or $C_{3-8}$cycloalkyl;

each of $R^2$ and $R^6$ are independently hydrogen, halogen, cyano, hydroxy-$C_{1-7}$alkyl, $-OR^7$, $C_{3-8}$cycloalkyl, halo-$C_{1-7}$alkyl or $-CH_2-NR^8-SO_2-R^{10}$;

$R^3$ and $R^4$ are independently hydrogen, halogen or cyano;

$R^5$ is hydrogen, $C_{1-7}$allyl, halogen, cyano, hydroxy, hydroxy-$C_{1-7}$alkyl, hydroxy-$C_{3-8}$cycloalkylalkyl, $-OR^7$, $C_{6-10}$aryl, heteroaryl, heterocyclyl, $C_{3-8}$cycloalkyl, halo-$C_{1-7}$alkyl, $-NR^8R^9$, $-CH_2-NR^8-C(O)NR^8R^9$, $-CH_2-NR^8-SO_2-R^{10}$, $-C(O)-R^{10}$, $-SO_2R^{10}$, $-C(O)-NR^8R^9$, $-SO_2-NR^8R^9$, $-NR^8C(O)-R^{10}$, $-CH_2CN$ or $-NR^9-SO_2-R^{10}$;

$R^7$ is $C_{1-7}$alkyl, $C_{3-8}$cycloalkyl-$C_{1-7}$alkyl, heterocyclyl-$C_{1-7}$alkyl, $C_{6-10}$aryl-$C_{1-7}$alkyl, heteroaryl-$C_{1-7}$alkyl or $-C(O)-R^{10}$; in which $C_{1-7}$aryl, heteroaryl, $C_7$alkyl, heterocyclyl and $C_{3-4}$cycloalkyl are optionally substituted with $C_{1-7}$alkoxy, halo, halo-$C_{3-8}$alkoxy, OH or halo-$C_{1-7}$alkyl;

each of $R^8$, $R^9$ are independently hydrogen, $C_{1-7}$alkyl, halo-$C_{1-7}$alkyl, $C_{6-10}$aryl-$C_{1-7}$alkyl or heterocyclyl; or $R^8$ and $R^9$ can form together with the nitrogen atom to which they are attached a 5- or 6-membered ring heterocyclyl, wherein said heterocyclyl optionally contain an additional heteroatom selected from N, O or S and is optionally substituted with $C_{1-7}$alkyl; and $R^{10}$ is hydrogen, $C_{1-7}$alkyl, halo-$C_{1-7}$alkyl, $C_{6-10}$aryl-$C_{1-7}$alkyl, $-NR^8R^9$, or heterocyclyl;

wherein each heteroaryl is a mono- or bicyclic aromatic moiety comprising 5-10 ring atoms selected from carbon atoms and 1 to 5 heteroatoms, and each heterocyclyl is a mono- or bicyclic saturated or partially saturated but non-aromatic moiety comprising 4-10 ring ring atoms selected from carbon atoms and 1 to 5 heteroatoms; and each heteroatoms being O, N or S; and with the proviso that when $R^5$ is halogen or hydrogen than at least one of $R^2$ and $R^6$ is other than H.

In one embodiment, the invention pertains to compounds of Formula

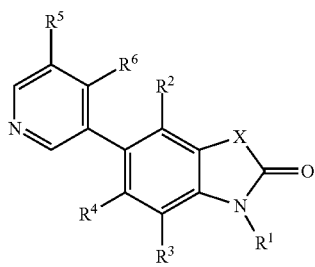

(I)

or a pharmaceutically acceptable salt thereof, wherein:
X is $CH_2$, O, S or $-NR^1$;
each $R^1$ are independently $C_{1-7}$alkyl or $C_{3-8}$cycloalkyl;
each of $R^2$ and $R^6$ are independently hydrogen, halogen, cyano, hydroxy-$C_{1-7}$alkyl, $C_{3-8}$cycloalkyl, halo-$C_{1-7}$alkyl or $-CH_2-NR^8-SO_2-R^{10}$;
$R^3$ and $R^4$ are independently hydrogen, halogen or cyano;
$R^5$ is hydrogen, $C_{1-7}$alkyl, halogen, cyano, hydroxy, hydroxy-$C_{1-7}$alkyl, hydroxy-$C_{3-8}$cycloalkylalkyl, $C_{1-7}$alkoxy-$C_{3-8}$alkyl, $C_{6-10}$aryl, heteroaryl, heterocyclyl, $C_{3-8}$cycloalkyl, halo-$C_{1-7}$alkyl, $-NR^8R^9$, $-CH_2-NR^8-C(O)NR^9$, $-CH_2-NR^8-SO_2-R^{10}$, $-C(O)-R^{10}$, $-SO_2R^{10}$, $-C(O)-NR^8R^9$, $-SO_2-NR^8R^9$, $-NR^8C(O)-R^{10}-CH_2C$ or $-NR^8-SO_2-R^{10}$;
$R^7$ is $C_{1-7}$alkyl, $C_{3-8}$cycloalkyl-$C_{1-7}$alkyl, heterocyclyl-$C_{1-7}$alkyl, heteroaryl-$C_{1-7}$alkyl or $-C(O)-R^{10}$; in which $C_{6-10}$aryl, heteroaryl, $C_{1-7}$alkyl, heterocyclyl and $C_{3-8}$cycloalkyl are optionally substituted with $C_{1-7}$alkoxy, halo, halo-$C_{3-8}$alkoxy, $C_{1-7}$alkyl, OH or halo-$C_{1-7}$alkyl;
each of $R^8$, $R^9$ are independently hydrogen, $C_{1-7}$alkyl, halo-$C_{1-7}$alkyl, $C_{6-10}$aryl-$C_{1-7}$alkyl or heterocyclyl; or $R^6$ and $R^9$ can form together with the nitrogen atom to which they are attached a 5- or 6-membered ring heterocyclyl, wherein said heterocyclyl optionally contain an additional heteroatom selected from N, O or S and is optionally substituted with $C_{1-7}$alkyl; and
$R^{10}$ is hydrogen, $C_{1-7}$alkyl, halo-$C_{1-7}$alkyl, $C_{6-10}$aryl-$C_{1-4}$alkyl, $-NR^8R^9$, or heterocyclyl;
wherein each heteroaryl is a mono- or bicyclic aromatic moiety comprising 5-10 ring atoms selected from carbon atoms and 1 to 5 heteroatoms, and
each heterocyclyl is a mono- or bicyclic saturated or partially saturated but non-aromatic moiety comprising 4-10 ring ring atoms selected from carbon atoms and 1 to 5 heteroatoms; and each heteroatoms being O, N or S; and with the proviso that when $R^5$ is halogen or hydrogen than $R^2$ is other than H.

Certain compounds of Formula I include compounds of Formula II:

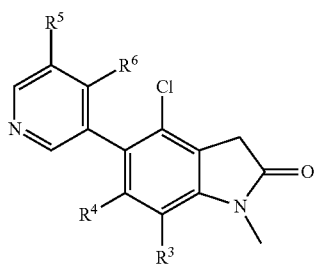

(II)

or a pharmaceutically acceptable salt thereof, wherein $R^3$, $R^4$, $R^5$ and $R^6$ have the definitions of Formula I, supra.

Certain compounds of Formula I include compounds of Formula III:

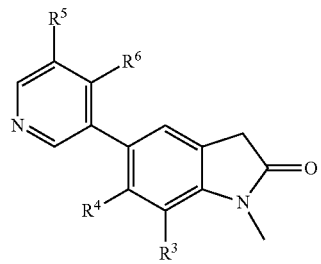

(III)

or a pharmaceutically acceptable salt thereof, wherein $R^3$, $R^4$, $R^5$ and $R^6$ have the definitions of Formula I, supra.

Certain compounds of Formula I include compounds of Formula IV:

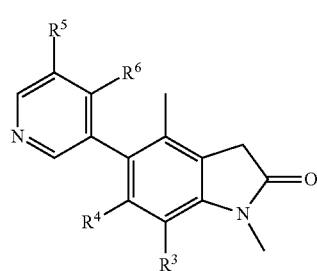

(IV)

or a pharmaceutically acceptable salt thereof, wherein $R^3$, $R^4$, $R^5$ and $R^6$ have the definitions of Formula I, supra.

Certain compounds of Formula I include compounds of Formula V:

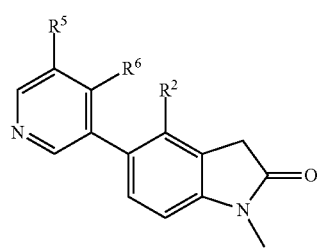

(V)

or a pharmaceutically acceptable salt thereof, wherein
$R^2$ is hydrogen, halogen, $-OR^7$, or $C_{1-7}$alkyl;
$R^5$ is hydrogen, $C_{1-7}$alkyl, halogen, $C_{6-10}$aryl, $C_{3-8}$cycloalkyl, heteroaryl, hydroxy, hydroxy-$C_{1-7}$alkyl, $C_{1-7}$alkoxy, halo-$C_{1-7}$alkyl, benzyloxy, $-SO_2NR^8R^9$, $-CH_2-NR^8-SO_2-R^{10}$ or $-NR^8R^9$;
$R^6$ is hydrogen or $C_{1-7}$alkyl;
$R^7$ is $C_{1-7}$alkyl, $C_{2-8}$cycloalkyl-$C_{1-7}$alkyl heterocyclyl-$C_{1-7}$alkyl, $C_{6-10}$aryl-$C_{1-7}$alkyl, heteroaryl-$C_{1-7}$alkyl or $-C(O)-R^{10}$; and
each of $R^8$, $R^9$ and $R^{10}$ are independently $C_{1-7}$alkyl or hydrogen.

Certain compounds of Formula I include compounds of Formula VI

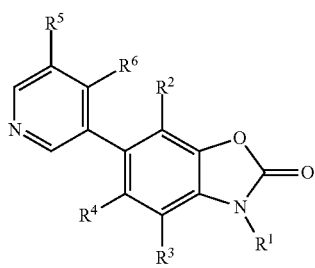

(VI)

or a pharmaceutically acceptable salt thereof, wherein $R^2$, $R^3$, $R^4$, $R^5$ and $R^6$ have the definitions of Formula I, supra.

Certain compounds of Formula I include compounds of Formula VII

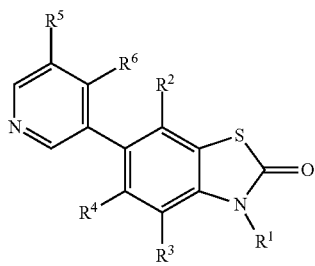

(VII)

or a pharmaceutically acceptable salt thereof, wherein $R^2$, $R^3$, $R^4$, $R^5$ and $R^6$ have the definitions of Formula I, supra.

Certain compounds of Formula I include compounds of Formula VIII

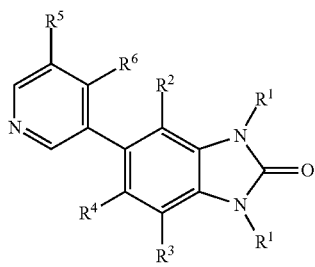

(VIII)

or a pharmaceutically acceptable salt thereof, wherein $R^3$, $R^4$, $R^5$ and $R^6$ have the definitions of Formula I, supra.

One embodiment include compounds according to any one of Formulae I, VI, VII and VIII or of any classes and subclasses described herein, or a pharmaceutically acceptable salt thereof, in which $R^1$ is $C_{1-4}$ alkyl (e.g., methyl, ethyl, propyl, isopropyl and butyl). In a particular aspect of this embodiment $R^1$ is methyl. In yet another embodiment, $R^1$ is $C_{3-8}$cycloalkyl (e.g. cyclopropyl, cyclobutyl, cyclopentyl, and cyclohexyl).

Another embodiment include compounds according to any one of Formulae I, V, VI, VII and VIII or of any classes and subclasses described herein, or a pharmaceutically acceptable salt thereof, in which $R^2$ is hydrogen, halogen (e.g., fluorine, chlorine, bromine, iodine), cyano, $C_{1-7}$alkyl (e.g., methyl ethyl, propyl, isopropyl and butyl), $C_{3-8}$cycloalkyl (e.g., cyclopropyl, cyclobutyl, cyclopentyl, and cyclohexyl), or $-OR^7$. In a particular aspect of this embodiment, $R^2$ is hydrogen, halogen, $-OR^7$ or $C_{1-4}$alkyl. In yet another particular aspect of this embodiment, $R^2$ is hydrogen, chloro, methyl, methoxy or $-O$-benzyl. In a further aspect of this embodiment, $R^2$ is hydrogen, chloro, methyl, methoxy or $-O$-benzyl and $R^1$ is methyl.

In another embodiment, $R^7$ is $C_{1-4}$alkyl or arylalkyl.

In yet another embodiment, $R^7$ is methyl, ethyl, isopropyl, $-C(O)$-isopropyl, or $R^7$ is one of the following:

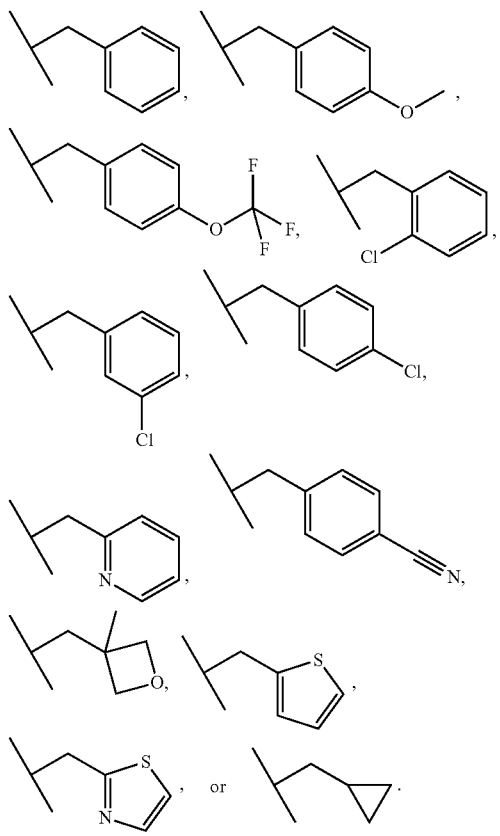

Another embodiment include compounds according to any one of Formulae I, V, VI, VII and VIII or of any classes and subclasses described herein, or a pharmaceutically acceptable salt thereof, in which $R^2$ is selected from halo, $OR^7$ and cycloalkyl. In a further aspect of this embodiment, $R^2$ is halo (e.g. chloro), cycloalkyl (e.g. cyclopropyl), benzyloxy, $C_{1-4}$alkoxy (e.g. methoxy, ethoxy) or heteroaryl-$CH_2O-$. In yet a further aspect of this embodiment, $R^5$ is halo or H.

In one embodiment, this invention pertains to compounds according to anyone of Formulae I, II, III, IV, VI, VII and VIII or of any classes and subclasses described herein, or a pharmaceutically acceptable salt thereof, in which $R^3$ and/or $R^4$ is hydrogen. In another embodiment, this invention pertains to compounds according to anyone of Formulae I, II, III, IV, V, VI, VII and VIII or of any classes and subclasses described herein, or a pharmaceutically acceptable salt thereof, in which $R^3$ and $R^4$ are independently halogen (e.g., fluorine, chlorine, bromine, iodine) or cyano.

Another embodiment include compounds of Formula I (or any of the other Formulae, any other classes and/or subclasses of this invention), or a pharmaceutically acceptable salt thereof, wherein $R^5$ is $C_{1-7}$alkyl, cyano, hydroxy, hydroxy-$C_{1-7}$alkyl, hydroxy-$C_{3-8}$cycloalkylalkyl, $C_{1-7}$alkoxy-$C_{3-8}$alkyl, $-OR^7$, $C_{6-10}$aryl, heteroaryl, heterocyclyl, $C_{3-8}$cycloalkyl, halo-$C_{1-7}$alkyl, —$NR^8R^9$, —$CH_2$—$NR^8$—$C(O)$ $NR^8R^9$, —$CH_2$—$NR^8$—$SO_2$—$R^{10}$, —$C(O)$—$R^{10}$, —$SO_2R^{10}$, —$C(O)$—$NR^8R^9$, —$SO_2$—$NR^8R^9$, —$NR^8C$ $(O)$—$R^{10}$, —$CH_2CN$, and —$NR^8$—$SO_2$—$R^{10}$.

Another embodiment include compounds of Formula I (or any other formulae, any other classes and/or subclasses of this invention) or a pharmaceutically acceptable salt thereof, in which $R^5$ is hydrogen, $C_{1-7}$alkyl (e.g., methyl, ethyl, or isopropyl), halogen (e.g., chlorine, fluorine, or bromine), $C_{6-10}$aryl (e.g. phenyl), heteroaryl (e.g. pyridine), $C_{3-8}$cycloalkyl (e.g. cyclopropyl), cyano, hydroxy, hydroxy$C_{1-7}$ alkyl (e.g. —$CH_2OH$, —$CH(OH)$isopropyl, —$CH(OH)$ $CH_2CH_3$, —$CH(OH)CH_3$), $C_{1-7}$alkoxy (e.g., methoxy, ethoxy), benzyloxy, $C_{1-7}$alkoxy-$C_{1-7}$alkyl or —$NR^8R^9$, where $R^8$ and $R^9$ are each ethyl or $R^8$ is H and $R^9$ is ethyl. In a further aspect of this embodiment, the invention pertains to compounds of Formula I (or any other formulae, any other classes and/or subclasses of this invention) or a pharmaceutically acceptable salt thereof, in which $R^5$ is $C_{1-7}$alkyl (e.g., methyl, ethyl, or isopropyl), $C_{6-10}$aryl (e.g. phenyl), heteroaryl (e.g. pyridine), $C_{3-8}$cycloalkyl (e.g. cyclopropyl), cyano, hydroxy, hydroxy$C_{1-7}$alkyl (e.g. —$CH_2OH$, —$CH$ $(OH)$isopropyl, —$CH(OH)CH_2CH_3$, —$CH(OH)CH$), $C_{1-7}$alkoxy (e.g., methoxy, ethoxy), benzyloxy, $C_{1-7}$alkoxy-$C_{1-7}$alkyl or —$NR^8R^9$, where $R^8$ and $R^9$ are each ethyl or $R^8$ is H and $R^9$ is ethyl.

In yet another embodiment, the invention pertains to compounds according to anyone of Formulae I to VIII, or a pharmaceutically acceptable salt thereof, wherein $R^5$ is $C_{1-7}$alkyl (e.g., methyl, ethyl, isopropyl, or pentyl); $C_{1-7}$ alkyl substituted with hydroxy (i.e. hydroxyalkyl); $C_{1-7}$alkyl substituted with $C_{1-7}$alkoxy (i.e. alkoxyalkyl); $C_{1-7}$alkyl substituted with halogen (i.e. haloalkyl) or $C_{1-7}$alkyl substituted with cyano (e.g. —$CH_2CN$). Representative examples of this embodiment are compounds of Formula I (or any other formulae, any other classes and/or subclasses of this invention), or a pharmaceutically acceptable salt thereof, in which $R^5$ is:

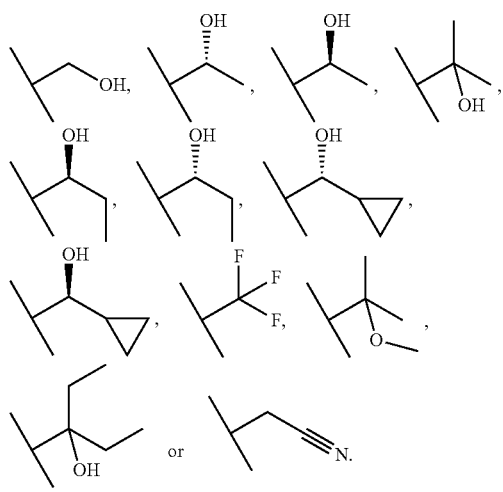

In yet another embodiment, $R^5$ is —$CH_2$—$NR^8$—$SO_2$— $R^{10}$ or —$CH_2$—$NR^8C(O)$—$NR^8R^9$. Representative examples of this embodiment are compounds of Formula I (or any other formulae, any other classes and/or subclasses of this invention), or a pharmaceutically acceptable salt thereof, in which $R^5$ is:

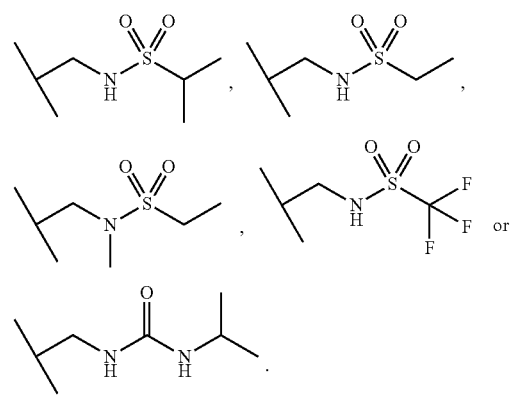

In another embodiment, $R^5$ is $C_{6-10}$aryl, heteroaryl or heterocyclyl. Representative examples of this embodiment include compounds of Formula I (or any other formulae, any other classes and/or subclasses of this invention), or a pharmaceutically acceptable salt thereof, in which $R^5$ is:

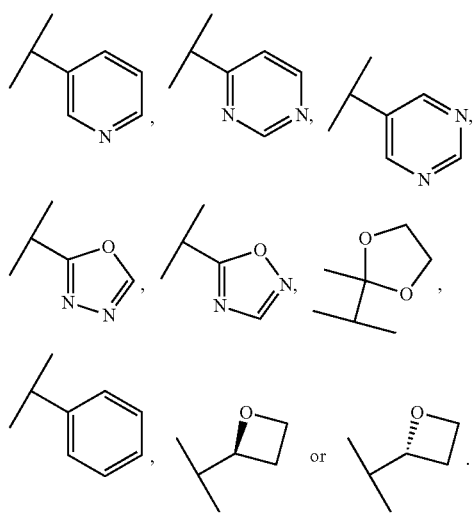

In another embodiment, $R^5$ is $C_{3-8}$cycloalkyl (e.g., cyclopropyl, cyclobutyl, cyclopentyl, and cyclohexyl) or $C_{3-8}$cycloalklyl substituted with hydroxy (hydroxycycloalkyl). Representative example of hydroxycycloalkyl is

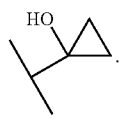

In another embodiment, $R^5$ is —$NR^8R^9$, —$C(O)$—$R^{10}$, —$SO_2R^{10}$, —$C(O)$—$NR^8R^9$, —$SO_2$—$NR^8R^9$, —$NR^8C$ $(O)$—$R^{10}$ or —$NR^8$—$SO_2$—$R^{10}$. Representative examples of this embodiment include compounds of Formula I (or any other formulae, any other classes and/or subclasses of this invention), or a pharmaceutically acceptable salt thereof, in which $R^5$ is:

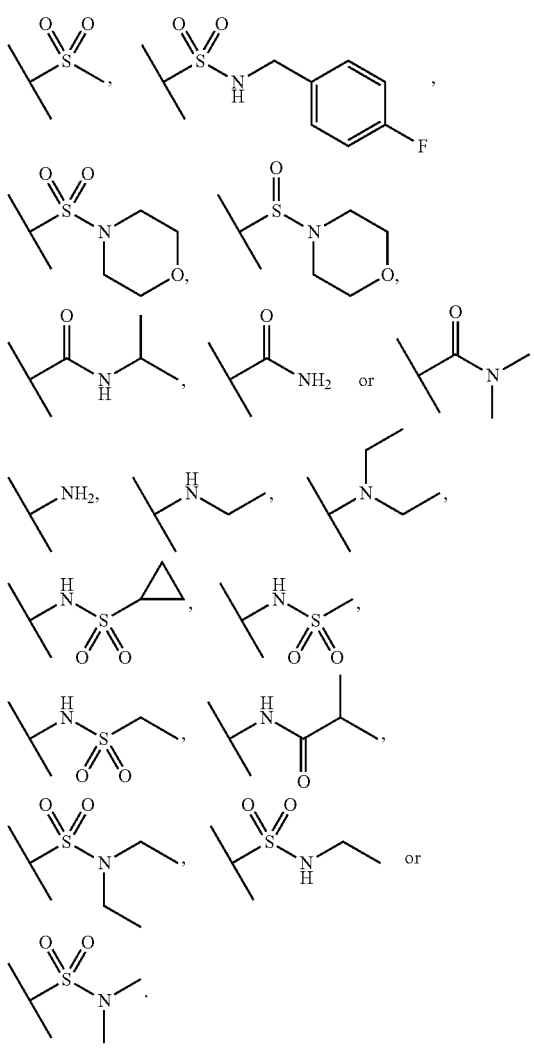

In one embodiment, the invention pertains to compounds according to anyone of Formulae I to VIII, or a pharmaceutically acceptable salt thereof, wherein $R^6$ is hydrogen, halogen (e.g., fluorine, chlorine, bromine, iodine), cyano, $C_{1-7}$alkyl (e.g., methyl ethyl, propyl, isopropyl and butyl) or $C_{1-7}$alkyl substituted with hydroxy (hydroxyalkyl); $C_{1-7}$alkyl substituted with $C_{1-7}$alkoxy (alkoxyalkyl); $C_{1-7}$ alkyl substituted with halogen (haloalkyl), or —$NR^8SO_2$—$R^{10}$, for example:

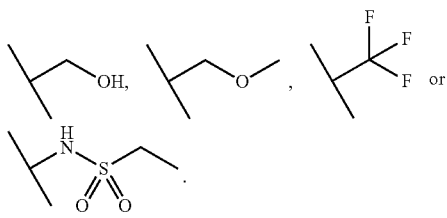

In another embodiment, the invention pertains to compounds according to anyone of Formulae I to VIII, or a pharmaceutically acceptable salt thereof, wherein $R^6$ is hydrogen, or $C_{1-7}$alkyl (e.g., methyl).

In still another embodiment, examples of $R^6$ and $R^9$ include hydrogen and $C_{1-7}$alkyl (e.g., ethyl), resulting in, for example, —$NR^9R^9$ including —$NH_2$, —$N(ethyl)_2$, $NH(ethyl)$.

In still another embodiment, $R^8$ and $R^9$ form together with the atoms to which they are attached an optionally substituted heterocyclyl. In a representative example, $R^8$ and $R^9$ form a piperidine, N-methylpiperidine or morpholine.

In yet another embodiment, examples of $R^{10}$ include heterocyclyl (e.g., morpholino), $C_{1-7}$alkyl (e.g., methyl, ethyl, or isopropyl), halo-$C_{1-7}$alkyl (e.g. $CF_3$), and optionally substituted amino (e.g., —$NH_2$, —$NHCH(CH_3)_2$, —$N(methyl)_2$).

In yet another embodiment, examples of —$SO_2$—$NR^8R^9$ include —$SO_2$—$N(methyl)_2$, —$SO_2$—$NH(ethyl)$, and —$SO_2$—$NH(CH_2$-fluoro-phenyl).

In yet another embodiment, examples of —$C(O)$—$NR^8R^9$ include —$C(O)$—$NH_2$, —$C(O)$—$NH(isopropyl)$, —$C(O)$—$N(methyl)_2$.

In yet another embodiment, examples of —$NR^8$—$SO_2$—$R^{10}$ include —$N(methyl)$-$SO_2$-ethyl and —$NH$—$SO_2$-methyl.

In another embodiment, examples of —$NR^8C(O)$—$R^{10}$ include —$NH$—$C(O)$-isopropyl.

In another embodiment the $R^1$ to $R^{10}$ groups are those defined by the $R^1$-$R^{10}$ groups, respectively, in Examples 1 to 52 in the Examples section below.

In another embodiment individual compounds according to the invention are those listed in Examples 1 to 52 in the Examples section below, or a pharmaceutically acceptable salt thereof.

DEFINITION

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms. Representative examples of alkyl include methyl, ethyl, n-propyl, isopropyl, n-butyl, sec-butyl, iso-butyl, tert-butyl, n-pentyl, isopentyl, neopentyl, n-hexyl, methylhexyl, 2,2-dimethylpentyl, 2,3-dimethylpentyl, n-heptyl. The term "$C_{1-7}$alkyl" refers to a hydrocarbon having one to seven carbon atoms. Moreover, the term alkenyl includes both "unsubstituted alkyls" and "substituted alkyls".

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-7}$alkyl" refers to a hydrocarbon having one to seven carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons. The term alkoxy include substituted alkoxy. Examples of substituted alkoxy groups include halogenated alkoxy groups. Examples of halogen substituted alkoxy groups are fluoromethoxy, difluoromethoxy, trifluoromethoxy, chloromethoxy, dichloromethoxy, and trichloromethoxy. The term "$C_{1-7}$alkoxy" refers to $C_{1-7}$alkyl-O—, wherein $C_{1-7}$alkyl is defined above. Moreover, the term alkoxy includes both "unsubstituted alkoxy" and "substituted alkoxy".

The term alkoxyalkyl refers to an alkyl group, as defined above, in which the alkyl group is substituted with alkoxy. The term also includes substituted alkoxyalkyl moiety.

The term "alkenyl" refers to a branched or unbranched hydrocarbon having at least one carbon-carbon double bond. The term "$C_{2-7}$alkenyl" refers to a hydrocarbon having two to seven carbon atoms and comprising at least one carbon-carbon double bond. Representative examples of alkenyl are vinyl, prop-1-enyl, allyl, butenyl, isopropenyl or isobutenyl. Moreover, the term alkenyl includes both "unsubstituted alkenyls" and "substituted alkenyls".

The term "alkenyoxy" refer to alkenyl-O— wherein alkenyl has the definition above.

The term "alkynyl" refers to a branched or unbranched hydrocarbon having at least one carbon-carbon triple bond. The term "$C_{2-7}$-alkynyl" refers to a hydrocarbon having two to seven carbon atoms and comprising at least one carbon-carbon triple bond. Representative examples of alkynyl are ethynyl, prop-1-ynyl (propargyl), butynyl, isopropynyl or isobutynyl. Moreover, the term alkynyl includes both "unsubstituted alkynyls" and "substituted alkynyls".

As used herein, the term "cycloalkyl" refers to saturated or partially unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-8}$ cycloakyl" refers to a cyclic hydrocarbon groups having 3 to 8 carbon atoms.

The term "cycloalkylalkyl" refers to an alkyl as defined above substituted with a cycloakyl as defined above.

The alkyl, alkenyl, alkynyl, alkoxy and cycloalkyl groups may be optionally substituted with one or more substituents Representative examples of substitutents for alkyl, alkenyl, alkynyl, alkoxy and cycloalkyl moities are oxo, =S, halogen, hydroxy, cyano, nitro, alkyl, alkenyl, akynyl, alkoxy, alkenyloxy, alkynyloxy, halogen, alkylcarbonyl, alkylcarbonyloxy, arylcarbonyl, arylcarbonyloxy, alkoxycarbonyloxy, aryloxycarbonyloxy, carboxylate, alkylcarbonyl, alkylaminocarbonyl, dialkylaminocarbonyl, arylalkyl, heteroarylalkyl, heterocyclylalkyl, aminocarbonyl, alkenylaminocarbonyl, alkoxycarbonyl, alkylcarbonyl, dialkylaminocarbonyl, arylcarbonyl, arylalkylcarbonyl, alkenylcarbonyl, alkoxycarbonyl, alkylcarbonylamino, alkylcarbonylalkylamino, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, aminosulfonyl, alkylsulfonyl, arylsulfonyl, sulfhydryl, alkylthio, arylthio, thiocarboxylate, sulfates, alkylsulfinyl, sulfamoyl, sulfonamido, heterocyclyl, or an aromatic or heteroaromatic moiety, wherein each of the afore-mentioned hydrocarbon groups may be optionally substituted with one or more halogen, hydroxy or $C_{1-7}$alkoxy groups.

The term "aryl" refers to monocyclic or bicyclic aromatic hydrocarbon groups having 6-20 carbon atoms in the ring portion. Preferably, the aryl is a ($C_{6-10}$aryl). The term aryl also refers to a group in which an aromatic ring is fused to one or more cycloalkyl rings, where the point of attachment is on the aromatic ring or on the fused cycloalkyl ring. Representative examples of aryl are phenyl, naphthyl, anthracyl, phenanthryl or tetrahydronaphthyl. The term "$C_{6-10}$ aryl" refers to an aromatic hydrocarbon groups having 6 to 10 carbon atoms in the ring portion. Moreover, the term aryl includes both "unsubstituted aryl" and "substituted aryl".

The term "arylalkyl" is an alkyl substituted with aryl. Representative examples of arylalkyl are benzyl or Phenyl-CH$_2$CH$_2$—. The term also includes substituted arylalkyl moiety.

The term "Heteroaryl" includes monocyclic or bicyclic heteroaryl, containing from 5-10 ring members selected from carbon atoms and 1 to 5 heteroatoms, and each heteroatoms is selected from O, N or S. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4- or 5-pyrimidin-2-yl, pyrimidin-4-yl, pyrimidin-5-yl. The term "heteroaryl" also refers to a group in which a heteroaromatic ring is fused to one or more aryl, cycloaliphatic, or heterocyclyl rings, where the radical or point of attachment is on the heteroaromatic ring or on the fused aryl, cycloaliphatic or heterocyclyl rings. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenosazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]berizazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

The term "heteroarylakyl" refers to alkyl substituted with heteroaryl. The term also includes substituted heteroarylalkyl moiety.

The aromatic ring of an "aryl" or "heteroaryl" group can be substituted at one or more ring positions with such substituents as described above, as for example, halogen; hydroxy, cyano, nitro, alkyl, alkenyl; akynyl, alkoxy, alkenyloxy, alkynyloxy, halogen, alkylcarbonyl, alkylcarbonyloxy, arylcarbonyl, arylcarbonyloxy, alkoxycarbonyloxy, aryloxycarbonyloxy, carboxylate, alkylcarbonyl, alkylaminoacarbonyl, dialkylaminocarbonyl, arylalkyl, heteroarylalkyl, heterocyclylalkyl, aminocarbonyl, all alkoxycarbonyl, alkylcarbonyl, dialkylaminocarbonyl, arylcarbonyl, arylalkylcarbonyl, alkenylcarbonyl, alkoxycarbonyl, alkylcarbonylamino, alkylcarbonylalkylamino, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, aminosulfonyl, alkylsulfonyl, arylsulfonyl, sulfhydryl, alkylthio, arylthio, thiocarboxylate, sulfates, alkylsulfinyl, sulfamoyl, sulfonamido, heterocyclyl, or an aromatic or heteroaromatic moiety, wherein each of the afore-mentioned hydrocarbon groups may be optionally substituted with one or more halogen, hydroxy or $C_{1-7}$alkoxy groups.

As used herein, the term "heterocyclyl" or "heterocyclo" refers to a saturated or unsaturated non-aromatic ring (partially unsaturated) or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. For bicyclic and tricyclic heterocyclyl ring system, a aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "heterocyclyl" includes heterocyclic groups as defined herein substituted with 1, 2 or 3 substituents such as alkyl, hydroxy (or protected hydroxy), halo, oxo (e.g., =O), amino, alkylamino or dialkylamino, alkoxy, cycloalkyl, carboxyl, heterocyclooxy, wherein heterocyclooxy denotes a heterocyclic group bonded through an oxygen bridge, alkyl-O—C(O)—, mercapto, nitro, cyano, sulfamoyl or sulfonamide, aryl, alkyl-C(O)—O—, aryl-C(O)—O—, aryl-S—, aryloxy, alkyl-S—, formyl (e.g., HC(O)—), carbamoyl, arylalkyl-, and aryl substituted with alkyl, cycloalkyl, alkoxy, hydroxy, amino, alkyl-C(O)—NH—, alkylamino, dialkylamino or halogen.

The term "heterocyclylalkyl" is an alkyl substituted with heterocyclyl. The term include substituted heterocyclylalkyl moiety.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfonyl, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy. The term also includes substituted aroyl moieties. The term "substituted aroyl" includes aroyl groups where one or more of the hydrogen atoms are replaced by for example, halogen, hydroxy, cyano, nitro, alkyl, alkenyl, akynyl, alkoxy, alkenyloxy, alkynyloxy, halogen, alkylcarbonyl, alkylcarbonyloxy, arylcarbonyl, arylcarbonyloxy, alkoxycarbonyloxy, aryloxycarbonyloxy, carboxylate, alkylcarbonyl, alkylaminoacarbonyl, dialkylaminocarbonyl, arylalkyl, heteroarylalkyl, heterocyclylalkyl, aminocarbonyl, alkenylaminocarbonyl, alkoxycarbonyl, alkylcarbonyl, dialkylaminocarbonyl, arylcarbonyl, arylalkylcarbonyl, alkenylcarbonyl, alkoxycarbonyl, alkylcarbonylamino, alkylcarbonylalkylamino, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, aminosulfonyl, alkylsulfonyl, arylsulfonyl, sulfhydryl, alkylthio, arylthio, thiocarboxylate, sulfates, alkylsulfinyl, sulfamoyl, sulfonamido, heterocyclyl, or an aromatic or heteroaromatic moiety, wherein each of the afore-mentioned hydrocarbon groups may be optionally substituted with one or more halogen, hydroxy or $C_{1-7}$alkoxy groups.

The terms "alkoxyalkyl," include alkyl groups, as described above, in which the alkyl group is substituted with an alkoxy as defined above. The term includes substituted alkoxyalkyl moiety.

The term "hydroxyalkyl" refers to alkyl groups, as described above, in which the alkyl group is substituted with a hydroxy. The term includes substituted hydroxyalkyl moiety.

The term "hydroxycycloalkyl" refers to a cycloalkyl, as described above, in which the cycloalkyl is substituted with hydroxy. The term includes substituted hydroxycycloalkyl moiety.

The term "hydroxycycloalkylalkyl" refers to a cycloalkylalkyl, as defined above, in which the cycloalkylakyl is substituted with hydroxy. The term includes substituted hydroxycycloalkylalkyl moiety.

The term "carbamoyl" includes H₂NC(O)—, alkyl-NHC(O)—, (alkyl)₂NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)—. The term includes substituted carbamoyl moieties.

The term "sulfonyl" includes R—SO₂—, wherein R is hydrogen, alkyl, aryl, heteroaryl, aryl-alkyl, heteroaryl-alkyl, alkoxy, aryloxy, cycloalkyl, or heterocyclyl.

The term "sulfonamido" includes alkyl-S(O)₂—NH—, aryl-S(O)₂—NH—, aryl-alkyl-S(O)₂—NH—, heteroaryl-S(O)₂—NH—, heteroaryl-alkyl-S(O)₂—NH—, alkyl-S(O)₂—N(alkyl)-, aryl-S(O)₂N(alkyl)-, aryl-alkyl-S(O)₂—N(alkyl)-, heteroaryl-S(O)₂—N(alkyl)-, heteroaryl-alkyl-S(O)₂—N(alkyl)-. The term includes substituted carbamoyl moieties.

The term "sulfamoyl" includes H₂NS(O)₂—, alkyl-NHS(O)₂—, (alkyl)₂NS(O)₂—, aryl-NHS(O)₂—, alkyl(aryl)-NS(O)₂—, (aryl)₂NS(O)₂—, heteroaryl-NHS(O)₂—, (aryl-alkyl)-NHS(O)₂—, (heteroaryl-alkyl)-NHS(O)₂—. The term includes substituted sulfamoyl moieties.

The term "aryloxy" includes an —O-aryl, wherein aryl is defined herein. The term includes substituted aryloxy moieties.

The term "heteroaryloxy" includes an —O-heteroaryl moiety, wherein heteroaryl is defined herein. The term includes substituted heteroaryloxy moieties.

The term heterocyclyloxy includes an —O-heterocyclyl, wherein heterocyclyl is defined herein. The term includes substituted heterocyclyloxy moieties.

The term "amine" or "amino" includes compounds where a nitrogen atom is covalently bonded to at least one carbon or heteroatom. The term "amine" or "amino" also includes —NH₂ and also includes substituted moieties. The term includes "alkyl amino" which comprises groups and compounds wherein the nitrogen is bound to at least one additional alkyl group. The term includes "dialkyl amino" groups wherein the nitrogen atom is bound to at least two additional independently selected alkyl groups. The term includes "arylamino" and "diarylamino" groups wherein the nitrogen is bound to at least one or two independently selected aryl groups, respectively.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkenylcarbonylamino," and "arylcarbonylamino" are included in term "amide." The term "amide," "amido" or "aminocarbonyl" also includes substituted moieties.

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom. The term also includes substituted moieties.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group. The term also includes substituted moieties.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above. The term also includes substituted moieties.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group. The term also includes substituted moieties.

The term "hydroxy" or "hydroxyl" includes groups with an —OH.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, hydroxy, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxy, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen and sulfur.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium 0 line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1$H, $^2$H or ID, $^3$H); any carbon represented by "C" in any of the formulae herein is intended to represent all isotopic forms of carbon (e.g. $^{11}$C, $^{13}$C, $^{14}$C); any nitrogen represented by "N" is intended to represent all isotopic forms of nitrogen (e.g. $^{14}$N, $^{15}$N). Other examples of isotopes that are included in the invention include isotopes of oxygen, sulfur, phosphorous, fluorine, iodine and chlorine, such as $^{18}$F $^{31}$P, $^{32}$P, $^{35}$S, $^{36}$Cl, $^{125}$I. The invention includes various isotopically labeled compounds as defined herein, for example those into which radioactive isotopes, such as $^3$H, $^{13}$C, and $^{14}$C are present. In one embodiment, the atoms in the formulae herein occur in their natural abundance. In another embodiment, one or more hydrogen atom may be enriched in $^2$H; or/and one or more carbon atom may be enriched in $^{11}$C, $^{13}$C or $^{11}$C; or/and one or more nitrogen may be enriched in $^{14}$N. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound according to any one of the formulae I to VIII. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (76% deuterium incorporation), at least 6500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Isotopically-enriched compounds according to any one of formulae I to VIII can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula with the co-crystal former under crystallization conditions and isolating co-crystals thereby formed. Suitable co-crystal formers include those described in WO 2004/078163. Hence the invention further provides co-crystals comprising a compound of formula I.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by aldosterone synthase and/or CYP11B1, or (ii) associated with aldosterone synthase and/or CYP11B1 activity, or (iii) characterized by abnormal activity of aldosterone synthase and/or CYP11B1; or (2) reduce or inhibit the activity of aldosterone synthase and/or CYP11B1; or (3) reduce or inhibit the expression of aldosterone synthase and/or CYP11B1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of aldosterone synthase and/or CYP11B1; or at least partially reducing or inhibiting the expression of aldosterone synthase and/or CYP11B1.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Aspects

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methylcyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed, 1952, Methods of Organic Synthesis, Thieme, Volume 21).

The compounds of the invention can be synthesized using the methods described in the following schemes, examples, and by using art recognized techniques. All compounds described herein are included in the invention as compounds. Compounds of the invention may be synthesized according to at least one of the methods described in schemes 1-6.

Scheme 1:

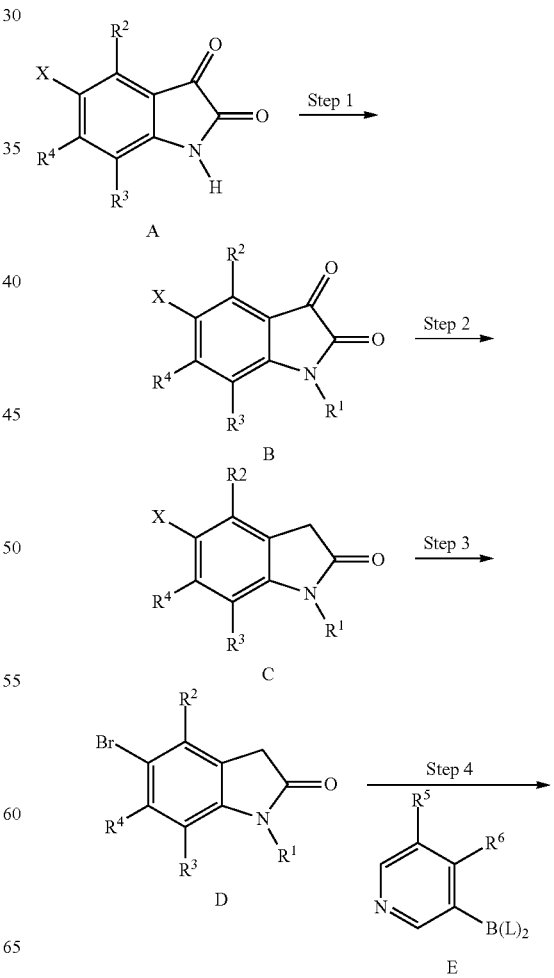

-continued

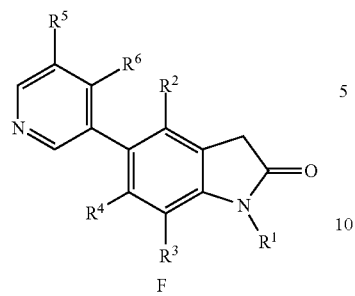

F

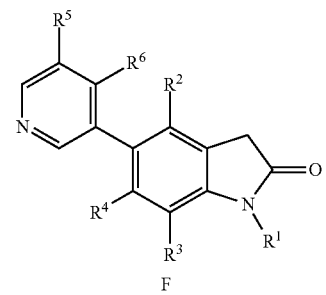

F

Scheme 1 describes the synthesis of compounds according to Formula I, II, III, IV or V, wherein the variables R¹ to R⁶ are as defined in Formula I, supra.

In step one isatins of type A, where X is equal to either bromine, iodine, or hydrogen, can undergo alkylation via treatment with a non-nucleophilic base, preferably potassium carbonate, in the presence of an alkyl halide, for example, iodomethane, at elevated temperatures, preferably 60° C., to afford compounds of type B. Compounds of type B can undergo reduction to oxindoles of type C upon treatment with hydrazine hydrate at elevated temperatures, preferably 130° C. When X is equal to bromine or iodine, step 3 can be omitted. However, when X is equal to hydrogen Step 3 permits halogenation to provide compounds of type a Step three can be accomplished via treatment with aqueous bromine in the presence of potassium bromide at elevated temperatures, preferably at 70° C. Compounds of type D can undergo Suzuki-type palladium-catalyzed coupling with pyridines, such as E, which are substituted at the three position with a boronic acid or ester (e.g. L is OH or O-alkyl), to furnish compounds of type F Scheme 2 illustrates an alternative approach to compounds of type F, wherein variables R¹ to R⁶ are as previously defined in Formula I, supra. In Step 1 bromides of type D prepared as described in Scheme 1, can undergo a Miyaura-type borylation to furnish boronates of type G. Compounds of type C can undergo Suzuki-type palladium catalyzed coupling with pyridines, such as H, which are substituted at the three position with a bromine or iodine, to provide compounds of type F.

Scheme 3:

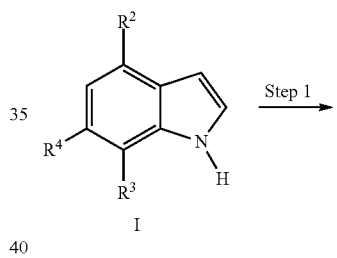

I

Scheme 2:

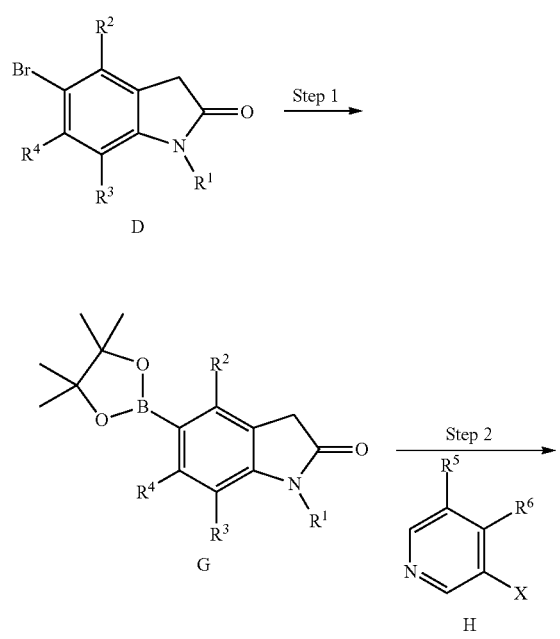

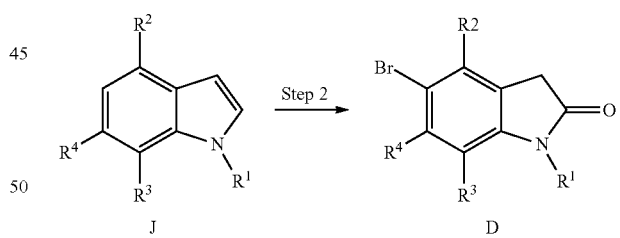

Alternatively, oxindoles of type D, wherein variable R¹ to R⁴ are as previously defined in Formula I supra, can be prepared from indoles of type I. In Step 1 the indole nitrogen can undergo alkylation upon treatment with a strong base, preferably sodium hydride, followed by reaction with an alkyl halide, for example, iodomethane. The resulting indoles of type J can then undergo a two step sequence of bromination with concomitant hydrolysis, followed by reduction, preferably employing zinc dust in acetic acid to furnish oxindoles of type D.

Scheme 4:

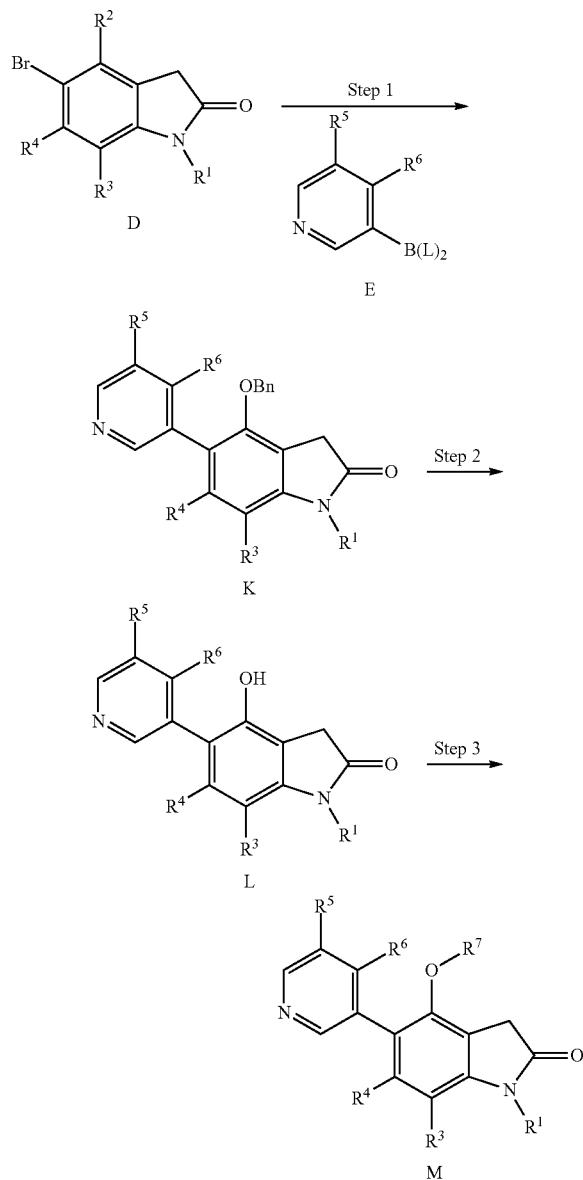

Scheme 5:

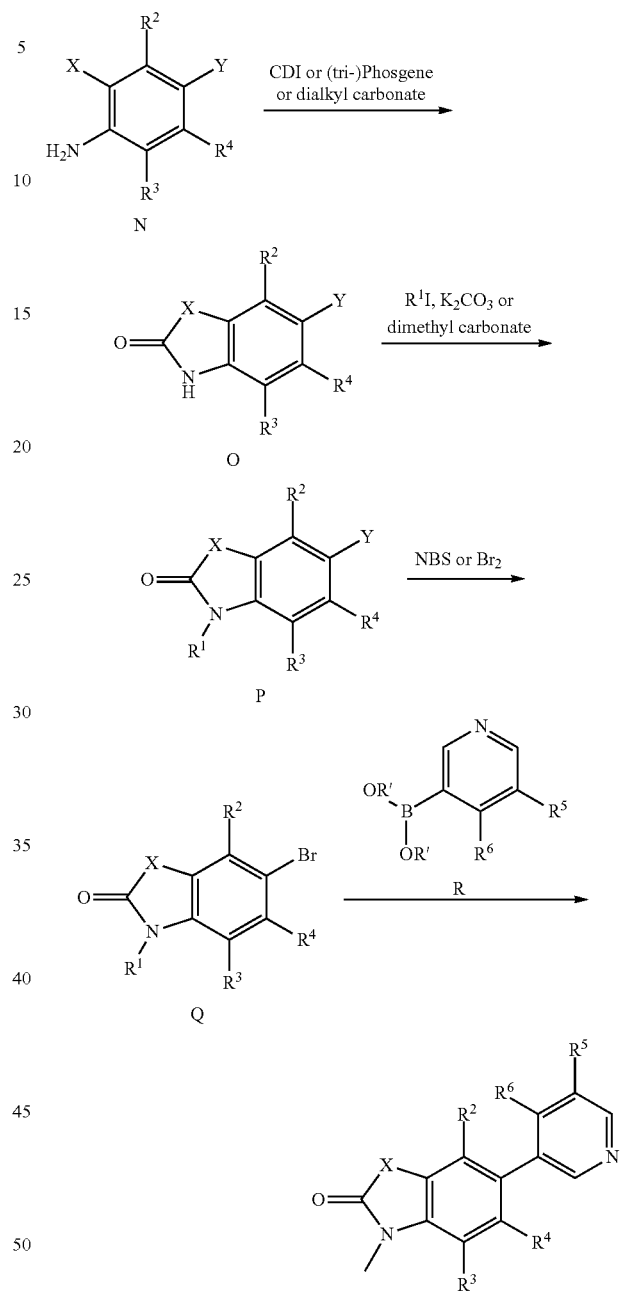

Scheme 4 illustrates an approach to ethers of type M, which are compounds of Formula I, wherein $R^2$ is $OR^7$ and wherein variables $R^1$ to $R^7$ are as previously defined in Formula I, supra. In step 1 oxindoles of type D where $R^2$ is equal to benzyloxy, prepared as described in Scheme 3, can undergo a Suzuki-type palladium-catalyzed coupling with pyridines, such as E, which are substituted at the three position with a boronic acid or ester (e.g. L is OH or O-alkyl), to furnish compounds of type K. Hydrogenolysis of K, preferably employing a catalytic amount of palladium on carbon under a hydrogen atmosphere, affords phenols of type L In step 3, L can undergo Mitsunobo-type coupling with primary or secondary alcohols to provide ethers of type M. Preferably, employing 1.5 to 2 equivalent of the primary or secondary alcohol in the presence of cyanomethylene-tri-n-butylphosphorane at elevated temperatures.

Scheme 5 illustrates the synthesis of compounds of Formula I ($X=O$, S, $—NR^1$) wherein variables $R^1$ to $R^6$ are as defined in Formula I, supra Benzoxazolone or benzoxathiazolone or benzoimidazolone of type O can be prepared by reaction of aminophenyl N ($X=OH$, SH, $—NHR^1$; $Y=Br$ or H) with CDI (Carbodiimide) or (tri)phosgene to generate compound O which can then be treated with iodoalkyl in the precense of base (e.g. $K_2CO_3$) to furnish P. Bromination of P (Y=H) by N-bromosuccinimide or bromine to generate intermediate Q, which can then undergo Suzuki-type palladium-catalyzed coupling with optionally substituted pyridyl borinic acid or ester, such as R, to generate a compound of Formula I ($X=O$, S, $—NR^1$), Scheme 6:

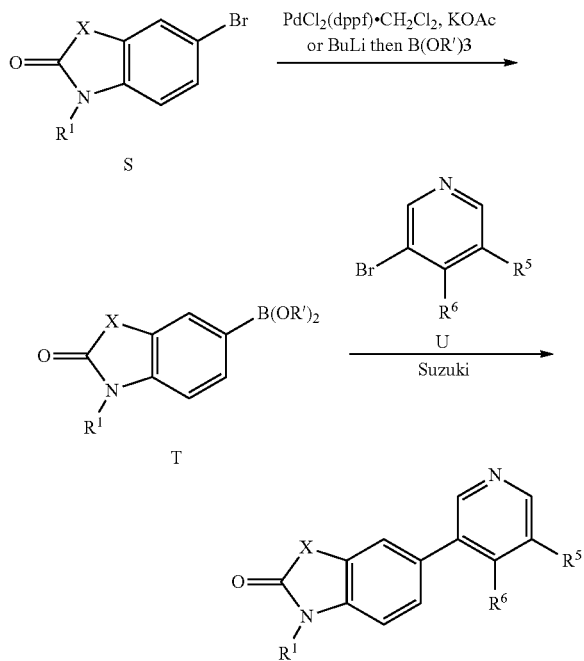

Scheme 6 described an alternative synthesis of compound of Formula I, (X=O, S, —NR$^1$), wherein variables R$^1$ to R$^6$ are as defined in Formula I, supra. A compound of type S (benzoxazolone when X is O, benzothiazolone when X is S, benzoimidazolone when X is N) can be converted into the corresponding boronic ester using 4,4,4',4',5,5,5',5'-octamethyl-2,2'-bi(1,3,2-dioxaborolane) and PdCl$_2$(dppf) or into boronic acid using lithium-halogen exchange followed by boronation to generate intermediate T. Intermediate T undergoes Suzuki coupling reaction with optionally substituted 3-bromo-pyridyne U to generate a compound of the invention.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in pharmaceutically acceptable salt form, exhibit valuable pharmacological properties, e.g. aldosterone synthase and/or CYP11B1 modulating properties, e.g. as indicated in in vitro and in vivo tests as provided in the next sections and are therefore indicated for therapy.

Compounds of the invention may be useful in the treatment of an indication selected from: hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess. Thus, as a further embodiment, the present invention provides the use of a compound according to anyone of formulae I-VIII, or a pharmaceutically acceptable salt thereof, in therapy. In a further embodiment, the therapy is selected from a disease which is ameliorated by inhibition of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

In another embodiment, the invention provides a method of treating a disease which is ameliorated by inhibition of aldosterone synthase and/or CYP11B1 comprising administration of a therapeutically acceptable amount of a compound according to any one of formulae I-VIII. In a further embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

The pharmaceutical composition or combination of the present invention can be in unit dosage of about 0.01-500 mg of active ingredient(s) for a subject of about 50-70 kg, or about 0.01-250 mg or about 0.01-150 mg or about 0.01-100 mg, or about 0.01-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro tests. The compounds of the present invention can be applied in vitro in the form of solutions, e.g., preferably aqueous solutions. The dosage in vitro may range between about $10^{-3}$ molar and $10^{-9}$ molar concentrations. A therapeutically effective amount in vivo may range depending on the route of administration, between about 0.0001-500 mg/kg, or between about 0.0001-100 mg/kg, or between about 0.0003-10 mg/kg.

The activity of a compound according to the present invention can be assessed by the in vitro methods described below.

In particular, the aldosterone synthase inhibitory activities in vitro can be determined by the following assay.

Human adrenocortical carcinoma NCI-H295R cell line was obtained from American Type Culture Collection (Manassas, Va.). Insulin/transferrin/selenium (ITS)-A supplement (100×), DMEM/F-12, antibiotic/antimycotic (100×), and fetal bovine serum (FBS) were purchased from Invitrogen (Carlsbad, Calif.). Anti-mouse PVT scintillation proximity assay (SPA) beads and NBS 96-well plates were obtained from GE Health Sciences (Piscataway, N.J.) and Corning (Acton, Mass.), respectively. Solid black 96-well flat bottom plates were purchased from Costar (Corning, N.Y.). Aldosterone and angiotensin (Ang II) were purchased from Sigma (St. Louis, Mo.). D[1,2,6,7-$^3$H(N)]aldosterone was acquired from PerkinElmer (Boston, Mass.). Nu-serum was a product of BD Biosciences (Franklin Lakes, N.J.).

For in vitro measurement of aldosterone activity, human adrenocortical carcinoma NCI-H295R cells are seeded in NBS 96-well plates at a density of 25,000 cells/well in 100 μl of a growth medium containing DMEM/F12 supplemented with 10% FCS, 2.5% Nu-serum, 1 μg ITS/ml, and 1× antibiotic/antimycotic. The medium is changed after culturing for 3 days at 37° C. under an atmosphere of 5% $CO_2$/95% air. On the following day, cells are rinsed with 100 μl of phosphate-buffered saline (PBS) and incubated with 100 μl of treatment medium containing 1 μM Ang II and a compound at different concentrations in quadruplicate wells at 37° C. for 24 hr. At the end of incubation, 50 μl of medium is withdrawn from each well for measurement of aldosterone production by an SPA using mouse anti-aldosterone monoclonal antibodies.

Measurement of aldosterone activity can also be performed using a 96-well plate format. Each test sample is incubated with 0.02 μCi of D-[1,2,6,7-$^3$H(N)]aldosterone and 0.3 μg of anti-aldosterone antibody in PBS containing 0.1% Triton X-100, 0.1% bovine serum albumin, and 12% glycerol in a total volume of 200 μl at room temperature for 1 hr. Anti-mouse PVT SPA beads (50 μl) are then added to each well and incubated overnight at room temperature prior to counting in a Microbeta plate counter. The amount of aldosterone in each sample is calculated by comparing with a standard curve generated using known quantities of the hormone.

The in vitro inhibitory activities for CYP11B1 can be determined by the following assay.

The cell line NCI-11295R was originally isolated from an adrenocortical carcinoma and has been characterized in the literature through the stimulable secretion of steroid hormones and the presence of the enzymes essential for steroidogenesis. Thus, the NCI-H295R cells have Cyp11 B1 (steroid 11 β-hydroxylase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbeoco's Modified Eagle' Ham F-12 Medium (DME/F12), which has been supplemented with Ulroser SF Serum (Soprachem, Cergy-Saint-Christophe, France), insulin, transferrin, selenite (I-T-S, Becton Dickinson Biosciences, Franklin lakes, N.J., USA) and antibiotics in 75 $cm^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin II (1D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturer's instructions.

Inhibition of the release of certain steroids can be used as a measure of the respective enzyme inhibition by the added test compounds. The dose-dependent inhibition of enzymic activity by a compound is calculated by means of an inhibition plot which is characterized by an IC50.

The IC50 values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: $Y=(d-a)/((1+(x/c)b))+a$, where: a=minimum data level, b gradient, I c=ICED, d=maximum data level, x=inhibitor concentration.

The inhibition activity of aldosterone production can also be expressed in percentage inhibition (% inhibition) at a given concentration (e.g. % inhibition at 1 μM), which is the aldosterone level when the cell is treated with the given concentration of a compound of this invention (e.g. concentration of 1 μM) versus the aldosterone excretion when cell is free of the compound of the invention:

$$\% \text{ inhibition aldosterone production} = [(Y'-X')/Y'] \times 100$$

wherein X' is the level of aldosterone when the cell is treated with a compound of Formula I and
Y' is the level of aldosterone when the cell is free of compound of Formula I.

The inhibition activity of cortisol production (CYP11B1 activity) can also be expressed in percentage inhibition (% inhibition) at a given concentration (e.g. % inhibition at 1 μM), which is the cortisol level when cell is treated with the given concentration of a compound of the invention (e.g. concentration of 1 versus the cortisol excretion when cell is free of the compound of the invention:

$$\% \text{ inhibition cortisol production} = [(Y'-X')/Y'] \times 100$$

wherein X' is the level of cortisol when the cell is treated with a compound of Formula I; and
Y' is the level of cortisol when the cell is free of compound of Formula Using the test assays (as described above) compounds of the invention exhibit inhibitory efficacy as shown in Table 1, provided infra.

TABLE 1

Inhibitory Activity of Compounds

| # | Compound | Aldosterone cell secretion (IC50 nM) | Cortisol cell secretion (% Inhib. @ 1 μM) |
|---|---|---|---|
| 1 | 1-Methyl-5-(4-trifluoromethyl-pyridin-3-yl)-1,3-dihydro-indol-2-one | 91.5 | 29.5 |
| 2 | 4-(4-Chloro-benzyloxy)-1-methyl-5-pyridin-3-yl-1,3-dihydro-indol-2-one | 5 | 83 |
| 3 | 4-Benzyloxy-1-methyl-5-pyridin-3-yl-1,3-dihydro-indol-2-one | 18 | 51 |

TABLE 1-continued

Inhibitory Activity of Compounds

| # | Compound | Aldosterone cell secretion (IC50 nM) | Cortisol cell secretion (% Inhib. @ 1 µM) |
|---|---|---|---|
| 4 | 4-Chloro-1-methyl-5-pyridin-3-yl-1,3-dihydro-indol-2-one | 10 | 85.5 |
| 5 | 4-Chloro-5-(5-diethylamino-pyridin-3-yl)-1-methyl-1,3-dihydro-indol-2-one | 58 | 78 |
| 6 | 4-Chloro-5-(5-hydroxymethyl-pyridin-3-yl)-1-methyl-1,3-dihydro-indol-2-one | 11 | 83 |
| 7 | 4-Cyclopropyl-1-methyl-5-pyridin-3-yl-1,3-dihydro-indol-2-one | 27.5 | 50 |
| 8 | 4-Methoxy-1-methyl-5-pyridin-3-y)-1,3-dihydro-indol-2-one | 36 | 84 |
| 9 | 5-(1-Methyl-2-oxo-2,3-dihydro-1H-indol-5-yl)-pyridine-3-sulfonic acid dimethylamide | 15 | 89 |
| 10 | 5-(5-Bromo-pyridin-3-yl)-1,4-dimethyl-1,3-dihydro-indol-2-one | 4 | 93 |
| 11 | 5-(5-Chloro-4-methyl-pyridin-3-yl)-4-methoxy-1-methyl-1,3-dihydro-indol-2-one | 37 | 39 |
| 12 | 5-(5-Cyclopropyl-pyridin-3-yl)-1-methyl-1,3-dihydro-indol-2-one | 2 | 79 |
| 13 | 5-(5-Ethoxy-pyridin-3-yl)-1-methyl-1,3-dihydro-indol-2-one | 20 | 83.5 |
| 14 | 5-[3,3']Bipyridinyl-5-yl-1-methyl-1,3-dihydro-indol-2-one | 18 | 60 |
| 15 | 6-Chloro-1-methyl-5-pyridin-3-yl-1,3-dihydro-indol-2-one | 171.5 | 82 |
| 16 | 3-Methyl-8-pyridin-3-yl-3H-benzothiazol-2-one | 14 | 87 |
| 17 | 6-(5-aminopyridin-3-yl)-3-methylbenzo[d]thiazol-2(3H)-one | 102 | 41 |
| 18 | 1,3-Dimethyl-5-pyridin-3-yl-1,3-dihydro-benzoimidazol-2-one | 408 | — |
| 19 | 3-Methyl-6-pyridin-3-yl-3H-benzooxazol-2-one | 472 | — |

The compound of the present invention may be administered either simultaneously with, or before or after, at least one other therapeutic agent. The compound of the present invention may be administered separately, by the same or different route of administration, or together in the same pharmaceutical composition.

In one embodiment, the invention provides a product comprising a compound according to anyone of formulae or a pharmaceutically acceptable salt thereof and at least one other therapeutic agent as a combined preparation for simultaneous, separate or sequential use in therapy. In one embodiment, the therapy is the treatment of a disease or condition mediated by aldosterone synthase and/or CYP11B1. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound according to anyone of formulae or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of formulae I-VIII, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (I) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound according to anyone of formulae or a pharmaceutically acceptable salt thereof, in the manufacture of a medicament for treating a disease or condition mediated by aldosterone synthase and/or CYP11B1, wherein the medicament is prepared for administration with another therapeutic agent. The invention also provides the use of a another therapeutic agent in the manufacture of medicament for treating a disease or condition mediated by aldosterone synthase and/or CYP11B1, wherein the medicament is prepared for administration with a compound according to anyone of formulae or a pharmaceutically acceptable salt thereof.

The invention also provides a compound according to anyone of formulae or a pharmaceutically acceptable salt thereof, for use in a method of treating a disease or condition mediated by aldosterone synthase and/or CYP11B1, wherein the compound according to anyone of formulae or a pharmaceutically acceptable salt thereof, is prepared for administration with another therapeutic agent. The invention also provides another therapeutic agent for use in a method of treating a disease or condition mediated by aldosterone synthase and/or CYP11B1, wherein the other therapeutic agent is prepared for administration with a compound according to anyone of formulae I-VIII, or a pharmaceutically acceptable salt thereof. The invention also provides a compound according to anyone of formulae I-VIII, or a pharmaceutically acceptable salt thereof, for use in a method of treating a disease or condition mediated by aldosterone synthase and/or CYP11B1, wherein the compound according to anyone of formulae I-VIII, or a pharmaceutically acceptable salt thereof, is administered with another therapeutic agent. The invention also provides another therapeutic agent for use in a method of treating a disease or condition mediated by aldosterone synthase and/or CYP11B1, wherein the other therapeutic agent is administered with a compound according to anyone of formulae I-VIII, or a pharmaceutically acceptable salt thereof.

The invention also provides the use of a compound according to anyone of formulae I-VIII, or a pharmaceutically acceptable salt thereof, in the manufacture of a medicament for treating a disease or condition mediated by aldosterone synthase and/or CYP11B1, wherein the patient has previously (e.g. within 24 hours) been treated with another therapeutic agent. The invention also provides the use of another therapeutic agent in the manufacture of a medicament for treating a disease or condition mediated by aldosterone synthase and/or CYP11B1, wherein the patient has previously (e.g. within 24 hours) been treated with a compound according to anyone of formulae I-VIII.

In one embodiment, the other therapeutic agent is selected from: HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

In still another embodiment, the invention pertains, at least in part, to methods wherein the compound of the invention (e.g., a compound according to anyone of Formulae I-VIII or a compound otherwise described herein) is administered in combination with a second agent.

The term "in combination with" a second agent or treatment includes co-administration of the compound of the invention (e.g., a compound according to anyone of Formulae I-VIII or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g., an aldosterone synthase associated disorder, such as, for example, hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries. Furthermore, the second agent may be any agent of benefit to the patient when administered in combination with the administration of a compound of the invention.

Examples of second agents include HMG-Co-A reductase inhibitors, angiotensin II receptor antagonists, angiotensin converting enzyme (ACE) Inhibitors, calcium channel blockers (CCB), dual angiotensin converting enzyme/neutral endopeptidase (ACE/NEP) inhibitors, endothelin antagonists, renin inhibitors, diuretics, ApoA-I mimics, anti-diabetic agents, obesity-reducing agents, aldosterone receptor blockers, endothelin receptor blockers, and CETP inhibitors.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

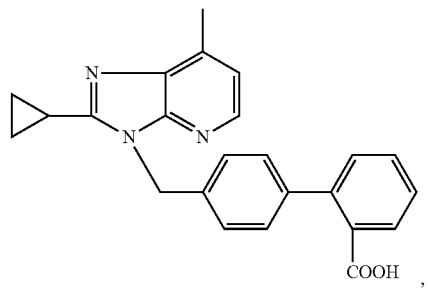 [SMILES: Cc1ccnc2c1nc(C1CC1)n2Cc1ccc(-c2ccccc2C(=O)O)cc1]

the compound with the designation SC-52458 of the following formula

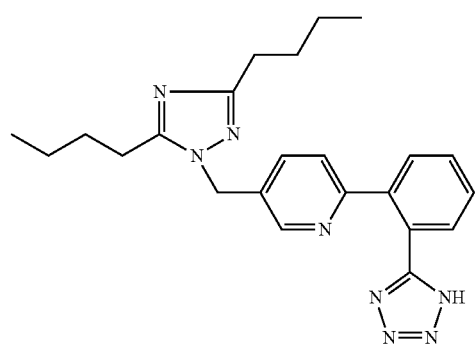

and the compound with the designation ZD-8731 of the foil wing formula

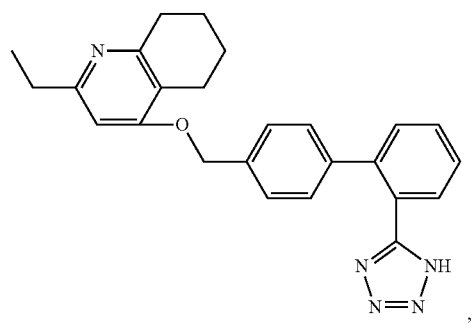 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are those agents which have been marketed, most preferred is valsartan or a pharmaceutically acceptable salt thereof.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandotapril, or, pharmaceutically acceptables salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "dual angiotensin converting enzyme/neutral endopetidase (ACE/NEP) inhibitor" includes omapatrilate (cf. EP 629627), fasidotril or fasidotrilate, or pharmaceutically acceptable salts thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

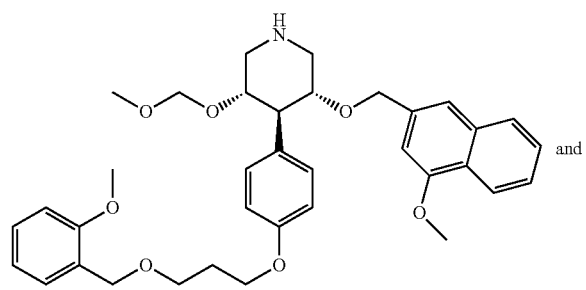

(A)

and

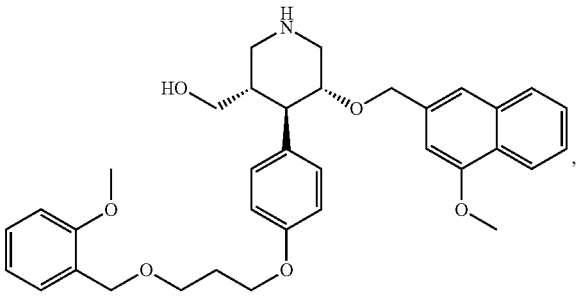

(B)

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamicle (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, giypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

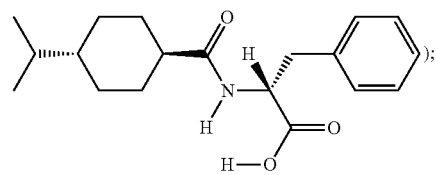 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al in *Diabetologia*, 28, 1985, 704-707 and in U.S. Pat. No. 5,705,483.

The term "GLP-1 agonists" includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1 (7-36)NH$_2$ molecule and variants and analogs thereof including GLN$^9$-GLP-1 (7-37), D-GLN$^9$-GLP-1 (7-37), acetyl LYS$^9$-GLP-1 (7-37), LYS$^{18}$-GLP-1 (7-37) and, in particular, GLP-1 (7-37)OH, VAL$^8$-GLP-1(7-37), GLY$^8$-GLP-1 (7-37), THR$^9$-GLP-1 (7-37), MET$^8$-GLP-1 (7-37) and 4-imidazopropionyl-GLP-1. Special preference is also given to the GLP agonist analog exendin-4, described by Greig at al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazoilidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl methyl}-thiazolidine-2,4-dione (DRF2189), 5-{4-[2-(5-methyl-2-phenyl-4-oxazolyl)-ethoxy)]benzyl}-thiazolidine-2,4-dione (BM-13, 1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl] methyl}thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6 Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

The term "aldosterone receptor blocker" includes spironolactone and eplerenone,

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 1815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

Exemplification of the Invention

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4-th Ed. 1952, Methods of Organic Synthesis, Thieme, Volume 21). Further, the compounds of the present invention can be produced by organic synthesis methods known to one of ordinary skill in the art as shown in the following examples.

ABBREVIATIONS

ATP: adenosine 5'-triphosphate
BINAP: racemic 2,2'-bis(diphenylphosphino)-1,1'-binaphthyl
br: broad
calcd: calculated
d: doublet dd: doublet of doublets
DIEA: diethylisopropylamine
DMF: N,N-dimethylformamide
DPPA: diphenylphosphorylazide
EDTA: ethylenediamine tetraacetic acid
EtOAc: ethyl acetate
HATU: O-(7-azobenzotriazol-1-yl)-1,1,3,3-tetramethyluroniumhexafluorophosphate
HPLC: high pressure liquid chromatography
MeOD: methanol-d4
MS: mass spectrometry
min: minutes
n.d.: not determined ppm: parts per million
PyBOP: benzotriazol-1-yloxy Tripyrrolidinophosphoniumhexafluorophosphate
s: singlet
TFA: trifluoroacetic acid
TLC: thin layer chromatography NBS: N-bromosuccinimide
AIBN: azobiisobutyronitrile AS: Aldosterone Synthase
BOC: tertiary butyl carboxy bs: broad singlet
CYP11B1: 11-beta hydroxylase
DAST: (diethylamino)sulfur trifluoride
DCM: dichloromethane
DME: 1,4-dimethoxyethane
DMSO: dimethylsulfoxide
DTT: dithiothreitol
ESI: electrospray ionization
h: hour(s)
HOBt: 1-hydroxy-7-azabenzotriazole LCMS: liquid chromatography and mass spectrometry
MeOH: methanol
m: multiplet
m/z: mass to charge ratio
NMR: nuclear magnetic resonance
Pr: propyl
rt: room temperature t: triplet
THF: tetrahydrofuran
Tris•HCl: aminotris(hydroxymethyl) methane hydrochloride
Dppf: diphenylphosphine

Example 1

1-Methyl-5-(5-methyl-pyridin-3-yl)-1,3-dihydro-indol-2-one

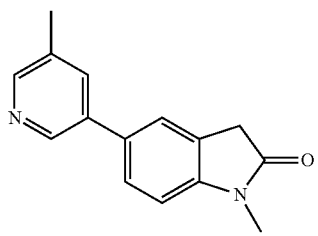 [SMILES: Cc1cncc(-c2ccc3c(c2)CC(=O)N3C)c1]

To 5-bromo-1-methyl-1,3-dihydro-indol-2-one (CAS#20870-90-0, 80 mg, 0.35 mmol) was added 5-methyl-3-pyridinyl boronic acid (CAS#173999-18-3, 55 mg, 0.39 mmol), in 1,2-dimethoxyethane (2.7 mL) and 2 M aqueous sodium carbonate (0.45 mL, 0.9 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.09 mmol/g loading, (195 mg, 0.018 mmol)] was added. The reaction vessel was sealed and was heated by microwave irradiation at 100° C. for 1.5 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 6%) to afford 1-methyl-5-(5-methyl-pyridin-3-yl)-1,3-dihydro-indol-2-one; HRMS: (ESI) m/z 239.1181 (M+H)$^+$; $^1$H NMR (400 MHz, CDCl$_3$) δ ppm 2.42 (s, 3H), 3.27 (s, 3H), 3.61 (s, 2H), 6.93 (d, J=8.1 Hz, 1H), 7.45-7.58 (m, 2H), 7.67 (s, 1H), 8.42 (s, 1H), 8.63 (s, 1H).

Example 2

5-(5-Fluoro-pyridin-3-yl)-1-methyl-1,3-dihydro-indol-2-one

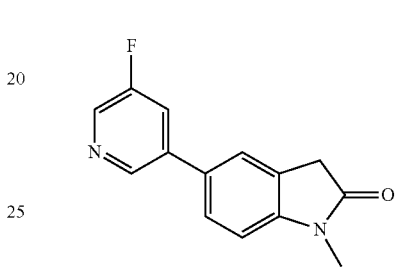

To a solution of 5-fluoropyridine-3-boronic acid (CAS#872041-86-6, 80 mg, 0.57 mmol) in 1,2-dimethoxyethane (0.7 mL) was added water (0.3 mL) and ethanol (0.2 mL). The solution was then charged with sodium carbonate (60 mg, 0.57 mmol), 5-bromo-1-methyl-1,3-dihydro-indol-2-one (CAS#20870-90-0, 132 mg, 0.57 mmol), and dichlorobis(triphenylphosphine)palladium (II) (CAS#13965-03-2, 20.3 mg, 0.029 mmol). The reaction vessel was sealed and is heated by microwave irradiation at 150° C. for 10 minutes. The reaction mixture was cooled to room temperature, filtered and concentrated. The resulting residue was partially purified by semi-preparative reverse phase HPLC (20 to 90% acetonitrile/water vii 0.1% TEA). Final purification was accomplished via silica gel flash chromatography (methanol-dichloromethane, 0 to 7%) to afford 5-(5-fluoro-pyridin-3-yl)-1-methyl-1,3-dihydro-indol-2-one, MS: (ES+) m/z 243 (M+H)$^+$; $^1$H NMR (400 MHz, DMSO-d$_6$) δ ppm 3.18 (s, 3H), 3.64 (s, 2H), 7.13 (d, J=7.8 Hz, 1H), 7.73-7.77 (m, 2H), 8.03 (d, J=9.7 Hz, 1H), 8.53 (d, J=2.7 Hz, 1H), 8.79 (s, 1H).

Example 3 a) 1-Methyl-5-(4,4,5,5-tetramethyl-[1,3,2]dioxaborolan-2-yl)-1,3-dihydro-indol-2-one

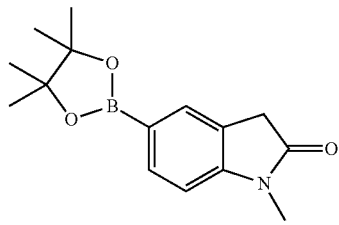 [SMILES: CN1C(=O)Cc2cc(B3OC(C)(C)C(C)(C)O3)ccc21]

To a solution of 5-bromo-1-methyl-1,3-dihydro-indol-2-one (CAS#20870-90-0, 4.07 g, 18.00 mmol), in DMSO (50 mL) was added bis(pinacolato)diboron (5.03 g, 19.80 mmol), and potassium acetate (5.30 g, 54.0 mmol). Next, [1,1'-bis (diphenylphosphino)-ferrocene]-dichloropalladium(II) complexed with dichloromethane (CAS#72287-26-4, 0.417 g, 0.540 mmol) was added. The reaction mixture was degassed by bubbling nitrogen through the solution for 3 minutes. The reaction was then heated at 80° C. for 18 hr. The reaction was then poured into ice-water and extracted three times with diethyl ether. The organic extracts were combined, washed with brine, dried over anhydrous sodium sulfate, filtered and concentrated. The resulting residue was purified by silica gel flash chromatography (ethyl acetate-heptane, 0 to 70%) to afford 1-methyl-5-(4,4,5,5-tetramethyl-[1,3,2]dioxaborolan-2-yl)-1,3-dihydro-indol-2-one; $^1$H NMR (400 MHz, CDCl$_3$) δ ppm 1.35 (s, 12H), 3.23 (s, 3H), 3.51 (s, 2H), 6.83 (d, J=7.6 Hz, 1H), 7.69 (s, 1H), 7.77 (d, j=7.8 Hz, 1H).

b) 5-(5-Ethoxy-pyridin-3-yl)-1-methyl-1,3-dihydro-indol-2-one

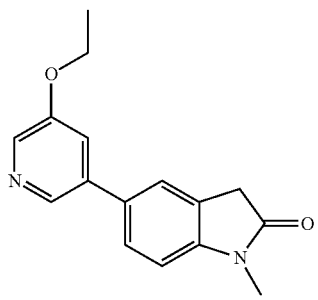 [SMILES: CCOc1cncc(-c2ccc3c(c2)CC(=O)N3C)c1]

To 1-methyl-5-(4,4,5,5-tetramethyl-[1,3,2]dioxaborolan-2-yl)-1,3-dihydro-indol-2-one (137 mg, 0.5 mmol) was added 3-bromo-5-ethoxy-pyridine (CAS#17117-17-8, 112 mg, 0.55 mmol), tripotassium phosphate (266 mg, 1.25 mmol) and DMF (2.5 mL). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.09 mmol/g loading, (300 mg, 0.027 mmol)] was added. The reaction vessel was sealed and was heated by microwave irradiation at 100° C. for 75 minutes. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 5%) to furnish 5-(5-ethoxy-pyridin-3-yl)-1-methyl-1,3-dihydro-indol-2-one; HRMS: (ESI) m/z 269.1287 (M+H)$^+$; $^1$H NMR (400 MHz, CDCl$_3$) δ ppm 1.49 (t, J=6.9 Hz, 3H), 3.27 (s, 3H), 3.62 (s, 2H), 4.18 (q, J=66 Hz, 2H), 6.93 (d, J=8.1 Hz, 1H), 7.43 (s, 1H), 7.46-7.57 (m, 2H), 8.26 (d, J=2.5 Hz, 1H), 8.43 (d, J=1.5 Hz, 1H).

Example 4

1-Methyl-5-[5-(2-methyl-[1,3]dioxolan-2-yl)pyridin-3-yl]-1,3-dihydro-indol-2-one

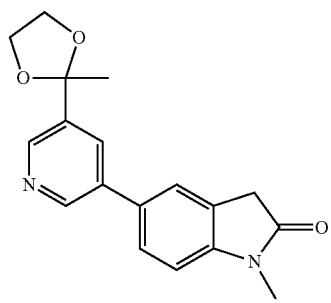 [SMILES: CN1C(=O)Cc2cc(-c3cncc(C4(C)OCCO4)c3)ccc21]

To 1-methyl-5-(4,4,5,5-tetramethyl-[1,3,2]dioxaborolan-2-yl)-1,3-dihydro-indol-2-one (109 mg, 0.4 mmol), prepared as described in Example 3a, was added 3-bromo-5-(2-methyl-1,3-dioxolan-2-yl)pyridine (CAS#59936-01-5, 107 mg, 0.44 mmol), 1,2-dimethoxyethane (3.0 mL), and 2 M aqueous sodium carbonate (0.45 mL, 0.9 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (182 mg, 0.02 mmol)] was added. The reaction vessel was sealed and was heated by microwave irradiation at 105° C. for 3 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 6%) to afford 1-methyl-5-[5-(2-methyl-[1,3]-dioxolan-2-yl)-pyridin-3-yl]-1,3-dihydro-indol-2-one; HRMS: (ESI) m/z 311.1395 (M+H)+; $^1$H NMR (400 MHz, CDCl$_3$) δppm 1.73 (s, 3H), 3.28 (s, 3H), 3.62 (s, 2H), 3.82-3.88 (m, 2H), 4.08-4.16 (m, 2H), 6.94 (d, J=7.8 Hz, 1H), 7.49-7.58 (m, 2H), 7.97 (s, 1H), 8.71 (d, J=2.0 Hz, 1H), 8.77 (d, J=2.3 Hz, 1H).

Example 5

5-(1-Methyl-2-oxo-2,3-dihydro-1H-indol-5-yl)-nicotinamide

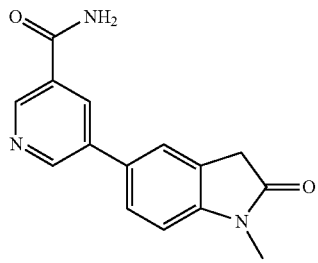 [SMILES: CN1C(=O)Cc2cc(-c3cncc(C(N)=O)c3)ccc21]

To a solution of 1-methyl-5-(4,4,5,5-tetramethyl-[1,3,2]dioxaborolan-2-yl)-1,3-dihydro-indol-2-one, prepared as described in Example 3a (75 mg, 0.26 mmol) in 12-dimethoxyethane (0.7 mL) was added water (0.3 mL) and ethanol (0.2 ml). The solution was then charged with sodium carbonate (27.6 mg, 0.26 mmol) and 5-bromonicotinamide (CAS#28733-43-9, 53.5 mg, 0.26 mmol) and dichlorobis(triphenylphosphine)palladium (II) (CAS#13965-03-2, 9.1 mg, 0.013 mmol). The reaction vessel was sealed and was heated by microwave irradiation at 150° C. for 10 minutes. The reaction mixture was cooled to room temperature, filtered and concentrated. The resulting residue was purified by silica gel flash chromatography (methanol-dichloromethane, 0 to 10%) to furnish 5-(1-methyl-2-oxo-2,3-dihydro-1H-indol-5-yl)-nicotinamide; MS: (ES+) m/z 268 (M+H)$^+$; $^1$H NMR (400 MHz, DMSO-d$_6$) δ ppm 3.16 (s, 3H), 3.63 (s, 2H), 7.11 (d, J=8.8 Hz, 1H), 7.62 (br. s., 1H), 7.69-7.75 (m, 2H), 8.22 (br. s., 1H), 8.42 (t, J=2.0 Hz, 1H), 8.94 (dd, J=18.9, 1.96 Hz, 2H).

Example 6 a) 3-Bromo-4-vinyl-pyridine

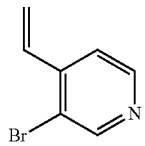

To a solution of methyltriphenylphosphonium bromide (2.14 g, 6.00 mmol) in THF (27 mL) at −78° C. was added n-butyllithium (2.5 M in hexanes, 1.8 mL, 4.5 mmol). The resulting yellow reaction mixture was stirred for 30 min at −78° C. In a separate flask THF (6 ml) was added to 3-bromoisonicotinaldehyde (CAS#113118-81-3, 558 mg, 3.00 mmol). The resulting 3-bromoisonicotinaldehyde solution was the transferred, via cannula, to the phosphonium ylide mixture followed by a 2 mL THF wash. The reaction was allowed to warm to room temperature over 60 minutes and then permitted to stir for an additional 30 minutes. The reaction was then quenched with saturated aqueous sodium bicarbonate and diluted with ethyl acetate. The layers were separated and the organic layer was washed with saturated aqueous sodium bicarbonate. The organic layer was concentrated to near dryness. The resulting residue was then diluted with ethyl acetate and 1M sodium bisulfate and the layers were separated. The organic layer was extracted two additional times with 1M sodium bisulfate. The aqueous layers were combined, diluted with dichloromethane, and neutralized via the careful addition of saturated aqueous sodium bicarbonate and solid sodium carbonate. The layers were separated and the now basic aqueous layer was extracted three additional times with dichloromethane. The dichloromethane layers were combined, dried over anhydrous sodium sulfate, filtered and concentrated. The resulting residue was purified by silica gel flash chromatography (ethyl acetate-dichloromethane, 0 to 16%) to furnish 3-bromo-4-vinyl-pyridine; MS: (ES+) m/z 183.9 (M+H)$^+$ b) 1-Methyl-5-(4-vinyl-pyridin-3-0)-1,3-dihydro-indol-2-one

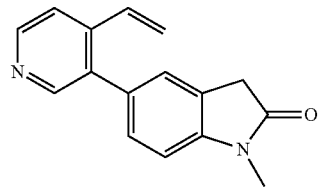 [SMILES: C=Cc1ccncc1-c1ccc2c(c1)CC(=O)N2C]

To 1-methyl-5-(4,4,5,5-tetramethyl-[1,3,2]dioxaborolan-2-yl)-1,3-dihydro-indol-2-one (135 mg, 0.49 mmol), prepared as described in Example 3a, was added 3-bromo-4-vinyl-pyridine (100 mg, 0.54 mmol), 1,2-dimethoxyethane (3.0 mL), and 2 M aqueous sodium carbonate (0.560 mL, 1.1 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (225 mg, 0.025 mmol)] was added. The reaction vessel was sealed and was heated by microwave irradiation at 115° C. for 4 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 6%) to furnish 1-methyl-5-(4-vinyl-pyridin-3-yl)-1,3-dihydro-indol-2-one; MS: (ES+) m/z 251.3 (M+H)$^+$.

c) 5-(4-Ethyl-pyridin-3-yl)-1-methyl-1,3-dihydro-indol-2-one

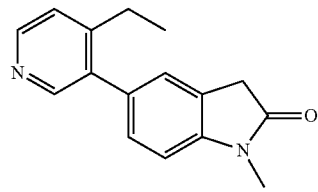 [SMILES: CCc1ccncc1-c1ccc2c(c1)CC(=O)N2C]

To a solution of 1-methyl-5-(4-vinyl-pyridin-3-yl)-1,3-dihydro-indol-2-one (30 mg, 0.12 mmol) in ethanol (1 mL) was added 10% palladium on carbon (18 mg, 0.02 mmol). The atmosphere over the reaction mixture was evacuated and the reaction was placed under an atmosphere of hydrogen gas via a balloon. The reaction was stirred for 25 minutes. The reaction mixture was then filtered through a plug of Celite® and the filtrate was then concentrated to dryness. The resulting residue was purified by silica gel flash chromatography (ethanol-dichloromethane, 0 to 6%) to afford 5-(4-ethyl-pyridin-3-yl)-1-methyl-1,3-dihydro-indol-2-one. The HCl salt of the title compound was prepared by dissolution in diethyl ether followed by treatment with an excess of 1N HCl in diethyl ether. The resulting heterogeneous solution was concentrated to furnish the HCl salt of 5-(4-ethyl-pyridin-3-yl)-1-methyl-1,3-dihydro-indol-2-one. HRMS: (ESI) m/z 253.1335 (M+H)+; $^1$H NMR (400 MHz, CD$_3$OD) δ ppm 1.23 (t, J=7.6 Hz, 3H), 2.93 (q, J=7.6 Hz, 2H), 3.28 (s, 3H), 3.66 (s, 2H), 7.16 (d, J=8.6 Hz, 1H), 7.33-7.43 (m, 2H), 8.05 (d, J=6.3 Hz, 1H), 8.65 (s, 1H), 8.71 (d, J=6.1 Hz, 1H).

Example 7 a) 5-Bromo-pyridine-3-sulfonic acid 4-fluoro-benzylamide

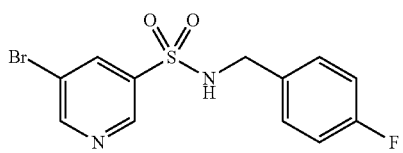 [SMILES: O=S(=O)(NCc1ccc(F)cc1)c1cncc(Br)c1]

To a solution of 5-bromo-3-pyridinesulfonyl chloride (CAS#65001-21-0, 256 mg, 1.0 mmol) in dichloromethane (8 mL) at 0° C. was added diisopropylethylamine (0.350 mL, 2.0 mmol) followed by 4-fluorobenzylamine (CAS#140-75-0, 0.11 mL, 0.95 mmol). The reaction was put at room temperature and stirred for 15 minutes. The reaction was then poured into water and diluted with dichloromethane. The layers were separated and the aqueous layer was extracted two additional times with dichloromethane. The organic layers were combined, dried over anhydrous sodium sulfate, filtered, and concentrated to furnish 5-bromo-pyridine-3-sulfonic acid 4-fluoro-benzylamide without the need for further purification. MS: (ES+) m/z 344.8 (M+H)+ b) 5-(1-Methyl-2-oxo-2,3-dihydro-1H-indol-5-yl)-pyridine-3-sulfonic acid 4-fluoro-benzylamide

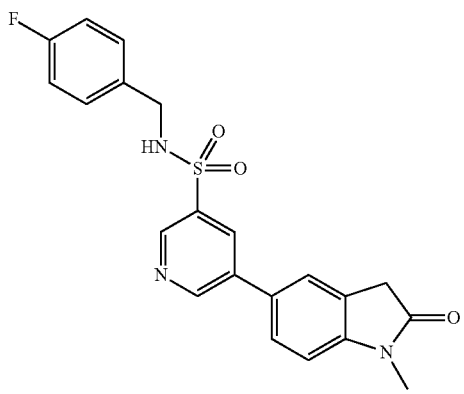 [SMILES: CN1C(=O)Cc2cc(-c3cncc(S(=O)(=O)NCc4ccc(F)cc4)c3)ccc21]

To 1-methyl-5-(4,4,5,5-tetramethyl-[1,3,2]dioxaborolan-2-yl)-1,3-dihydro-indol-2-one, prepared as described in Example 3a (124 mg, 0.45 mmol) was added bromo-pyridine-3-sulfonic acid 4-fluoro-benzylamide (140 mg, 0.41 mmol), tripotassium phosphate (260 mg, 1.25 mmol) and DMF (2.5 mL). The reaction mixture was degassed and placed under an argon atmosphere, at which time tetrakis(triphenylphosphine)palladium(0), (23 mg, 0.02 mmol)] was added. The reaction vessel was sealed and was heated by microwave irradiation at 100° C. for 60 minutes. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered, and concentrated. The resulting residue was purified by silica gel flash chromatography (heptane-ethyl acetate, 20 to 100%) to furnish 5-(1-methyl-2-oxo-2,3-dihydro-1H-indol-5-yl)-pyridine-3-sulfonic acid 4-fluoro-benzylamide; HRMS: (ESI) m/z 412.1136 (M+H)+; $^1$H NMR (400 MHz, DMSO-d$_6$) δ ppm 3.17 (s, 3H), 3.65 (s, 2H), 4.12 (s, 2H), 7.03 (t, J=8.8 Hz, 2H), 7.14 (d, J=8.1 Hz, 1H), 7.25 (dd, J=8.6, 5.6 Hz, 2H), 7.65 (s, 1H), 7.67 (d, J=8.1 Hz, 1H), 8.20 (t, J=2.3 Hz, 1H), 8.44 (t, J=6.3 Hz, 1H), 8.80 (d, J=2.0 Hz, 1H), 9.04 (d, J=2.3 Hz, 1H).

Example 8

N-[5-(1-Methyl-2-oxo-2,3-dihydro-1H-indol-5-yl)-pyridin-3-yl]-methanesulfonamide

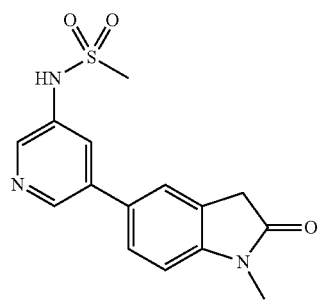 [SMILES: CN1C(=O)Cc2cc(-c3cncc(NS(C)(=O)=O)c3)ccc21]

To a solution of 5-(5-amino-pyridin-3-yl)-1-methyl-1,3-dihydro-indol-2-one, prepared as described in Example 3, (35 mg, 0.146 mmol), in dichloromethane (2.0 mL) was added diisopropylethylamine (75 pt, 0.44 mmol). The reaction was cooled to −10° C. and methanesulfonyl chloride (22 μL, 0.28 mmol) was added. After 15 minutes the reaction was quenched with saturated aqueous sodium bicarbonate and diluted with dichloromethane. The layers were separated and the organic layer was dried over sodium sulfate, filtered and concentrated. The resulting residue was dissolved in methanol (5 mL) and treated with 2 M aqueous sodium hydroxide (0.5 mL, 1 mmol) and permitted to stir at room temperature for 10 minutes. The reaction was then diluted with dichloromethane and water and the pH of the solution was brought to ca. 7 via the careful addition of 1M aqueous HCl. The layers were separated and the aqueous layer was extracted four additional times with dichloromethane and one time with ethyl acetate. The organic layers were combined, dried over anhydrous sodium sulfate, filtered and concentrated. The resulting residue was purified by silica gel flash chromatography (ethanol-dichloromethane, 0 to 7%) to furnish N-[5-(1-methyl-2-oxo-2,3-dihydro-1H-indol-5-yl)-pyridin-3-yl]-methanesulfonamide; HRMS: (ES+) m/z 318.0912 (M+H)+; $^1$H NMR (400 MHz, CDCl$_3$) δ ppm 3.11 (s, 3H), 3.28 (s, 3H), 3.62 (s, 2H), 6.94 (d, J=8.1 Hz, 1H), 7.50 (s, 1H), 7.51-7.59 (m, 1H), 7.91 (s, 1H), 8.41 (d, J=2.5 Hz, 1H), 8.67 (d, J=1.8 Hz, 1H).

Example 9

N-[5-(1-Methyl-2-oxo-2,3-dihydro-1H-indol-5-yl)-pyridin-3-yl]-isobutyramide

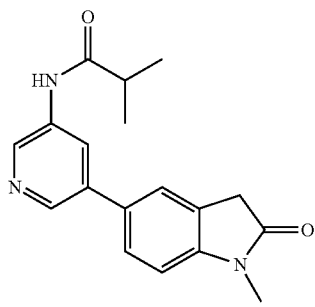 [SMILES: CC(C)C(=O)Nc1cncc(-c2ccc3c(c2)CC(=O)N3C)c1]

To a solution of 5-(5-amino-pyridin-3-yl)-1-methyl-1,3-dihydro-indol-2-one, prepared as described in Example 3, (30 mg, 0.125 mmol), in dichloromethane (6.0 mL) was added diisopropylethylamine (55 pt, 0.313 mmol). The reaction was cooled to 0° C. and isobutyryl chloride (20 pit, 0.19 mmol) was added. The reaction was placed at room temperature, and then after 10 minutes, the reaction was poured in to water and diluted with dichloromethane. The layers were separated and the aqueous layer was extracted two additional times with dichloromethane. The organic layers were combined, dried over anhydrous sodium sulfate, filtered, and concentrated. The resulting residue was purified by silica gel flash chromatography (ethanol-dichloromethane, 0 to 7%) to provide; N-[5-(1-methyl-2-oxo-2,3-dihydro-1H-indol-5-yl)-pyridin-3-yl]-isobutyramide. HRMS: (ES+) m/z 310.1563 (M+H)+; $^1$H NMR (400 MHz, DMSO-$d_6$) δ ppm 1.13 (d, J=6.8 Hz, 6H), 2.59-2.67 (m, 1H), 3.15 (s, 3H), 3.63 (s, 2H), 7.10 (d, J=−8.1 Hz, 1H), 7.55-7.58 (m, 2H), 7.59 (s, 1H), 8.33 (t, J=2.2 Hz, 1H), 8.51 (d, J=2.0 Hz, 1H), 8.65 (d, J=2.3 Hz, 1H), 10.09 (a, 1H).

Example 10 a) (5-Bromo-pyridin-3-0)-ethyl-amine and (5-Bromo-pyridin-3-0)-diethyl-amine

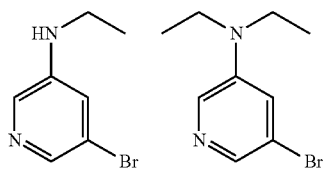

To a solution of 3-amino-5-bromopyridine (CAS#13535-01-8, 520 mg, 3.0 mmol) in THF (12 mL) at −78° C. was added potassium bis(trimethylsilyl)amide (0.5 M in toluene, 6.9 mL, 3.45 mmol). The reaction was stirred for 20 minutes at −78° C. and was then charged with iodoethane (0.25 mL, 3.15 mmol). The reaction was stiffed for an additional 30 minutes, at which time mixture was charged with additional potassium bis(trimethylsilyl)amide (0.5 M in toluene, 6.9 mL, 3.45 mmol) and iodoethane (0.25 mL, 3.15 mmol). The reaction was then permitted to warm to −20° C. over 2 h at which time it was quenched with aqueous ammonium hydroxide (5 mL) and was stirred for 30 minutes at room temperature. The reaction was then diluted with brine and ethyl acetate. The layers were separated and the aqueous layer was extracted two additional times. The organic layers were combined, dried over anhydrous sodium sulfate, filtered, and concentrated. The resulting residue was purified by silica gel flash chromatography (ethyl acetate-heptane, 0 to 60%) to afford both (5-bromo-pyridin-3-yl)-ethyl-amine and (5-bromo-pyridin-3-yl)-diethyl-amine separately.

(5-bromo-pyridin-3-yl)-ethyl-amine: MS: (ES+) m/z 200.9 (M+H)+

(5-bromo-pyridin-3-yl)-diethyl-amine: MS: (ES+) m/z 229.0 (M+H)+ b) 5-(5-Diethylamino-pyridin-3-0)-1-methyl-1,3-dihydro-indol-2-one

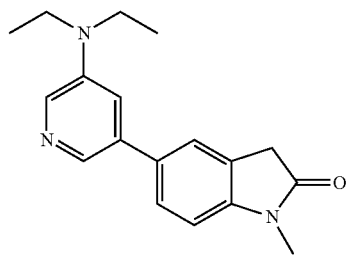 [SMILES: CCN(CC)c1cncc(-c2ccc3c(c2)CC(=O)N3C)c1]

The above compound was prepared in a similar fashion as described in Example 4; HRMS (ES+) m/z 296.1769 (M+H)+; $^1$H NMR (400 MHz, DMSO-$d_6$) δ ppm 1.12 (t, J6.9 Hz, 6H), 3.15 (s, 3H), 3.42 (q, J=6.9 Hz, 4H), 3.61 (s, 2H), 7.06 (d, J56 Hz, 1H), 7.10 (t, 1H), 7.56-7.61 (m, 2H), 8.00 (d, J=2.8 Hz, 1H), 8.03 (d, J=1.8 Hz, 1H).

c) 5-(5-Ethylamino-pyridin-3-yl)-1-methyl-1,3-dihydro-indol-2-one

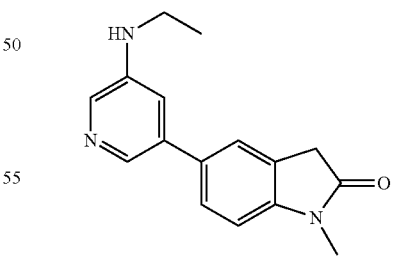

The above compound was prepared in a similar fashion as described in Example 4; HRMS: (ES+) m/z 268.1451 (M+H)+; $^1$H NMR (400 MHz, DMSO-$d_6$) δ ppm 1.19 (t, J=7.1 Hz, 3H), 3.12 (q, 2H), 3.15 (s, 3H), 3.61 (s, 2H), 5.86 (t, J=54 Hz, 1H), 7.03 (1, Hz, 1H), 7.06 (d, J=8.8 Hz, 1H), 7.53-7.58 (m, 2H), 7.90 (d, J=25 Hz, 1H), 8.00 (d, J=1.8 Hz, 1H).

Example 11 a) Ethanesulfonic acid (5-bromo-pyridin-3-ylmethyl)-amide

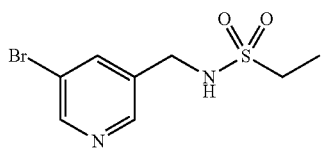

To a solution of 5-bromo-3-pyridinecarboxaldehyde (CAS#113118-81-3, 450 mg, 2.4 mmol) in dichloroethane (15 mL) was added ethanesulfonamide (CAS#1520-70-3, 175 mg, 1.6 mmol), acetic acid (0.18 mL 3.2 mmol), triethylamine (0.45 mL, 3.2 mmol) and sodium triacetoxyborohydride (1.0 g, 4.8 mmol). The reaction was stirred at room temperature for 3 hours, at which time it was diluted with dichloromethane and saturated aqueous sodium bicarbonate. The layers were separated and the aqueous layer was extracted two additional times with dichloromethane. The organic layers were combined, dried over anhydrous sodium sulfate, filtered, and concentrated. The resulting residue was purified by silica gel flash chromatography (ethyl acetate-heptane, 10 to 100%) to provide ethanesulfonic acid (5-bromo-pyridin-3-ylmethyl)-amide; MS: (ES+) m/z 278.9 $(M+H)^+$.

b) Ethanesulfonic acid [5-(1-methyl-2-oxo-2,3-dihydro-1H-indol-6-yl)-pyridin-3-ylmethyl]-amide

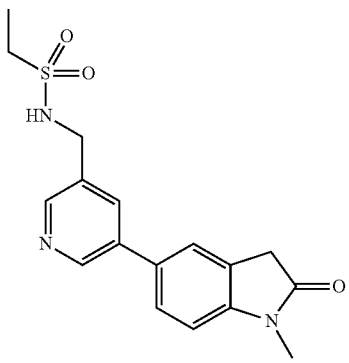 [SMILES: CCS(=O)(=O)NCc1cncc(-c2ccc3c(c2)CC(=O)N3C)c1]

The above compound was prepared in a similar fashion as described in Example 3; HRMS: (ESI) m/z 346.1225 $(M+H)^+$; $^1$H NMR (400 MHz, CDCl$_3$ δ ppm 1.41 (t, J=7, 3 Hz, 3H), 3.08 (q, J=7.5 Hz, 2H), 3.27 (s 3H), 3.62 (s, 2H), 4.43 (d, J=6.3 Hz, 2H), 4.74 (br. s., 1H), 6.94 (d, Hz, 1H), 7.50 (s, 1H), 7.53 (d, J=8.3 Hz, 1H), 7.95 (br. s., 1H), 8.55 (br. s., 1H), 8.78 (br s., 1H).

Example 12 a) Ethanesulfonic acid (5-bromo-pyridin-3-ylmethyl)-methyl-amide

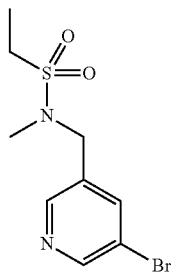

To a solution of ethanesulfonic acid (5-bromo-pyridin-3-ylmethyl)-amide (0.21 g, 0.752 mmol), prepared as described in Example 11a, in DMF (6 mL) at −10° C., was added sodium hydride (60% oil dispersion, 39 mg, 0.98 mmol). The reaction was stirred for 15 minutes at which time iodomethane (0.056 ml, 0.903 mmol) dissolved in DMF (1 mL) was added. The reaction was stirred at −10° C. for an additional 15 minutes and was then quenched with ammonia hydroxide (2 mL). The reaction was diluted with brine and extracted three times with ethyl acetate. The organic layers were combined, dried over anhydrous sodium sulfate, filtered, and concentrated. The resulting residue was purified by silica gel flash chromatography (ethyl acetate, 0 to 80%) to provide ethanesulfonic acid (5-bromo-pyridin-3-ylmethyl)-methyl-amide; MS: (ES+) m/z 293.1 $(M+H)^+$.

b) Ethanesulfonic acid methyl-[5-(1-methyl-2-oxo-2,3-dihydro-1H-indol-5-yl)-pyridin-3-ylmethyl]-amide

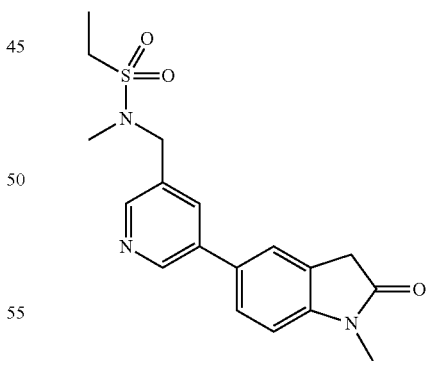

The above compound was prepared in a similar fashion as described in Example 4; HRMS: (ESI) m/z 360.1387 $(M+H)^4$; $^1$H NMR (400 MHz, CD$_2$Cl$_2$ δ ppm 1.39 (t, J=7.5 Hz, 3H), 2.82 (s, 3H), 3.08 (q, 0.1=7.3 Hz, 2H), 3.22 (s, 3H), 3.57 (s, 2H), 4.43 (s, 2H), 6.94 (d, J=8.1 Hz, 1H), 7.52 (d, J=1.3 Hz, 1H), 7.55 (d, J=8.1 Hz, 1H), 7.94 (s, 1H), 8.49 (d, J=2.0 Hz, 1H), 8.77 (d, J=2.3 Hz, 1H).

Example 13 a) N-(5-Bromo-pyridin-3-ylmethyl)-C,C,C-trifluoro-methanesulfonamide

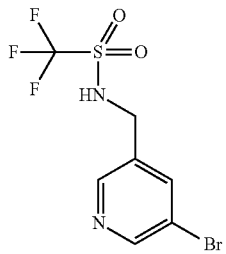 [SMILES: O=S(=O)(NCc1cncc(Br)c1)C(F)(F)F]

To a solution of 5-bromo-3-pyridinemethanamine (CAS#135124-70-8, 170 mg, 0.65 mmol) in dichloromethane (5 mL) at 0° C. was added diisopropylethylamine (0.55 mL, 3.25 mmol) and trifluoromethanesulfonyl chloride (0.083 mL, 0.78 mmol). The reaction was stirred at 0° C. for 15 minutes and then warmed to room temperature and stirred for an additional 30 minutes. The reaction was then diluted with saturated aqueous sodium bicarbonate and brine, and then further diluted with dichloromethane. The layers were separated and the aqueous layer was extracted two additional times with dichloromethane, and the organic layers were combined, dried over anhydrous sodium sulfate, filtered, and concentrated to provide N-(5-bromo-pyridin-3-ylmethyl)-C,C,C-trifluoro-methanesulfonamide with out the need for further purification. MS: (ES+) m/z 318.9 (M+H)+.

b) C,C,C-Trifluoro-N-[5-(1-ethyl-2-oxo-2,3-dihydro-1H-indol-5-yl)-pyridin-3-ylmethyl]-methanesulfonamide

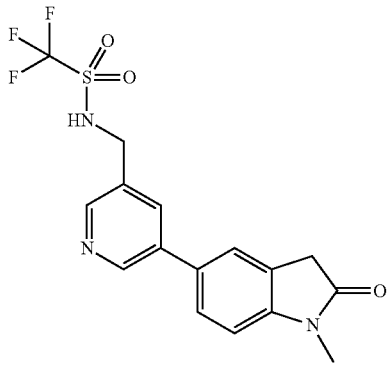 [SMILES: CN1C(=O)Cc2cc(-c3cncc(CNS(=O)(=O)C(F)(F)F)c3)ccc21]

The above compound was prepared in a similar fashion as described in Example 4; HRMS: (ES+) m/z 386.0791 (M+H)+; $^1$H NMR (400 MHz, DMSO-$d_6$) δ ppm 3.16 (s, 3H), 3.65 (s, 2H), 4.46 (s, 2H), 7.13 (d, J=8.2 Hz, 1H), 7.60-7.68 (m, 2H), 7.99 (t, J=2.1 Hz, 1H), 8.48 (d, J=2.0 Hz, 1H), 8.80 (d, J=2.3 Hz, 1H), 10.08 (br. s., 1H).

Example 14 a) Propane-2-sulfonic acid (5-bromo-pyridin-3-ylmethyl)-amide

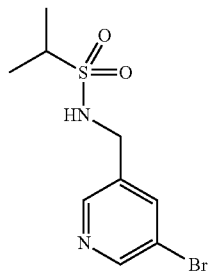

To a solution of 5-bromo-3-pyridinemethanamine (CAS#135124-70-8, 200 mg, 0.77 mmol) in DMF (8 mL) at 0° C. was added sodium hydride (60% oil dispersion, 150 mg, 3.8 mmol) followed by isopropylsulfonyl chloride (0.13 mL, 1.16 mmol). The reaction was stirred for 30 minutes and then diluted with brine and dichloromethane. The pH of the aqueous layer was adjusted to ca. 7 by the addition of acetic acid and the layers were separated. The aqueous layer was extracted two additional times with dichloromethane, and the organic layers were combined, dried over anhydrous sodium sulfate, filtered and concentrated to provide propane-2-sulfonic acid (5-bromo-pyridin-3-ylmethyl)-amide without the need for further purification; MS: (ES+) m/z 292.9 (M+H)+.

b) Propane-2-sulfonic acid [5-(1-methyl-2-oxo-2,3-dihydro-1H-indol-5-yl)-pyridin-3-ylmethyl]-amide

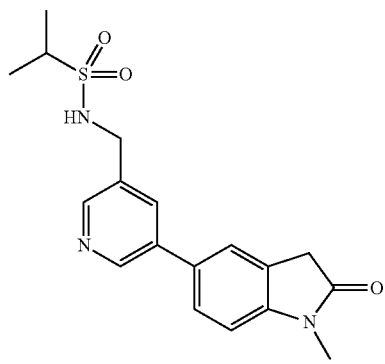 [SMILES: CC(C)S(=O)(=O)NCc1cncc(-c2ccc3c(c2)CC(=O)N3C)c1]

The above compound was prepared in a similar fashion as described in Example 4; HRMS: (ES+) m/z 359.1303 (M+H)+; $^1$H NMR (400 MHz, DMSO-$d_6$) δ ppm 1.24 (d, 0.1=6.8 Hz, 6H), 3.12-3.21 (m, 1H), 3.31 (s, 3H), 3.65 (s, 2H), 4.28 (s, 2H), 7.13 (d, J8.1 Hz, 1H), 7.64 (s, 1H), 7.67 (s, 1H), 8.01 (t, J=2.2 Hz, 1H), 8.49 (d, J=2.0 Hz, 1H), 8.78 (d, J=2.3 Hz, 1H).

Example 15 a) 1-(5-Bromo-pyridin-3-ylmethyl)-3-isopropyl-urea

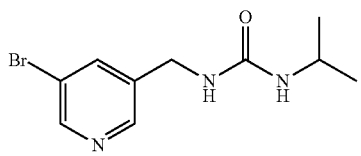

To a solution of the hydrochloride salt of 5-bromo-3-pyridinemethanamine (CAS#135124-70-8, 176 mg, 0.65 mmol) in 1,4-dioxane (10 mL) at room temperature was added diisopropylethylamine (0.550 mL, 3.27 mmol) followed by isopropyl isocyanate (CAS#1795-48-8, 0.13 mL, 1.3 mmol). The reaction was then heated to 80° C. and stirred for 15 minutes. The reaction was then cooled to room temperature, quenched with methanol, and stirred for an additional 15 minutes. The resulting solution was then concentrated in vacuo to near dryness, and diluted with dichloromethane and brine. The layers were separated and the aqueous layer was extracted two additional times. The organic layers were combined, dried over anhydrous sodium sulfate, filtered, and concentrated to furnish 1-(5-bromo-pyridin-3-ylmethyl)-3-isopropyl-urea without the need for further purification; MS: (ES+) m/z 271.9 (M+H)$^+$.

b) 1-Isopropyl-3-[5-(1-methyl-2-oxo-2,3-dihydro-1H-indol-5-yl)-pyridin-3-ylmethyl]-urea

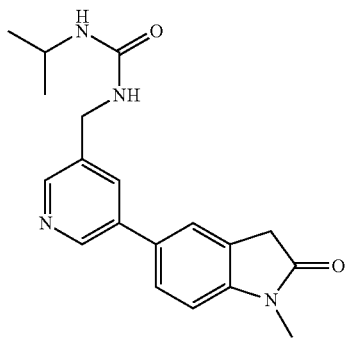 [SMILES: CC(C)NC(=O)NCc1cncc(-c2ccc3c(c2)CC(=O)N3C)c1]

The above compound was prepared in a similar fashion as described in Example 4; HRMS: (ES+) m/z 339.1825 (M+H)$^+$; $^1$H NMR (400 MHz, DMSO-d$_6$) δ ppm 1.04 (d, J=6.6 Hz, 6H), 3.16 (s 3H), 3.63 (s 2H), 3.65-3.72 (m, 1H), 4.19-4.33 (m, 2H) 5.84 (d, J=76 Hz, 1H), 6.29 (t, J=6.3 Hz, 1H), 7.11 (d, J=8.8 Hz, 1H), 7.50-7.70 (m, 2H), 7.87 (t, J=2.1 Hz, 1H), 8.40 (d J=2.0 Hz, 1H), 8.71 (d, J=2.3 Hz, 1H)

Example 16 a) 2-(5-Bromo-pyridin-3-yl)-propan-2-ol

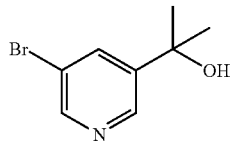

To a solution of 5-bromo-nicotinoyl chloride (900 mg, 4.1 mmol) in THF (18 mL) at −78° C. was added a 3.0 M solution of methylmagnesium bromide in diethyl ether (5.44 mL, 16.3 mmol). The reaction was stirred for 20 minutes and then quenched with saturated aqueous ammonium chloride. The reaction was then brought to room temperature, diluted with brine and ethyl acetate and the layers were separated. The aqueous layer was extracted two additional times with ethyl acetate, and the organic layers were combined, dried over anhydrous sodium sulfate, filtered, and concentrated. The resulting residue was purified by silica gel flash chromatography (ethyl acetate-heptane, 0 to 100%) to afford 2-(5-bromo-pyridin-3-yl)-propan-2-ol; MS: (ES+) m/z 216.0 (M+H)$^+$.

b) 5-[5-(1-Hydroxy-1-methyl-ethyl)-pyridin-3-yl]-1-methyl-1,3-dihydro-indol-2-one

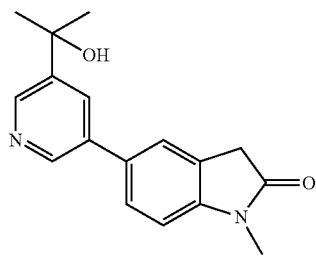 [SMILES: CN1C(=O)Cc2cc(-c3cncc(C(C)(C)O)c3)ccc21]

The above compound was prepared in a similar fashion as described in Example 4; HRMS (ESI) m/z 283.1445 (M+H)$^+$; $^1$H NMR (400 MHz, DMSO-d$_6$) δ ppm 1.50 (s, 6H), 3.16 (s, 3H), 3.63 (s, 2H), 5.27 (s, 1H), 7.10 (d, J=8.59 Hz, 1H), 7.62-7.68 (m, 2H), 8.04 (t, J=2.15 Hz, 1H), 8.63 (d, J=2.02 Hz, 1H), 8.69 (d, J=2.15 Hz, 1H).

Example 17 a) 3-Bromo-5-(1-methoxy-1-methyl-ethyl)-pyridine

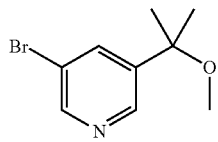

To a solution of 2-(5-bromo-pyridin-3-0)-propan-2-ol, prepared as described in Example 16a (120 mg, 0.55 mmol) in THF (3 mL) at −20° C. was added potassium bis(trimethylsilyl)amide (0.5 M in toluene, 1.45 mL, 0.72 mmol), followed by iodomethane (0.042 mL, 0.67 mmol). The reaction was permitted to warm to room temperature and stirred for 30 minutes. The reaction was then quenched with ammonium hydroxide and diluted with brine and dichloromethane and the layers were separated. The aqueous layer was extracted two additional times with dichloromethane, and the organic layers were combined, dried over anhydrous sodium sulfate, filtered, and concentrated. The resulting residue was purified by silica gel flash chromatography (ethyl acetate-heptane, 0 to 100%) to afford 3-bromo-5-(1-methoxy-1-methyl-ethyl)-pyridine; MS: (ES+) m/z 230.2 (M+H)+.

b) 5-[5-(1-Methoxy-1-methyl-ethyl)-pyridin-3-yl]-1-methyl-1,3-dihydro-indol-2-one

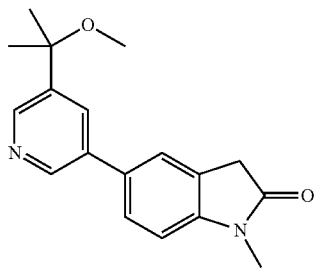 [SMILES: COC(C)(C)c1cncc(-c2ccc3c(c2)CC(=O)N3C)c1]

The above compound was prepared in a similar fashion as described in Example 4; HRMS: (ES+) m/z 297.1601 (M+H)+; 1H NMR (400 MHz, DMSO-d6) δ ppm 1.54 (s, 6H), 3.06 (s, 3H), 3.17 (s, 3H), 3.64 (s, 2H), 7.11 (d, J=8.6 Hz, 1H), 7.62-7.75 (m, 2H), 7.94 (1, J=2.3 Hz, 1H), 8.56 (d, J=2.37 Hz, 1H), 8.75 (d, J=2.3 Hz, 1H).

Example 18 a) 3-Bromo-5-isopropenyl-pyridine

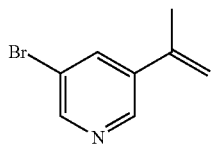

To a solution of 2-(5-bromo-pyridin-3-yl)-propan-2-ol, prepared as described in Example 16a (200 mg, 0.93 mmol) in dichloromethane (8 mL) at 0° C. was added diisopropylethylamine (0.63 mL 3.7 mmol) followed by methanesulfonyl chloride (0.14 mL, 1.85 mmol). After 5 minutes the reaction was place at room temperature and stirred for an additional half hour. The reaction was quenched with saturated aqueous sodium bicarbonate, diluted with brine and ethyl acetate and the layers were separated. The aqueous layer was extracted two additional times with ethyl acetate, and the organic layers were combined, dried over anhydrous sodium sulfate, filtered, and concentrated. The resulting residue was purified by silica gel flash chromatography (ethyl acetate-heptane, 0 to 50%) to furnish 3-bromo-5-isopropenyl-pyridine; MS: (ES+) m/z 198.0 (M+H)+.

b) 5-(5-Isopropenyl-pyridin-3-yl)-1-methyl-1,3-dihydro-indol-2-one

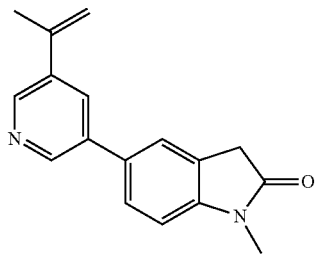 [SMILES: C=C(C)c1cncc(-c2ccc3c(c2)CC(=O)N3C)c1]

The above compound was prepared in a similar fashion as described in Example 4; HRMS: (ES+) m/z 265.1339 (M+H)+.

c) 5-(5-Isopropyl-pyridin-3-0)-1-methyl-1,3-dihydro-indol-2-one

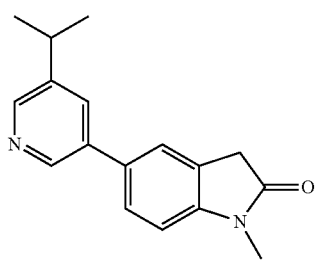 [SMILES: CC(C)c1cncc(-c2ccc3c(c2)CC(=O)N3C)c1]

To a solution of 5-(5-isopropenyl-pyridin-3-0)-1-methyl-1,3-dihydro-indol-2-one (26.5 mg, 0.10 mmol) in methanol (10 mL) was added 10% palladium on carbon (55 mg, 0.1 mmol). The atmosphere over the reaction mixture was evacuated and the reaction was placed under an atmosphere of hydrogen gas via a balloon. The reaction was stirred for 15 minutes and then filtered through a pad of Celite®. The filtrate was concentrated and the resulting residue was purified by silica gel flash chromatography (ethyl acetate-heptane, 10 to 100%) to provide 5-(5-isopropyl-pyridin-3-yl)-1-methyl-1,3-dihydro-indol-2-one; HRMS: (ES+) m/z 267.1500 (M+H)+; 1H NMR (400 MHz, DMSO-d6) δ ppm 1.28 (d, J=7.0 Hz, 6H), 295-3.06 (m, 1H), 3.16 (s, 3H), 3.63 (s, 2H), 7.10 (d, J=8.6 Hz, 1H), 7.59-7.71 (m, 2H), 7.88 (1, J=2.1 Hz, 1H), 8.42 (d, J=2.0 Hz, 1H), 8.67 (d, J=2.2 Hz, 1H).

Example 19 a) 5-Bromo-4-methyl-pyridin-3-sulfonic acid dimethylamide

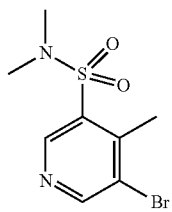

To a solution of 5-bromo-pyridine-3-sulfonic acid dimethylamide (CAS #896160-99-9, 100 mg, 0.377 mmol) in THF (3.8 mL) at −78° C. was added lithium diisopropylamide (0.5 M solution in THF, 0.85 mL, 0.42 mmol). The reaction was stirred for 15 minutes, at which time iodomethane (0.030 mL, 0.48 mmol) was added. The reaction was stirred for an additional 15 minutes and was then quenched with saturated aqueous ammonium chloride. Next, the reaction was diluted with water, dichloromethane, and saturated aqueous sodium bicarbonate. The layers were separated and aqueous layer was extracted two additional times with dichloromethane. The organic layers were combined, dried over anhydrous sodium sulfate, filtered, and concentrated. The resulting residue was purified by semi-preparative reverse phase HPLC (20 to 90% acetonitrile/water w/0.1% $NH_4OH$) to furnish 5-bromo-4-methyl-pyridine-3-sulfonic acid dimethylamide; MS: (ES+) m/z 279.0 $(M+H)^+$.

b) 4-Methyl-5-(1-methyl-2-oxo-2,3-dihydro-1H-indol-5-yl)-pyridine-3-sulfonic acid dimethylamide

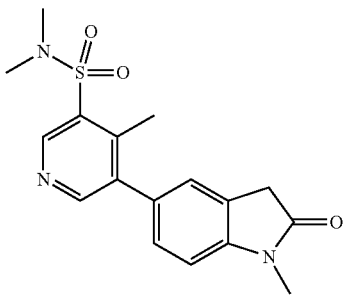 [SMILES: Cc1c(-c2ccc3c(c2)CC(=O)N3C)cncc1S(=O)(=O)N(C)C]

The above compound was prepared in a similar fashion as described in Example 4; HRMS: (ES+) m/z 346.1224 $(M+H)^+$; $^1$H NMR (400 MHz, $CDCl_3$) δ ppm 2.57 (s, 3H), 2.96 (s, 6H), 3.28 (s, 3H), 3.61 (s, 2H), 6.94 (d, J=8.1 Hz, 1H), 7.12-7.25 (m, 2H), 8.59 (s, 1H), 8.96 (s, 1H).

Example 20 a) (5-Bromo-pyridin-3-yl)-cyclopropyl-methanol

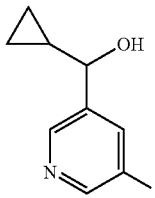

To a solution of 3-bromo-5-pyridinecarboxaldehyde (651 mg, 3.50 mmol) in THF (20 ml) at −78° C. was added cyclopropylmagnesium bromide (0.5M in THF, 7.49 ml, 3.74 mmol). After 10 minutes, additional cyclopropylmagnesium bromide (0.5M THF, 3.0 mL, 1.5 mmol) was added. After stirring for an additional five minutes the reaction was quenched with saturated aqueous ammonium chloride. The resulting mixture was diluted with dichloromethane and water and the layers were separated. The aqueous layer was extracted two additional times with dichloromethane, and the organic layers were combined, dried over anhydrous sodium sulfate, filtered, and concentrated. The resulting residue was purified by silica gel flash chromatography (ethanol-dichloromethane, 0 to 7%) to afford (5-bromo-pyridin-3-yl)-cyclopropyl-methanol; MS (ES+) m/z 228.2 $(M+H)^+$.

b) (R)- and (S)-5-[5-(Cyclopropyl-hydroxy-methyl)-pyridin-3-yl]-1-methyl-1,3-dihydro-indol-2-one

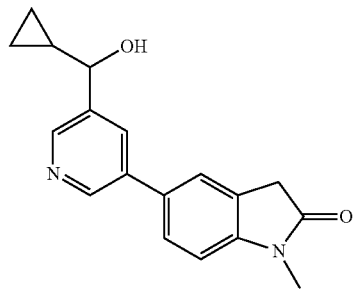 [SMILES: CN1C(=O)Cc2cc(-c3cncc(C(O)C4CC4)c3)ccc21]

The above compound was prepared in a similar fashion as described in Example 4; HRMS; (ES+) m/z 296.1452 $(M+H)^+$; $^1$H NMR (400 MHz, $CDCl_3$) δ ppm 0.43-0.61 (m, 2H), 0.62-0.82 (m, 2H), 1.19-1.35 (m, 1H), 2.05-2.16 (m, 1H), 3.28 (s, 3H), 3.62 (s, 2H), 4.14 (d, J=8.3 Hz, 1H), 6.94 (d, J=8.1 Hz, 1H), 7.51 (s, 1H), 7.55 (d, J=8.1 Hz, 1H), 8.01 (br. s., 1H), 8.63 (d, J=1.8 Hz, 1H).

Resolution of the enantiomers of the title compound was achieved by chiral HPLC using a ChiralPak AS-H column with a 1:1 ethanol-heptane mobile phase to provide (R)- or (S)-5-(5-(Cyclopropyl-hydroxy-methyl)-pyridin-3-*-1-methyl-1,3-dihydro-indol-2-one ($t_r$=11.5 min) and (R)- or (S)-5-[5-(Cyclopropyl-hydroxy-methyl)-pyridin-3-yl]-1-methyl-1,3-dihydro indol-2-one ($t_r$=13.8 min).

Example 20c (R)- and (S)-5-[5-(1-Hydroxy-propyl)-pyridin-3-yl]-1-methyl-1,3-dihydro-indol-2-one

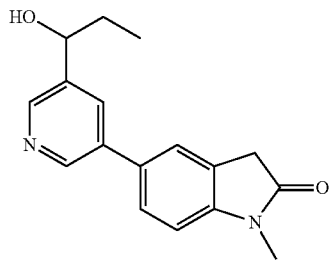 [SMILES: CCC(O)c1cncc(-c2ccc3c(c2)CC(=O)N3C)c1]

The above compound was prepared in a similar fashion as described in Example 20; HRMS: (ES+) m/z 283.1446 $(M+H)^+$; $^1$H NMR (400 MHz, $CDCl_3$) δ ppm 1.00 (t, J=7.45 Hz, 3H), 1.81-1.96 (m, 2H), 2.05 (br. s., 1H), 3.28 (s, 3H), 3.62 (s, 2H), 4.78 (t, J=6.57 Hz, 1H), 6.94 (d, J=8.08 Hz; 1H), 7.51 (s, 1H), 7.54 (d, J=8.08 Hz, 1H), 7.93 (t, J=2.02 Hz, 1H), 8.55 (d, J=2.02 Hz, 1H), 8.74 (d, J=2.27 Hz, 1H).

Resolution of the enantiomers of the title compound was achieved by chiral HPLC using a ChiralPak AS-H column with a 1:1 ethanol-heptane mobile phase provides (R)- or (S)-5-[5-(1-Hydroxy-propyl)-pyridin-3-yl]-1-methyl-1,3-dihydro-indol-2-one ($t_r$=25.8 min) and (R)- or (S)-5-[5-(1-Hydroxy-propyl)-pyridin-3-yl]-1-methyl-1,3-dihydro-indol-2-one ($t_r$=31.2 min).

Example 20d (R)- and (S)-5-[5-(1-Hydroxy-ethyl)-pyridin-3-yl]-ethyl-1-dihydro-indol-2-one

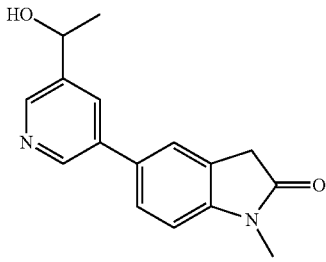 [SMILES: CC(O)c1cncc(-c2ccc3c(c2)CC(=O)N3C)c1]

The above compound was prepared in a similar fashion as described in Example 20; HRMS: (ES+) m/z 269.1288 (M+H)+; 1H NMR (400 MHz, CDCl3) δ ppm 1.61 (d, J=6.57 Hz, 3H), 2.13 (br. s, 1H), 3.29 (br. s., 3H), 3.63 (s, 2H), 5.09 (q, 1H), 6.95 (d, J=7.96 Hz, 1H), 7.52 (s, 1H), 7.54 (d, J=8.08 Hz, 1H), 8.01 (s, 1H), 8.60 (br. s., 1H), 8.74 (br, s, 1H).

Resolution of the enantiomers of the title compound was achieved by chiral supercritical fluid chromatography (SFC) using a ChiralPak IA column with a 13 methanol-supercritical $CO_2$ mobile phase at 150 bar of pressure to provide (R)- or (S)-5-[5-(1-Hydroxy-ethyl)-pyridin-3-yl]-1-methyl-1,3-dihydro-indol-2-one ($t_r$=6.7 ml) and (R)- or (S)-5-[5-(1-Hydroxy-ethyl)-pyridin-3-yl]-1-methyl-1,3-dihydro-indo-2-one 10.6 min).

Example 21

5-(5-Bromo-pyridin-3-0)-1-methyl-1,3-dihydro-indol-2-one

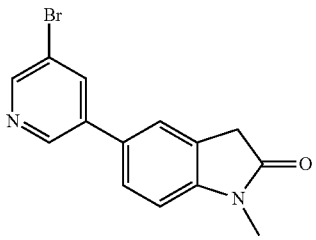 [SMILES: CN1C(=O)Cc2cc(-c3cncc(Br)c3)ccc21]

To 1-methyl-5-(4,4,5,5-tetramethyl-[1,3,2]dioxaborolan-2-yl)-1,3-dihydro-indol-2-one (1.0 g, 3.66 mmol), prepared as described in Example 3a, was added 3,5-dibromopyridine (2.6 g, 11 mmol), 1,2-dimethoxyethane (10.0 mL), and 2 M aqueous sodium carbonate (4.00 mL, 8.0 mmol). The reaction mixture was degassed and placed under an argon atmosphere, at, which time resin bound tetrakis(triphenylphosphine)palladium(0), specifically polystyrene triphenylphosphine palladium (0) [PS—PPh3-Pd(0) (Biotage), 0.11 mmol/g loading, (2.0 g, 0.220 mmol)] was added. The reaction vessel was sealed and was heated by microwave irradiation at 120° C. for 3 hours. The reaction mixture was cooled to room temperature, diluted with dichloromethane, and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 3.55%) to furnish 5-(5-bromo-pyridin-3-yl)-1-methyl-1,3-dihydro-indol-2-one; HRMS: (ESI) m/z 303.0133 (M+H)+; 1H NMR (400 MHz, CDCl3) δ ppm 3.27 (s, 3H), 3.62 (s, 2H), 6.94 (d, J=8.1 Hz, 1H), 7.48 (s, 1H), 7.50 (d, J=8.1 Hz, 1H), 8.01 (t, J=1.9 Hz, 1H), 8.64 (d, J=2.0 Hz, 1H), 8.73 (d, J=1.6 Hz, 1H).

Example 22

5-(5-Cyclopropyl-pyridin-3-yl)-1-methyl-1,3-dihydro-indol-2-one

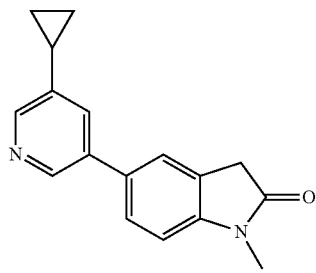 [SMILES: CN1C(=O)Cc2cc(-c3cncc(C4CC4)c3)ccc21]

To 5-(5-bromo-pyridin-3-yl)-1-methyl-1,3-dihydro-indol-2-one, prepared as described in Example 21, (100 mg, 0.330 mmol) was added potassium cyclopropyltrifluoroborate (50 mg, 0.35 mmol), THF (2 mL), water, (0.66 mL), and tripotassium phosphate (245 mg, 1.155 mmol). The reaction mixture was degassed and placed under an argon atmosphere, and then [1,1'-bis(diphenylphospihino)-ferrocene]-dichloropalladium(II) complexed with dichloromethane (CAS#72287-26-4 13.5 mg, 0.016 mmol) was added. The reaction vessel was sealed and was heated by microwave irradiation at 125° C. for 85 minutes. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-dichloromethane, 0 to 100%) to afford 5-(5-cyclopropyl-pyridin-3-yl)-1-methyl-1,3-dihydro-indol-2-one; HRMS: (ESI) m/z 265.1345 (M+H)+; 1H NMR (400 MHz, CDCl3) δ ppm 0.72-0.89 (m, 2H), 1.03-1.19 (m, 2H), 1.85-2.11 (m, 1H), 3.27 (s, 3H), 3.61 (s, 2H), 6.92 (d, J=8.1 Hz, 1H), 7.39-7.61 (m, 3H), 8.38 (d, J=1.8 Hz, 1H), 8.60 (d, J=2.0 Hz, 1H).

Example 23

5-[3,3']Bipyridinyl-5-yl-1-methyl-1,3-dihydro-indol-2-one

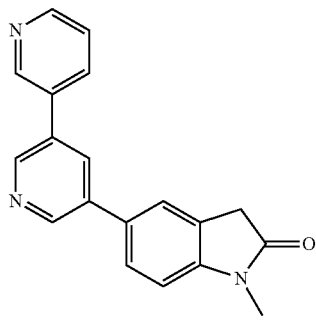 [SMILES: CN1C(=O)Cc2cc(-c3cncc(-c4cccnc4)c3)ccc21]

To 5-(5-bromo-pyridin-3-yl)-1-methyl-1,3-dihydro-indol-2-one prepared as described in Example 21, (100 mg, 0.330 mmol) was added 3-pyridine boronic acid (52.7 mg, 0.429 mmol), 1,2-dimethoxyethane (3 mL), and 2 M aqueous sodium carbonate (0.429 mL, 0.858 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (150 mg, 0.016 mmol)] was added. The reaction vessel was sealed and was heated by microwave irradiation at 120° C. for 2.5 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 1 to 8%) to furnish 5-[3,3']bipyridinyl-5-yl-1-methyl-1,3-dihydro-indol-2-one; HRMS: (ESI) m/z 302.1301 (M+H)$^+$; $^1$H NMR (400 MHz, CDCl$_3$) δ ppm 3.29 (s, 3H), 3.64 (s, 2H), 6.97 (d, J=8.1 Hz, 1H), 7.46 (dd. J=7.5, 4.9 Hz, 1H), 7.53-7.62 (m, 2H), 7.92-7.99 (m, 1H), 8.02 (t, J=2.1 Hz, 1H), 8.71 (dd, J=4.8, 1.5 Hz, 1H), 8.81 (d, J=2.3 Hz, 1H), 8.87 (d, J=2.0 Hz, 1H), 8.93 (d, J=1.8 Hz, 1H).

Example 24

1-Ethyl-5-pyridin-3-yl-1,3-dihydro-indol-2-one

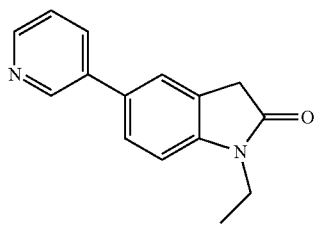 [SMILES: CCN1C(=O)Cc2cc(-c3cccnc3)ccc21]

To 5-bromo-1-ethyl-1,3-dihydro-indol-2-one (CAS#41192-37-4, 100 mg, 0.42 mmol) was added 3-pyridine boronic acid (CAS#1692-25-7, 50.2 mg, 0.41 mmol), 1,2-dimethoxyethane (2.5 mL), and 2 M aqueous sodium carbonate (0.410 mL, 0.82 mmol). The reaction mixture was degassed and placed under an argon atmosphere, at which time tetrakis(triphenylphosphine)palladium(0) (12 mg, 0.026 mmol)] was added. The reaction vessel was sealed and was heated by microwave irradiation at 100° C. for 45 minutes. The reaction mixture was cooled to room temperature, diluted with ethyl acetate and brine and the layers were separated. The aqueous layer was extracted two times with ethyl acetate, and the organic layers were combined, dried over anhydrous sodium sulfate, filtered and concentrated. The resulting residue was purified by silica gel flash chromatography (ethyl acetate-heptane, 10 to 100%) to afford 1-ethyl-5-pyridin-3-yl-1,3-dihydro-indol-2-one; HRMS: (ESI) m/z 239.1190 (M+H)$^+$; $^1$H NMR (400 MHz, CDCl$_3$) δ ppm 1.32 (t, J=7.2 Hz, 3H), 3.61 (s, 2H), 3.83 (q, J=7.3 Hz, 2H), 6.96 (d, J=8.1 Hz, 1H), 7.38 (dd, J=7.3, 4.8 Hz, 1H), 7.46-7.57 (m, 2H), 7.78-7.95 (m, 1H), 8.58 (dd, J=4.7, 1.4 Hz, 1H), 8.83 (d, J=1.8 Hz, 1H).

Example 25

1-Cyclopropyl-5-pyridin-3-yl-1,3-dihydro-indol-2-one

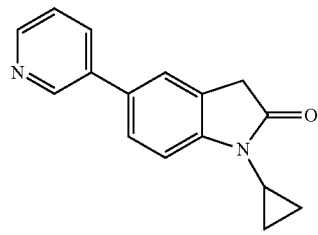 [SMILES: O=C1Cc2cc(-c3cccnc3)ccc2N1C1CC1]

To 5-pyridin-3-yl-1,3-dihydro-indol-2-one (CAS#220904-98-3, 63 mg, 0.3 mmol) was added freshly prepared tricyclopropyl-bismuthine [(J. Am. Chem. Soc., 2007, 129, 44-45), CAS#925430-09-7, 250 mg, 0.75 mmol], Cu(OAc)$_2$ (82 mg, 0.45 mmol) and dichloromethane (3 ml). The reaction mixture was degassed by sparging with argon for 5 min. Then pyridine (0.073 ml, 0.9 mmol) was added and the reaction was heated at 75° C. for 1.5 hr. The reaction mixture was cooled to room temperature and then directly loaded on to a silica gel flash chromatography column. The 1-cyclopropyl-5-pyridin-3-yl-1,3-dihydro-indol-2-one was eluted via a gradient of ethyl acetate-heptane (0 to 100%); HRMS: (ESI) m/z 251.1173 (M+H)$^+$; $^1$H NMR (400 MHz, CDCl$_3$) δ ppm 0.88-1.01 (m, 2H), 1.07-1.19 (m, 2H), 2.60-2.76 (m, 1H), 3.60 (s, 2H), 7.22-7.31 (m, 1H), 7.49 (s, 1H), 7.55 (d. J=8.5 Hz, 1H), 7.81 (br. s., 1H), 8.36 (d, J=7.7 Hz, 1H), 8.63 (br. s., 1H), 8.92 (br. s., 1H.

Example 26 a) 4-Chloro-1-methyl-1,3-dihydro-indol-2-one

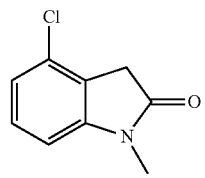

To a solution of 4-chloroisatin (CAS#6344-05-4, 3.64 g, 20.0 mmol) in acetonitrile (150 mL) was added potassium carbonate (11.1 g, 80 mmol) followed by iodomethane (2.75 mL, 44.0 mmol). The reaction was then placed at 60° C. and stirred for 40 minutes. The reaction was then cooled to room temperature, filtered and concentrated to 10% of the original volume. The reaction was then diluted with dichloromethane, water, and brine. The layers were separated and the aqueous layer was extracted two additional times with dichloromethane. The organic extracts were combined, dried over anhydrous sodium sulfate filtered, and concentrated to provide 4-chloro-1-methyl-1H-indole-2,3-dione as an orange solid without the need for further purification. The 4-chloro-1-methyl-1H-indole-2,3-dione (1.55 g, 7.92 mmol) was then treated with hydrazine hydrate (14.8 ml, 475 mmol). The reaction was then placed at 70° C. and heated to 130° C. over 20 minutes. The reaction was stirred at 130° C. for 45 minutes, at which time the reaction was placed at room temperature and cooled by the addition of ice. Once the reaction was cooled to room temperature it was diluted with dichloromethane and water and the layers were then separated. The aqueous layer was extracted an additional two times with dichloromethane, and the organic layers were combined, dried over anhydrous sodium sulfate, filtered and concentrated. The resulting residue was purified by silica gel flash chromatography (ethanol-dichloromethane 0 to 2%) to afford 4-chloro-1-methyl-1,3-dihydro-indol-2-one; MS: (ES+) m/z 182.0 (M+H)$^+$.

b) 5-Bromo-4-chloro-1-methyl-1,3-dihydro-indol-2-one

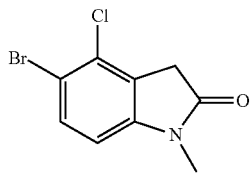

Water (25 mL) was added to 4-chloro-1-methyl-1,3-dihydro-indol-2-one (1.25 g, 6.9 mmol) and the resulting mixture was placed at 68° C. In a separate flask potassium bromide (1.64 g, 13.8 mmol) in water (25 mL) was treated with bromine (0.35 mL, 6.9 mmol), the resulting orange solution was added dropwise to the 4-chloro-1-methyl-1,3-dihydro-indol-2-one mixture over ca. 20 minutes. The resulting heterogeneous mixture was permitted to stir at 68° C. for an additional 5 minutes and then cooled to room temperature. The reaction was then diluted with dichloromethane and saturated aqueous sodium bicarbonate. The solution was then further diluted with saturated aqueous sodium thiosulfate. The layers were separated and the aqueous layer was extracted two additional times with dichloromethane. The organic extracts were combined, dried over anhydrous sodium sulfate, filtered and concentrated. The resulting residue was preadsorbed onto silica gel and purified by silica gel flash chromatography (ethyl acetate-heptane 15 to 50%) to provide 5-bromo-4-chloro-1-methyl-1,3-dihydro-indol-2-one; MS: (ES+) m/z 259.9 (M+H)$^+$.

c) 4-Chloro-1-methyl-5-pyridin-3-yl-1,3-dihydro-indol-2-one

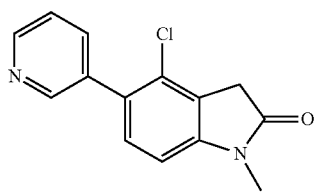

To 5-bromo-4-chloro-1-methyl-1,3-dihydro-indol-2-one (78 mg, 0.3 mmol) was added 3-pyridine boronic acid (CAS#1692-25-7, 50.2 mg, 0.41 mmol), 1,2-dimethoxyethane (2.5 mL) and 2 M aqueous sodium carbonate (0.410 mL, 0.82 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0)

(Biotage), 0.09 mmol/g loading, (167 mg, 0.015 mmol)] was added. The reaction vessel was sealed and was heated by microwave irradiation at 100° C. for 75 minutes. The reaction mixture was cooled to room temperature, diluted with dichloromethane and saturated aqueous sodium carbonate, and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-heptane, 40 to 100%) to afford 4-chloro-1-methyl-5-pyridin-3-yl-1,3-dihydro-indol-2-one; HRMS: (ESI) m/z 259.0636 (M+H)$^+$; $^1$H NMR (400 MHz, CDCl$_3$) δ ppm 3.27 (s, 3H), 3.62 (s, 2H), 6.85 (d, J=8.1 Hz, 1H), 7.31 (d, J=8.1 Hz, 1H), 7.38-7.48 (m, 1H), 7.85 (d, J=7.8 Hz, 1H), 8.64 (dd, J=4.9, 1.6 Hz, 1H), 8.69 (d, J=2.3 Hz, 1H).

Example 27 a) 4-Chloro-1-methyl-5-(4,4,5,5-tetramethyl-[1,3,2]dioxaborolan-2-yl)-1,3-dihydro-indol-2-one

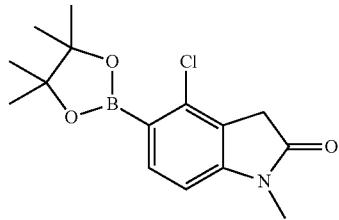 [SMILES: CN1C(=O)Cc2c1ccc(B1OC(C)(C)C(C)(C)O1)c2Cl]

To a solution of 5-bromo-4-chloro-1-methyl-1,3-dihydro-indol-2-one (521 mg, 2.00 mmol), prepared as described in Example 26b, in DMSO (8 mL) was added bis(pinacolato)diboron (559 mg, 2.2 mmol), and potassium acetate (589 mg, 6.0 mmol). Next [1,1'-bis(diphenylphosphino)-ferrocene]-dichloropalladium(II) complexed with dichloromethane (CAS#72287-26-4, 65 mg, 0.08 mmol) was added. The reaction mixture was degassed by bubbling argon through the solution for 3 minutes. The reaction was then heated at 80° C. for 20 hr. The reaction was then poured into ice-water and extracted three times with diethyl ether. The organic extracts were combined, washed with brine, dried over anhydrous sodium sulfate, filtered and concentrated. The re-suiting residue was purified by silica gel flash chromatography (ethanol-dichloromethane, 0 to 2%) to afford 4-chloro-1-methyl-5-(4,4,5,5-tetramethyl-[1,3,2]dioxaborolan-2-yl)-1,3-dihydro-indol-2-one; MS: (ES+) m/z 308.2 (M+H)$^+$.

b) 4-Chloro-5-(5-ethoxy-pyridin-3-yl)-1-methyl-1,3-dihydro-indol-2-one

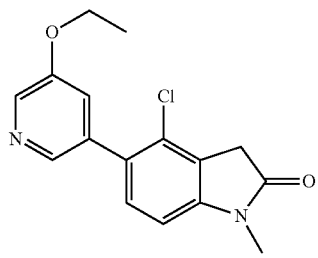 [SMILES: CCOc1cncc(-c2ccc3c(c2Cl)CC(=O)N3C)c1]

To 4-chloro-1-methyl-5-(4,4,5,5-tetramethyl-[1,3,2]dioxaborolan-2-yl)-1,3-dihydro-indol-2-one (95 mg, 0.31 mmol) was added 3-bromo-5-ethoxy-pyridine (CAS#17117-17-8, 69 mg, 0.34 mmol), 1,2-dimethoxyethane (3.0 mL), and 2 M aqueous sodium carbonate (0.390 mL, 0.77 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (140 mg, 0.015 mmol)] was added. The reaction vessel was sealed and was heated by microwave irradiation at 115° C. for 3 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 3%) to furnish 4-chloro-5-(5-ethoxy-pyridin-3-yl)-1-methyl-1,3-dihydro-indol-2-one; HRMS: (ESI) m/z 303.0901 (M+H)$^1$; $^1$H NMR (400 MHz, CDCl$_3$) δ ppm 1.48 (t, J=6.9 Hz, 3H), 3.26 (a, 3H), 3.61 (a, 2H), 4.15 (q, J=6.9 Hz, 2H), 6.84 (d, J=8.1 Hz, 1H), 7.28-7.33 (m, 2H), 8.26 (d, J=1.8 Hz, 1H), 8.32 (d, J=2.8 Hz, 1H).

Example 28

5-(5-Bromo-pyridin-3-yl)-4-chloro-1-methyl-1,3-dihydro-indol-2-one

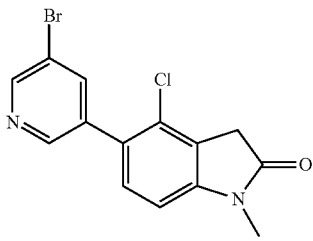

To 4-chloro-1-methyl-5-(4,4,5,5-tetramethyl-[1,3,2]dioxaborolan-2-yl)-1,3-dihydro-indol-2-one (525 mg, 1.71 mmol), prepared as described in Example 27a, was added 3,5-dibromopyridine (CAS#625-92-3, 1.2 g, 5.1 mmol), 1,2-dimethoxyethane (5.0 mL), and 2 M aqueous sodium carbonate (2.05 mL, 4.1 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (0.93 g, 0.10 mmol)] was added. The reaction vessel was sealed and was heated by microwave irradiation at 120° C. for 3.5 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 3.55%) to furnish 5-(5-bromo-pyridin-3-yl)-4-chloro-1-methyl-1,3-dihydro-indol-2-one; HRMS: (ESI) m/z 336.9753 (M+H)$^+$; $^1$H NMR (400 MHz, CDCl$_3$) δ ppm 3.27 (a, 3H), 3.62 (s, 2H), 6.85 (d, J=8.1 Hz, 1H), 7.30 (d, J=8.0 Hz, 1H), 7.95-8.04 (m, 1H), 8.61 (d, J=1.8 Hz, 1H), 8.70 (d, J=2.3 Hz, 1H).

Example 29

5-(5-Amino-pyridin-3-0)-4-chloro-1-methyl-1,3-dihydro-indol-2-one

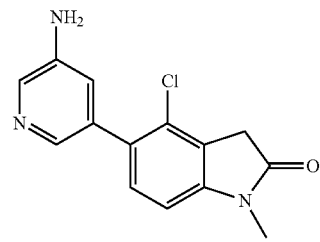

To 4-chloro-1-methyl-5-(4,4,65-tetramethyl-[1,3,2]dioxaborolan-2-yl)-1,3-dihydro-indol-2-one, prepared as described in Example 27a, (85 mg, 0.276 mmol) was added 3-amino-5-bromopyridine (CAS#13535-01-8, 53 mg, 0.304 mmol), tripotassium phosphate (147 mg, 0.691 mmol) and DMF (2.5 mL). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (126 mg, 0.014 mmol)] was added. The reaction vessel was sealed and was heated by microwave irradiation at 115° C. for 75 minutes. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 5%) to furnish 5-(5-amino-pyridin-3-yl)-4-chloro-1-methyl-1,3-dihydro-indol-2-one; HRMS: (ESI) m/z 274.0742 (M+H)$^+$; $^1$H NMR (400 MHz, CDCl$_3$) δ ppm 3.26 (s, 3H), 3.60 (s, 2H), 3.88 (br. s., 2H), 6.82 (d, J=7.8 Hz, 1H), 7.10 (br. s., 1H), 7.29 (d, J=8.1 Hz, 1H), 8.07 (d, J=1.5 Hz, 1H), 8.15 (br. s., 1H).

Example 30 a) 3-Bromo-5-vinyl-pyridine

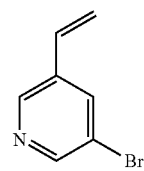

To a solution of methyltriphenylphosphonium bromide (2.97 g, 8.33 mmol) in THF (45 ml) at −78° C. was added n-butyllithium (2.5 M in hexanes, 2.7 mL, 6.75 mmol). The resulting yellow reaction mixture was stirred for 30 min at −78° C. In a separate flask THF (9 mL) was added to 5-bromonicotinaldehyde (CAS#113118-81-3, 837 mg, 4.5 mmol). The resulting 5-bromonicotinaldehyde solution was then transferred, via cannula, to the phosphonium ylide mixture followed by a 2 mL THF wash. The reaction was allowed to warm to room temperature over 120 minutes and then permitted to stir for an additional 30 minutes. The reaction was then quenched with saturated aqueous sodium bicarbonate and diluted with ethyl acetate. The layers were separated and the organic layer was washed with saturated aqueous sodium bicarbonate. The organic layer was concentrated to near dryness and the resulting residue was then diluted with ethyl acetate and 1M sodium bisulfate and the layers were separated. The organic layer was extracted two additional times with 1M sodium bisulfate. The aqueous layers were combined, diluted with dichloromethane, and neutralized via the careful addition of saturated aqueous sodium bicarbonate and solid sodium carbonate. The layers were separated and the now basic aqueous layer was extracted three additional times with dichloromethane. The dichloromethane layers were combined, dried over anhydrous sodium sulfate, filtered and concentrated. The resulting residue was purified by silica gel flash chromatography (ethyl acetate-dichloromethane, 0 to 16%) to furnish 3-bromo-4-vinyl-pyridine; MS: (ES+) m/z 183.9 (M+H)$^+$ b) 4-Chloro-1-methyl-5-(5-vinyl-pyridin-3-yl)-1,3-dihydro-indol-2-one

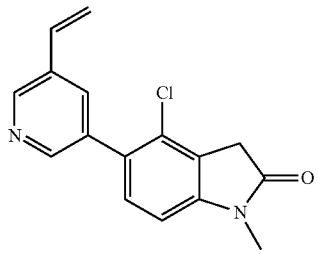 [SMILES: C=Cc1cncc(-c2ccc3c(c2Cl)CC(=O)N3C)c1]

The above compound was prepared in a similar fashion as described in Example 27; MS (ES+) m/z 285.0 (M+H)$^+$ c) 4-Chloro-5-(5-ethyl-pyridin-3-yl)-1-methyl-1,3-dihydro-indol-2-one

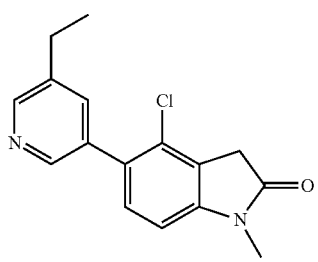 [SMILES: CCc1cncc(-c2ccc3c(c2Cl)CC(=O)N3C)c1]

To a solution of 4-chloro-1-methyl-5-(5-vinyl-pyridin-3-yl)-1,3-dihydro-indol-2-one (70 mg, 0.246 mmol) in ethanol (5 mL) was added 10% palladium on carbon (39 mg, 0.037 mmol). The atmosphere over the reaction mixture was evacuated and the reaction was placed under an atmosphere of hydrogen gas via a balloon. The reaction was stirred for 25 minutes. The reaction mixture was then filtered through a plug of Celite® and the filtrate was then concentrated to dryness. The resulting residue was purified by silica gel flash chromatography (ethanol-dichloromethane, 0 to 5%) to afford 4-chloro-5-(5-ethyl-pyridin-3-yl)-1-methyl-1,3-dihydro-indol-2-one. HRMS: (ESI) m/z 287.0946 (M+H)$^+$; $^1$H NMR (400 MHz, CDCl$_3$) δ ppm 1.33 (t, J=7.6 Hz, 3H), 2.76 (q, J=7.6 Hz, 2H), 3.27 (s 3H), 3.61 (s, 2H), 6.85 (d, J=8.0 Hz, 1H), 7.30 (d, J=8.0 Hz, 1H), 7.68 (s, 1H), 8.45-8.57 (m, 2H).

Example 31

4-Chloro-5-(5-cyclopropyl-pyridin-3-yl)-1-methyl-1,3-dihydro-indol-2-one

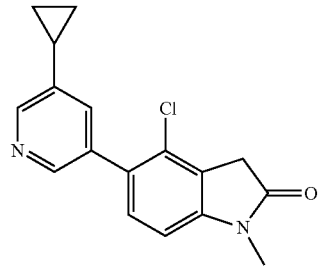 [SMILES: CN1C(=O)Cc2c1ccc(-c1cncc(C3CC3)c1)c2Cl]

To 5-(5-bromo-pyridin-3-yl)-4-chloro-1-methyl-1,3-dihydro-indol-2-one prepared as described in Example 28, (85 mg, 0.25 mmol) was added potassium cyclopropyltrifluoroborate (41 mg, 0.38 mmol), THF (2 mL) water, (0.66 mL), and tripotassium phosphate (187 mg, 0.88 mmol). The reaction mixture was degassed and placed under an argon atmosphere, and then (1,1'-bis(diphenylphosphino)-ferrocenel-dichloropalladium(II) complexed with dichloromethane (CAS#72287-26-4 10.3 mg, 0.013 mmol) was added. The reaction vessel was sealed and was heated by microwave irradiation at 125° C. for 4 h. The reaction mixture was cooled to room temperature and diluted with dichloromethane and saturated aqueous sodium bicarbonate and the layers were separated. The aqueous layer was extracted two times with dichloromethane, and the organic layers were combined, dried over anhydrous sodium sulfate, filtered through a pad of Celite®, and concentrated. The resulting residue was purified by silica gel flash chromatography (ethyl acetate-dichloromethane, 0 to 100%) to afford 4-chloro-5-(5-cyclopropyl-pyridin-3-yl)-1-methyl-1,3-dihydro-indol-2-one; HRMS: (ESI) m/z 299.0955 (M+H)$^+$; $^1$H NMR (400 MHz, CDCl$_3$) δ ppm 0.78-0.82 (m, 2H), 1.01-1.18 (m, 2H), 1.94-2.04 (m, 1H), 3.26 (s, 3H), 3.61 (s, 2H), 6.83 (d, J=7.8 Hz, 1H), 7.26-7.31 (m, 1H), 7.44 (br. s., 1H), 8.36-8.54 (m, 2H).

Example 32

5-[3,3']Bipyridinyl-5-yl-4-chloro-1-methyl-1,3-dihydro-indol-2-one

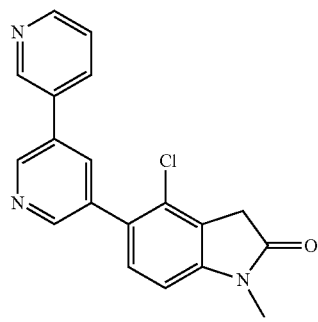 [SMILES: CN1C(=O)Cc2c1ccc(-c1cncc(-c3cccnc3)c1)c2Cl]

To 5-(5-bromo-pyridin-3-yl)-4-chloro-1-methyl-1,3-dihydro-indol-2-one prepared as described in Example 28, (100 mg, 0.30 mmol) was added 3-pyridine boronic acid (CAS#1692-25-7, 47.3 mg, 0.385 mmol), 1,2-dimethoxyethane (3 mL), and 2 M aqueous sodium carbonate (0.385 mL, 0.770 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (135 mg, 0.015 mmol)] was added. The reaction vessel was sealed and was heated by microwave irradiation at 120° C. for 2.5 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 1 to 8%) to furnish 5-[3,3']bipyridinyl-5-yl-1-methyl-1,3-dihydro-indol-2-one; HRMS: (ESI) m/z 336.0905 (M+H)$^+$; $^1$H NMR (400 MHz, DMSO-d$_6$) δ ppm 3.18 (s, 3H), 3.68 (s, 2H), 7.15 (d, J=8.1 Hz, 1H), 7.50-7.60 (m, 2H), 8.20 (t, J=2.1 Hz, 1H), 8.21-8.27 (m, 1H), 8.65 (dd, J=4.7, 1.6 Hz, 1H), 8.68 (d, J=2.0 Hz, 1H), 8.97 (d, J=2.1 Hz, 1H), 9.03 (d, J=2.4 Hz, 1H).

Example 33 a) 1,4-Dimethyl-1H-indole

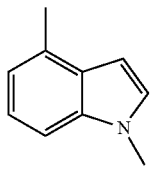

To a solution of 4-methyl-1H-indole (CAS#16096-32-5, 2.82 mL, 22.9 mmol) in THF (100 mL) at 0° C. was added sodium hydride (60% dispersion in oil, 1.37 g, 34.3 mmol). The reaction was permitted to stir for 16 minutes at 0° C. and was then warmed to room temperature for 60 minutes. The reaction mixture was then re-cooled to 0° C. and iodomethane (1.86 mL, 29.7 mmol) was added. The reaction was then put at room temperature and permitted to stir for 45 minutes. The reaction was then quenched with saturated aqueous ammonium chloride and concentrated to approximately half of its original volume. The mixture was then diluted with water and dichloromethane and the layers were separated. The aqueous layer was then extracted two additional times with dichloromethane. The organic layers were combined, dried over anhydrous sodium sulfate, filtered and concentrated. The resulting residue was purified by silica gel flash chromatography (ethyl acetate-heptane 0 to 30%) to afford 1,4-dimethyl-1H-indole; $^1$H NMR (400 MHz, CDCl$_3$) δ ppm 2.57 (s, 3H), 3.80 (s 3H), 6.51 (d, J=3.0 Hz, 1H), 6.93 (d, J=6.7 Hz, 1H), 7.06 (d, J=3.0 Hz, 1H), 7.13-7.21 (m, 2H).

b) 5-Bromo-1,4-dimethyl-1,3-dihydro-indol-2-one

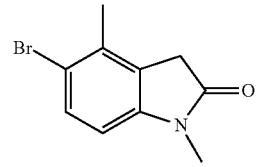

To a solution of 1,4-dimethyl-1H-indole, (200 mg, 1.38 mmol) in tert-butanol (8 mL) was added water (4 mL) and the mixture was put at 50° C. In a separate flask was added potassium bromide (1.6 g, 13.8 mmol) followed by water (11 mL) and bromine (0.36 mL, 6.9 mmol). Next the bromine solution (8 was added dropwise to the 1,4-dimethyl-1H-indole mixture. After the addition was complete the temperature of the reaction was elevated to 70° C. for 30 min. The reaction was cooled to room temperature and diluted with dichloromethane and saturated aqueous sodium bicarbonate. The solution was then further diluted with saturated aqueous sodium thiosulfate. The layers were separated and the aqueous layer was extracted two additional times with dichloromethane. The organic extracts were combined, dried over anhydrous sodium sulfate, filtered and concentrated. The resulting solid was filtrated with diethyl ether and one half of the solid, by weight, was then dissolved in acetic acid (2.5 Zinc dust (62 mg, 0.94 mmol) was then added. After 10 minutes the reaction mixture was filtered through a pad of Celite® and diluted with dichloromethane. The resulting solution was cooled to 0° C. and neutralized via the cautious addition of 2 N aqueous sodium hydroxide and saturated aqueous sodium bicarbonate. The resulting layers were separated and the aqueous layer was extracted two additional times with dichloromethane. The combined organic layers were dried over anhydrous sodium sulfate, filtered and concentrated. The resulting residue was purified by silica gel flash chromatography (ethyl acetate-heptane 15 to 80%) to afford 5-bromo-1,4-dimethyl-1,3-dihydro-indol-2-one; $^1$H NMR (400 MHz, CDCl$_3$) δ ppm 2.32 (s, 3H), 3.19 (s, 3H), 3.47 (s, 2H), 6.56 (d, J=8.1 Hz, 1H), 7.48 (d, J=8.1 Hz, 1H).

c) 1,4-Dimethyl-5-pyridin-3-yl-1,3-dihydro-indol-2-one

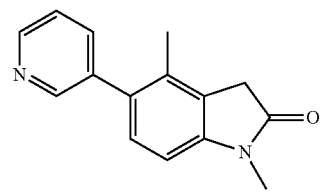 [SMILES: Cc1c(-c2cccnc2)ccc2c1CC(=O)N2C]

To 1,4-dimethyl-5-pyridin-3-yl-1,3-dihydro-indol-2-one (85 mg, 0.35 mmol) was added 3-pyridineboronic acid (CAS#1692-25-7, 52 mg, 0.43 mmol), 1,2-dimethoxyethane (3 mL), and 2 M aqueous sodium carbonate (0.44 mL, 0.89 mmol). The reaction mixture was degassed and placed under an argon atmosphere, at which time resin bound tetrakis (triphenylphosphine)palladium(0), specifically polystyrene triphenylphosphine palladium (0) [PS—PPh$_3$-Pd(0) (Biotage), 0.11 mmol/g loading, (161 mg, 0.018 mmol)] was added. The reaction vessel was sealed and was heated by microwave irradiation at 120° C. for 2 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-dichloromethane, 15 to 100%) to afford 1,4-dimethyl-5-pyridin-3-yl-1,3-dihydro-indol-2-one; HRMS: (ESI) m/z 239.1183 (M+H)$^+$; $^1$H NMR (400 MHz, CDCl$_3$) δ ppm 2.20 (s, 3H), 3.26 (s, 3H), 3.50 (s, 2H), 6.79 (d, J=8.1 Hz, 1H), 7.19 (d, J=7.8 Hz, 1H), 7.34-7.51 (m, 1H), 7.71-7.73 (m, 1H), 8.54-8.69 (m, 2H).

Example 34 a) 1,4-Dimethyl-5-(4,4,5,5-tetramethyl-[1,3,2]dioxaborolan-2-yl)-1,3-dihydro-indol-2-one

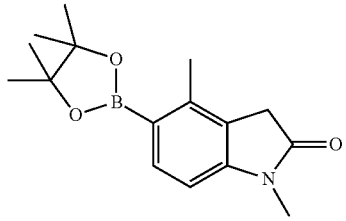 [SMILES: Cc1c(B2OC(C)(C)C(C)(C)O2)ccc2c1CC(=O)N2C]

To a solution of 5-bromo-1,4-dimethyl-1,3-dihydro-indol-2-one, prepared as described in Example 33b, (550 mg, 2.3 mmol), in DMSO (9.5 mL) was added bis(pinacolato)diboron (640 mg, 2.5 mmol), and potassium acetate (674 mg, 6.9 mmol). Next [1,1'-bis(diphenylphosphino)-ferrocene]-dichloropalladium(II) complexed with dichloromethane (CAS#72287-26-4, 94 mg, 0.115 mmol) was added. The reaction mixture was degassed by bubbling argon through the solution for 3 minutes. The reaction was then heated at 85° C. for 14.5 hr. The reaction was then cooled to room temperature, diluted with diethyl ether and filtered through Celite®. The filtrate was then diluted with water and the layers were separated. The aqueous layer was extracted two additional times with diethyl ether. The organic extracts were combined, washed with brine, dried over anhydrous magnesium sulfate, filtered and concentrated. The resulting residue was purified by silica gel flash chromatography (ethyl acetate-dichloromethane, 0 to 5%) to afford 1,4-dimethyl-5-(4,4,5,5-tetramethyl-[1,3,2]dioxaborolan-2-yl)-1,3-dihydro-indol-2-one; MS: (ES+) m/z 288.3 (M+H)$^+$.

b) 5-(5-Hydroxymethyl-pyridin-3-0)-1,4-dimethyl-1,3-dihydro-indol-2-one

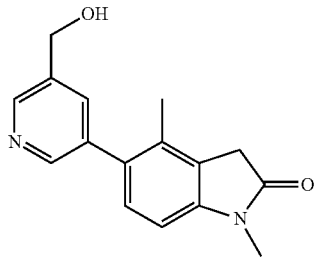 [SMILES: Cc1c(-c2cncc(CO)c2)ccc2c1CC(=O)N2C]

To 1,4-dimethyl-5-(4,4,5,5-tetramethyl-[1,3,2]dioxaborolan-2-yl)-1,3-dihydro-indol-2-one (85 mg, 0.30 mmol) was added (5-bromo-pyridin-3-yl)-methanal (CAS#37669-64-0, 61 mg, 0.33 mmol), 1,2-dimethoxyethane (3.0 mL), and 2 M aqueous sodium carbonate (0.370 mL, 0.74 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (135 mg, 0.015 mmol)] was added. The reaction vessel was sealed and was heated by microwave irradiation at 120° C. for 3 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was partially purified by silica gel flash chromatography (ethanol-dichloromethane, 0 to 7.5%). Further purification was accomplished via reverse phase HPLC (10 to 40% acetonitrile/Water w/0.1% NH$_4$OH) to furnish 5-(5-hydroxymethyl-pyridin-3-yl)-1,4-dimethyl-1,3-dihydro-indol-2-one; HRMS: (ESI) m/z 269.1288 (M+H)$^+$; $^1$H NMR (400 MHz, DMSO-d$_6$) δ ppm 2.14 (s, 3H), 3.15 (s, 3H), 3.56 (s, 2H), 4.60 (s, 2H), 5.35 (br. s., 1H), 6.93 (d, J=7.8 Hz, 1H), 7.18 (d, J=8.1 Hz, 1H), 7.65 (t, J=2.1 Hz, 1H), 8.40 (d, J=2.3 Hz, 1H), 8.50 (d, J=2.0 Hz, 1H).

Example 35

5-(5-Bromo-pyridin-4-yl)-1,4-dimethyl-1,3-dihydro-indol-2-one

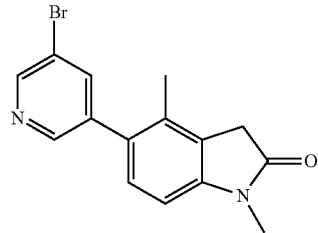 [SMILES: Cc1c(-c2cncc(Br)c2)ccc2c1CC(=O)N2C]

To 1,4-dimethyl-5-(4,4,5,5-tetramethyl-[1,3,2]dioxaborolan-2-yl)-1,3-dihydro-indol-2-one, prepared as described in Example 34a (90 mg, 0.31 mmol) was added 3,5-dibromopyridine (CAS#625-92-3, 223 mg, 0.940 mmol), 1,2-dimethoxyethane (3.0 mL), and 2 M aqueous sodium carbonate (0.376 mL, 0.75 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (171 mg, 0.019 mmol)] was added. The reaction vessel was sealed and was heated by microwave irradiation at 120° C. for 2 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-dichloromethane, 0 to 65%) to furnish 5-(5-bromo-pyridin-3-yl)-1,4-dimethyl-1,3-dihydro-indol-2-one; HRMS: (ESI) m/z 317.0289 (M+H)$^+$; $^1$H NMR (400 MHz, CDCl$_3$) δ ppm 210 (s, 3H), 3.26 (s, 3H), 3.50 (s, 2H), 6.78 (d, J=8.0 Hz, 1H), 7.17 (d, J=8.0 Hz, 1H), 7.82 (t, J=2.0 Hz, 1H), 8.50 (d, J=1.8 Hz, 1H), 8.68 (d, J=2.1 Hz, 1H).

Example 36 a) 4-Methoxy-1-methyl-1H-indole

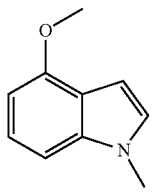

To a solution of 4-methoxy-1H-indole (CAS#4837-90-5, 4.0 g, 27.2 mmol) in THF (100 ml) at 0° C. was added sodium hydride (60% dispersion in oil, 1.63 g, 40.08 mmol). The reaction was stirred for 15 minutes at 0° C. and then put at room temperature for 1 h. The reaction was then re-cooled to 0° C. and iodomethane (2.209 ml, 35.3 mmol) was added. The reaction was then put at room temperature and permitted to stir for 45 minutes. The reaction was then quenched with saturated aqueous ammonium chloride and concentrated to approximately half of its original volume. Next, the reaction mixture was diluted with water and dichloromethane and the layers were separated. The aqueous layer was then extracted two additional times with dichloromethane. The organic layers were combined, dried over anhydrous sodium sulfate, filtered and concentrated. The resulting residue was purified by silica gel flash chromatography (ethyl acetate-heptane 0 to 30%) to afford 4-methoxy-1-methyl-1H-indole; MS: (ES+) m/z 162.0 (M+H)$^+$.

b) 4-Methoxy-1-methyl-1,3-dihydro-indol-2-one

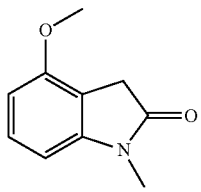

To a solution of potassium bromide (3986 mg, 33.5 mmol) in water (26.5 ml) was added bromine (0.863 ml, 16.75 mmol). A separate flask containing 4-methoxy-1-methyl-1H-indole (900 mg, 5.58 mmol) was charged with t-butanol (20.00 ml) and water (20.0 ml). To this flask was added 22.5 mL of bromine solution dropwise. The mixture was permitted to stir for approximately 30 minutes and then was neutralized with saturated aqueous sodium bicarbonate and quenched with saturated aqueous sodium thiosulfate. The reaction was then diluted with dichloromethane and saturated aqueous sodium bicarbonate and the layers were separated. The aqueous layer was extracted two additional times with dichloromethane and the organic layers were combined, dried over anhydrous sodium sulfate, filtered, and concentrated. The resulting residue was dissolved in 50 mL EtOH and 5 mL of AcOH. The solution was then charged with 10% palladium on carbon (1.2 g, 1.13 mmol). The atmosphere over the reaction mixture was evacuated and the reaction was placed under an atmosphere of hydrogen gas via a balloon. The reaction was stirred for 18 hours. The reaction mixture was then filtered through a plug of Celite® and the filtrate was then concentrated to approximately 25% of its original volume. The reaction was then diluted with dichloromethane and saturated aqueous sodium bicarbonate and the layers were separated. The aqueous layer was extracted two additional times with dichloromethane and the organic layers were combined, dried over anhydrous sodium sulfate, filtered, and concentrated. The resulting residue was purified by silica gel flash chromatography (ethyl acetate-heptane, 0 to 60%) to afford 4-methoxy-1-methyl-1,3-dihydro-indol-2-one; MS: (ES+) m/z 178.0 (M+H)$^+$.

c) 5-Bromo-4-methoxy-1-methyl-1,3-dihydro-indol-2-one

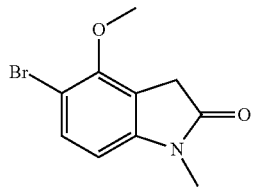

To a solution of 4-methoxy-1-methyl-1,3-dihydro-indol-2-one (440 mg, 2.483 mmol) in chloroform (25 ml) was added methanol (25.00 ml). The reaction was put at −10° C. and N-bromosuccinimide (442 mg, 2.483 mmol) was added in three portions over a 30 min interval and the reaction was then stirred for 10 minutes. The reaction was then diluted with dichloromethane, saturated aqueous sodium bicarbonate, and saturated aqueous sodium thiosulfate and the layers were separated. The aqueous layer was extracted two additional times with dichloromethane and the organic layers were combined, dried over anhydrous sodium sulfate, filtered, and concentrated. The resulting residue was purified by silica gel flash chromatography (ethyl acetate-heptane, 0 to 60%) to afford 5-bromo-4-methoxy-1-methyl-1,3-dihydro-indol-2-one; MS: (ES+) m/z 255.8 (M+H)$^+$.

d) 4-Methoxy-1-methyl-5-pyridin-3-yl-1,3-dihydro-indol-2-one

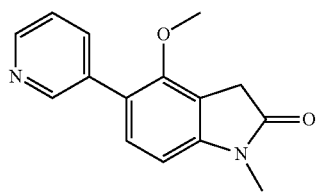 [SMILES: COc1c(-c2cccnc2)ccc2c1CC(=O)N2C]

To 5-bromo-4-methoxy-1-methyl-1,3-dihydro-indol-2-one (105 mg, 0.410 mmol) was added 3-pyridineboronic acid (CAS#1692-25-7, 60.5 mg, 0.492 mmol), 1,2-dimethoxyethane (3 mL) and 2 M aqueous sodium carbonate (0.513 ml, 1.025 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 mmol/g loading, (186 mg, 0.021 mmol)] was added. The reaction vessel was sealed and was heated by microwave irradiation at 120° C. for 2.25 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-dichloromethane, 20 to 100%) to afford 4-methoxy-1-methyl-5- pyridin-3-yl-1,3-dihydro-indol-2-one; HRMS: (ESI) m/z 255.1136 (M+H)+; 1H NMR (400 MHz, CO2Cl2) δ ppm 3.20 (s, 3H), 3.66 (s, 2H), 3.72 (s, 3H), 6.68 (d, J=8.0 Hz, 1H), 7.28 (d, J=8.0 Hz, 1H), 7.38 (dd, J=7.9, 4.9 Hz, 1H), 7.79-7.96 (m, 1H), 8.52 (d, J=4.0 Hz, 1H), 8.71 (s, 1H).

Example 37 a) 4-Methoxy-1-methyl-5-(4,4,5,5-tetramethyl-[1,3,2]dioxaborolan-2-yl)-1,3-dihydro-indol-2-one

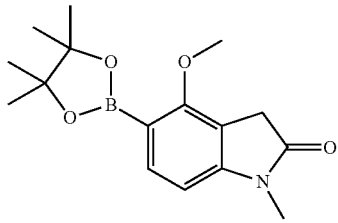 [SMILES: COc1c(B2OC(C)(C)C(C)(C)O2)ccc2c1CC(=O)N2C]

To a solution of 5-bromo-4-methoxy-1-methyl-1,3-dihydro-indol-2-one, prepared as described in Example 36c (480 mg, 1.87 mmol), in DMSO (8.5 mL) was added bis(pinacolato)diboron (524 mg, 2.06 mmol), and potassium acetate (552 mg, 6.62 mmol). Next [1,1'-bis(diphenylphosphino)-ferrocene]-dichloropalladium(II) complexed with dichloromethane (CAS#72287-26-4, 77 mg, 0.094 mmol) was added. The reaction mixture was degassed by bubbling argon through the solution for 3 minutes. The reaction was then heated at 85° C. for 14.5 hr. The reaction was then cooled to room temperature, diluted with diethyl ether and filtered through Celite®. The filtrate was then diluted with water and the layers were separated. The aqueous layer was extracted two additional times with diethyl ether. The organic extracts were combined, washed with saturated aqueous sodium bicarbonate, dried over anhydrous magnesium sulfate, filtered and concentrated. The resulting residue was purified by silica gel flash chromatography (ethyl acetate-dichloromethane, 0 to 15%) to afford 4-methoxy-1-methyl-5-(4,4,5,5-tetramethyl-[1,3,2]dioxaborolan-2-yl)-1,3-dihydro-indol-2-one; MS: (ES+) m/z 304.0 (M+H)+.

b) 5-(5-Bromo-pyridin-3-yl)-4-methoxy-1-methyl-1,3-dihydro-indol-2-one

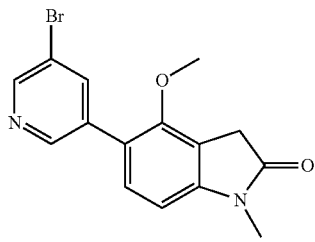 [SMILES: COc1c(-c2cncc(Br)c2)ccc2c1CC(=O)N2C]

To 4-methoxy-1-methyl-5-(4,4,5,5-tetramethyl-[1,3,2]dioxaborolan-2-yl)-1,3-dihydro-indol-2-one (80 mg, 0.264 mmol) was added 3,5-dibromopyridine (CAS#625-92-3, 188 mg, 0.792 mmol), 1,2-dimethoxyethane (3.0 mL), and 2 M aqueous sodium carbonate (0.320 mL, 0.63 mmol). The reaction mixture was degassed and placed under an argon atmosphere, at which time resin bound tetrakis(triphenylphosphine)palladium(0), specifically polystyrene triphenylphosphine palladium (0) [PS—PPh3-Pd(0) (Biotage), 0.11 mmol/g loading, (144 mg, 0.016 mmol)] was added. The reaction vessel was sealed and was heated by microwave irradiation at 120° C. for 2 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-dichloromethane, 10 to 75%) to furnish 5-(5-bromo-pyridin-3-yl)-4-methoxy-1-methyl-1,3-dihydro-indol-2-one; HRMS: (ESI) tilt 333.0246 (M+H)+; 1H NMR (400 MHz, CDCl3) δ ppm 3.24 (s, 3H), 3.75 (s, 3H), 3.78 (s, 2H), 4.71 (s, 2H), 6.84 (d, J=8.1 Hz, 1H), 7.34 (d, J=8.1 Hz, 1H), 7.94 (d, J=2.0 Hz, 1H), 8.45 (d, J=1.8 Hz, 1H), 8.55 (d, J=2.0 Hz, 1H)

Example 38

5-(5-Hydroxymethyl-pyridin-3-0)-4-methoxy-1-ethyl-1,3-dihydro-indol-1-one

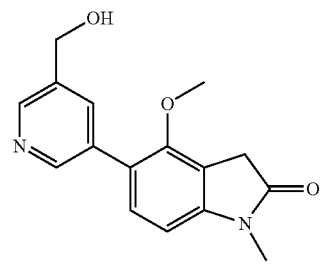 [SMILES: COc1c(-c2cncc(CO)c2)ccc2c1CC(=O)N2C]

To 4-methoxy-1-methyl-5-(4,4,5,5-tetramethyl-[1,3,2]dioxaborolan-2-yl)-1,3-dihydro-indol-2-one, prepared as described in Example 37a (80 mg, 0.264 mmol) was added (5-bromo-pyridin-3-yl)-methanol (CAS#37669-64-0, 55 mg, 0.29 mmol), 1,2-dimethoxyethane (3.0 mL), and 2 M aqueous sodium carbonate (0.330 mL, 066 mmol). The reaction mixture was degassed and placed under an argon atmosphere, at which time resin bound tetrakis(triphenylphosphine)palladium(0), specifically polystyrene triphenylphosphine palladium (0) [PS—PPh3-Pd(0) (Biotage), 0.11 mmol/g loading, (120 mg, 0.013 mmol)] was added. The reaction vessel was sealed and was heated by microwave irradiation at 120° C. for 3 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was partially purified by silica gel flash chromatography (ethanol-dichloromethane, 0 to 10%). Further purification was accomplished via reverse phase HPLC (7 to 40% acetonitrile/water w/0.1% NH4OH) to furnish 5-(5-hydroxymethyl-pyridin-3-yl)-4-methoxy-1-methyl-1,3-dihydro-indol-2-one; HRMS: (ESI) m/z 285.1240 (M+H)+; 1H NMR (400 MHz, CD3OD) δ ppm 3.24 (s, 3H), 3.75 (s, 3H), 3.78 (s, 2H), 4.71 (s, 2H), 6.84 (d, J=81 Hz, 1H), 7.34 (d, J=8.1 Hz, 1H), 7.94 (d, J=2.0 Hz, 1H), 8.45 (d, J=1.8 Hz, 1H), 8.55 (d, J=2.0 Hz, 1H)

Example 39 a) 6-Bromo-1-methyl-1,3-dihydro-indol-2-one

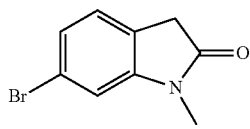

To a solution of 6-bromoisatin (CAS#6326-79-0, 4.52 g, 20.0 mmol) in acetonitrile (150 mL) was added potassium carbonate (11.1 g, 80 mmol) followed by iodomethane (2.75 mL, 44.0 mind). The reaction was then placed at 60° C. and stirred for 40 minutes. The reaction was then cooled to room temperature, filtered and concentrated to 10% of the original volume. The reaction was then diluted with dichloromethane, water, and brine. The layers were separated and the aqueous layer was extracted two additional times with dichloromethane. The organic extracts were combined, dried over anhydrous sodium sulfate filtered and concentrated to provide 6-bromo-1-methyl-1H-indole-2,3-dione as an orange solid without the need for further purification. The 6-bromo-1-methyl-1H-indole-2,3-dione (1.0 g, 4.2 mmol) was then treated with hydrazine hydrate (7.0 mL, 225 mmol). The reaction was heated to 130° C. and stirred for 80 minutes, at which time the reaction was placed at room temperature and cooled by the addition of ice. Once the reaction was cooled to room temperature it was diluted with dichloromethane and water and the layers were separated. The aqueous layer was extracted an additional two times with dichloromethane, and the organic layers were combined, dried over anhydrous sodium sulfate, filtered and concentrated. The resulting residue was purified by silica gel flash chromatography (ethanol-dichloromethane 0 to 2%) to afford 6-bromo-1-methyl-1,3-dihydro-indol-2-one; MS: (ES+) m/z 225.9 (M+H)+.

b) 1-Methyl-2-oxo-2,3-dihydro-1H-indole-6-carbonitrile

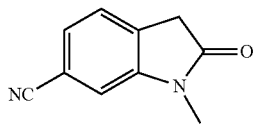

To a solution of 6-bromo-1-methyl-1,3-dihydro-indol-2-one (226 mg, 1.0 mmol) in DMF (6.0 mL) was added zinc cyanide (117 mg, 1.0 mmol). Then the reaction mixture was degassed and placed under an argon atmosphere and tetrakis(triphenylphosphine)palladium(0) (115 mg, 0.1 mmol) was added. The reaction was then placed at 95° C. for 100 minutes, at which time it was cooled to room temperature, and diluted with saturated aqueous sodium bicarbonate and dichloromethane. The layers were separated and the aqueous layer was extracted two additional times with dichloromethane. The organic layers were combined, dried over anhydrous sodium sulfate, filtered and concentrated. The resulting residue was purified by silica gel flash chromatography (ethanol-dichloromethane 0 to 4%) to furnish 1-methyl-2-oxo-2,3-dihydro-1H-indole-6-carbonitrile; MS: (ES+) m/z 173.0 (M+H)+.

c) 5-Bromo-1-methyl-2-oxo-2,3-dihydro-1H-indole-6-carbonitrile

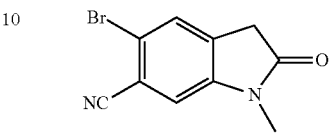

Water (9 mL) was added to 1-methyl-2-oxo-2,3-dihydro-1H-indole-6-carbonitrile (110 mg 0.64 mmol) and the resulting mixture was placed at 70° C. In a separate flask potassium bromide (462 g, 0.26 mmol) in water (12 mL) was treated with bromine (0.100 mL, 1.94 mmol). 6.0 mL of the orange bromine solution was added dropwise to the water and 1-methyl-2-oxo-2,3-dihydro-1H-indole-6-carbonitrile mixture over ca. 20 minutes. The resulting heterogeneous mixture was permitted to stir at 70° C. for an additional 5 minutes and then cooled to room temperature. The reaction was then diluted with dichloromethane and saturated aqueous sodium bicarbonate. The solution was then further diluted with saturated aqueous sodium thiosulfate. The layers were separated and the aqueous layer was extracted two additional times with dichloromethane. The organic extracts were combined, dried over anhydrous sodium sulfate, filtered and concentrated. The resulting residue was purified by silica gel flash chromatography (ethanol-dichloromethane 0 to 3.5%) to provide 5-bromo-1-methyl-2-oxo-2,3-dihydro-1H-indole-6-carbonitrile; MS: (ES+) m/z 250.9 (M+H)+.

d) 1-Methyl-2-oxo-5-pyridin-3-yl-2,3-dihydro-1H-indole-6-carbonitrile

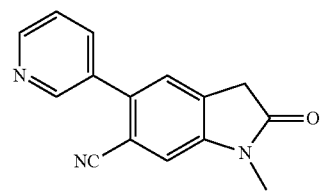 [SMILES: CN1C(=O)Cc2cc(-c3cccnc3)c(C#N)cc21]

To 5-bromo-1-methyl-2-oxo-2,3-dihydro-1H-indole-6-carbonitrile (58 mg, 0.23 mmol) was added 3-pyridine boronic acid (CAS#1692-25-7, 28 mg, 0.23 mmol), 1,2-dimethoxyethane (2.0 mL) and 2 M aqueous sodium carbonate (0.230 mL, 0.46 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.09 mmol/g loading, (105 mg, 0.009 mmol)] was added. The reaction vessel was sealed and was heated by microwave irradiation at 100° C. for 1.75 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethanol-dichloromethane, 0 to 6%) to afford 1-methyl-2-oxo-5-pyridin-3-yl-2,3-dihydro-1H-indole-6-carbonitrile; HRMS: (ESI) m/z 248.0838 (M–H)–; $^1$H NMR (400 MHz, CDCl$_3$) δ ppm 3.30 (s, 2H), 3.68 (s, 2H), 7.19 (s, 1H), 7.42 (s, 1H), 7.49-7.58 (m, 1H), 8.02 (d, J=7.6 Hz, 1H), 8.72 (dd, J=4.8, 1.1 Hz, 1H), 8.77 (d, J=1.8 Hz, 1H).

Example 40 a) 4-Cyclopropyl-1-methyl-1H-indole-2,3-dione

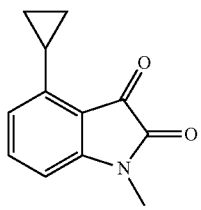

To a solution of 4-bromo-1-methyl-1,3-dihydro-indol-2-one, prepared in a fashion similar as described in Example 39a (CAS#884855-67-8, 1.80 g, 7.5 mmol) in THF (24 mL) was added water (8 mL), tripotassium phosphate (5.57 g, 26.3 mmol), and potassium cyclopropyltrifluoroborate (1.501 g, 10.50 mmol). The reaction mixture was degassed and placed under a nitrogen atmosphere, and then [1,1'-bis(diphenylphosphino)-ferrocene]-dichloropalladium(II) complexed with dichloromethane (CAS#72287-26-4 184 mg, 0.225 mmol) was added. The reaction vessel was sealed and was heated by microwave irradiation at 130° C. for 4 hours. The reaction mixture was then cooled to room temperature, diluted with ethyl acetate and brine and then filtered through a pad of Celite®. The layers of the filtrate were separated and the aqueous layer was extracted two times with ethyl acetate. The organic layers were combined, dried over anhydrous sodium sulfate, filtered and concentrated. The resulting residue was purified by silica gel flash chromatography (ethyl acetate-heptane, 0 to 100%) to furnish 4-cyclopropyl-1-methyl-1H-indole-2,3-dione; MS: (ES+) m/z 202.4 (M+H)$^+$.

b) 4-Cyclopropyl-1-methyl-1,3-dihydro-indol-2-one

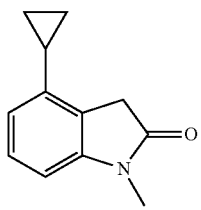

4-Cyclopropyl-1-methyl-1H-indole-2,3-dione (1.0 g, 4.2 mmol) was treated with hydrazine hydrate (7.0 mL, 225 mmol). The reaction was heated to 130° C. and stirred for 4 hours, at which time the reaction temperature was elevated to 150° C. for another 1.5 hours. The reaction was then placed at room temperature and cooled by the addition of ice. Once the reaction was cooled to room temperature it was diluted with dichloromethane and water and the layers were separated. The aqueous layer was extracted an additional two times with dichloromethane, and the organic layers were combined, dried over anhydrous sodium sulfate, filtered and concentrated. The resulting residue was purified by silica gel flash chromatography (ethyl acetate-heptane, 0 to 60%) to afford 4-cyclopropyl-1-methyl-1,3-dihydro-indol-2-one; MS: (ES+) ink 188.4 (M+H)$^+$.

c) 5-Bromo-4-cyclopropyl-1-methyl-1,3-dihydro-indol-2-one

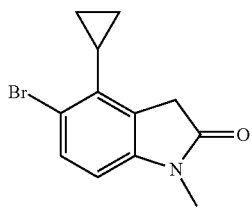

Water (14 mL) was added to 4-cyclopropyl-1-methyl-1,3-dihydro-indol-2-one (0.74 g, 3.94 mmol) and the resulting mixture was placed at 70° C. In a separate flask potassium bromide (1.03 g, 8.7 mmol) in water (14 was treated with bromine (0.225 mL, 4.3 mmol), the resulting orange solution was added dropwise to the 4-cyclopropyl-1-methyl-1,3-dihydro-indol-2-one mixture over ca. 10 minutes. The resulting heterogeneous mixture was permitted to stir at 70° C. for an additional hour and then cooled to room temperature. The reaction was then diluted with dichloromethane and saturated aqueous sodium bicarbonate. The solution was then further diluted with saturated aqueous sodium thiosulfate. The layers were separated and the aqueous layer eras extracted two additional times with dichloromethane. The organic extracts were combined, dried over anhydrous sodium sulfate, filtered and concentrated. The resulting residue was preadsorbed onto silica gel and purified by silica gel flash chromatography (ethyl acetate-heptane 0 to 50%) to provide 5-bromo-4-cyclopropyl-1-methyl-1,3-dihydro-indol-2-one; MS: (ES+) m/z 266.2 (M+H)$^+$.

d) 4-Cyclopropyl-1-methyl-5-(4,4,5,5-tetramethyl-[1,3,2]dioxaborolan-2-0)-1,3-dihydro-indol-2-one

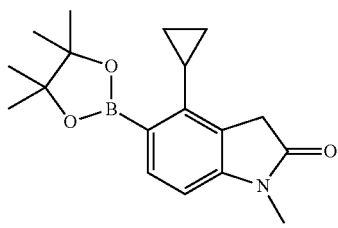 [SMILES: CN1C(=O)Cc2c1ccc(B1OC(C)(C)C(C)(C)O1)c2C1CC1]

To a solution of 5-bromo-4-cyclopropyl-1-methyl-1,3-dihydro-indol-2-one, (340 mg, 1.28 mmol), in DMSO (8. mL) was added bis(pinacolato)diboron (357 mg, 1.41 mmol), and potassium acetate (313 mg, 3.2 mmol). Next, [1,1'-bis(diphenylphosphino)-ferrocene]-dichloropalladium(II) complexed with dichloromethane (CAS#72287-26-4, 52 mg, 0.064 mmol) was added. The reaction mixture was degassed by bubbling nitrogen through the solution for 3 minutes. The reaction was then heated at 80° C. for 16 hr. The reaction was then cooled to room temperature, diluted with diethyl ether and filtered through Celite®. The filtrate was then diluted with water and the layers were separated. The aqueous layer was extracted two additional times with diethyl ether. The organic extracts were combined, washed with brine, dried over anhydrous magnesium sulfate, filtered and concentrated. The resulting residue was purified by silica gel flash chromatography (ethyl acetate-heptane, 0 to 70%) to afford 4-cyclopropyl-1-methyl-5-(4,4,5,5-tetramethyl-[1,3,2]dioxaborolan-2-yl)-1,3-dihydro-indol-2-one; MS: (ES+) m/z 314.0 (M+H)⁺.

e) 4-Cyclopropyl-5-(5-hydroxymethyl-pyridin-3-0)-1-methyl-1,3-dihydro-indol-2-one

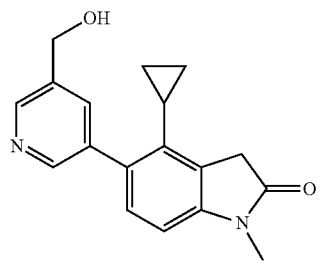 [SMILES: CN1C(=O)Cc2c1ccc(-c1cncc(CO)c1)c2C1CC1]

To 4-cyclopropyl-1-methyl-5-(4,4,5,5-tetramethyl-[1,3,2]dioxaborolan-2-yl)-1,3-dihydro-indol-2-one, (50 mg, 0.160 mmol) was added (5-bromo-pyridin-3-yl)-methanol (CAS#37669-64-0, 36 mg, 0.192 mmol), 1,2-dimethoxyethane (1.0 mL), and 2 M aqueous sodium carbonate (0.200 mL, 0.40 mmol). The reaction mixture was degassed and placed under an argon atmosphere, at which time resin bound tetrakis(triphenylphosphine)palladium(0), specifically polystyrene triphenylphosphine palladium (0) [PS—PPh₃-Pd(0) (Biotage), 0.11 mmol/g loading, (73 mg, 0.008 mmol)] was added. The reaction vessel was sealed and was heated by microwave irradiation at 130° C. for 1 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was partially purified by silica gel flash chromatography (ethanol-dichloromethane, 0 to 10%). Further purification was accomplished via reverse phase HPLC (10 to 40% acetonitrile/water w/0.1% NH₄OH) to furnish 4-Cyclopropyl-5-(5-hydroxymethyl-pyridin-3-yl)-1-methyl-1,3-dihydro-indol-2-one; HRMS: (ESI) m/z 295.14485 (M+H)+; ¹H NMR (400 MHz, CDCl₃) δ ppm 0.17-0.25 (m, 2H), 0.72-0.80 (m, 2H), 1.87-1.98 (m, 1H), 3.25 (s, 3H), 3.64 (s, 2H), 4.83 (s, 2H), 6.80 (d, J=7.8 Hz, 1H), 7.23 (d, J=7.8 Hz, 1H), 7.80 (t, J=2.0 Hz, 1H), 8.57 (d, J=1.8 Hz, 1H), 8.61 (d, J=2.0 Hz, 1H).

Example 41

5-(5-Bromo-pyridin-3-yl)-4-cyclopropyl-1-methyl-1,3-dihydro-indol-2-one

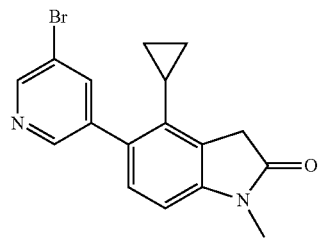 [SMILES: CN1C(=O)Cc2c1ccc(-c1cncc(Br)c1)c2C1CC1]

To 4-cyclopropyl-1-methyl-5-(4,4,5,5-tetramethyl-[1,3,2]dioxaborolan-2-yl)-1,3-dihydro-indol-2-one, prepared as described in Example 40d (50 mg, 0.16 mmol) was added 3,5-dibromopyridine (CAS#625-92-3, 113 mg, 0.479 mmol), 1,2-dimethoxyethane (1.5 mL), and 2 M aqueous sodium carbonate (0.2 mL, 0.4 mmol). The reaction mixture was degassed and placed under an argon atmosphere, at which time resin bound tetrakis(triphenylphosphine)palladium(0), specifically polystyrene triphenylphosphine palladium (0) [PS—PPh₃-Pd(0) (Biotage), 0.11 mmol/g loading, (43.5 mg, 4.79 μmol)] was added. The reaction vessel was sealed and was heated by microwave irradiation at 120° C. for 3 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-heptane, 10 to 75%) to furnish 5-(5-bromo-pyridin-3-yl)-4-cyclopropyl-1-methyl-1,3-dihydro-indol-2-one; HRMS: (ESI) m/z 343.0451 (M+H)⁺; ¹H NMR (400 MHz, CDCl₃) δ ppm 0.18-0.26 (m, 2H), 0.78-0.88 (m, 2H), 1.87-1.99 (m, 1H), 3.25 (s, 3H), 3.64 (s, 2H), 6.82 (d, J=8.0 Hz, 1H), 7.22 (d, J=8.0 Hz, 1H), 7.98 (s, 1H), 8.62 (d, J=1.4 Hz, 1H), 8.67 (d, J=2.0 Hz, 1H).

Example 42

4-Cyclopropyl-1-methyl-5-pyridin-3-yl-1,3-dihydro-indol-2-one

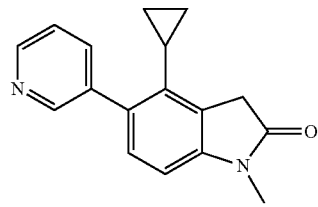 [SMILES: CN1C(=O)Cc2c1ccc(-c1cccnc1)c2C1CC1]

To 5-bromo-4-cyclopropyl-1-methyl-1,3-dihydro-indol-2-one, prepared as described in Example 40c, (320 mg, 1.202 mmol), was added 3-pyridine boronic acid (CAS#1692=25-7, 177 mg, 1.443 mmol), 1,2-dimethoxyethane (7.5 mL), and 2 M aqueous sodium carbonate (1.503 ml, 3.01 mmol). The reaction mixture was degassed and placed under an argon atmosphere, at which time resin bound tetrakis(triphenylphosphine)palladium(0), specifically polystyrene triphenylphosphine palladium (0) [PS—PPh$^3$—Pd(0) (Biotage), 0.11 mmol/g loading, (328 mg, 0.036 mmol)] was added. The reaction vessel was sealed and was heated by microwave irradiation at 130° C. for 4 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-heptane, 10 to 100%) to furnish 4-cyclopropyl-1-methyl-5-pyridin-3-yl-1,3-dihydro-indol-2-one, HRMS: (ESI) m/z 265.1342 (M+H)+; $^1$H NMR (400 MHz, CD$_2$Cl$_2$) δ ppm 0.12-0.24 (m, 2H), 0.68-0.78 (m, 2H), 1.86-2.00 (m, 1H), 3.19 (s, 3H), 3.59 (s, 2H), 6.80 (d, J=7.8 Hz, 1H), 7.21 (d, J=8.1 Hz, 1H), 7.34 (dd, J=7.7, 4.9 Hz, 1H), 7.73 (d, J=7.6 Hz, 1H), 8.53 (d, J=4.6 Hz, 1H), 8.63 (s, 1H).

Example 43 a) (3-Bromo-5-chloro-pyridin-4-yl)-methanol

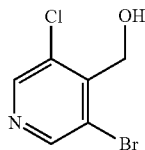

To a solution of diisopropylamine (0.963 ml, 6.76 mmol) in THF (45 ml) at −78° C. was added n-butyllithium (2.5M in hexanes, 2.5 mL, 6.24 mmol). The reaction mixture was stirred for 15 minutes, at which time 3-bromo-5-chloropyridine (CAS#73583-39-8, 1.0 g, 5.20 mmol) in THF (10.0 mL) was added followed by a 1.5 mL THF wash. After 10 minutes methyl chloroformate (0.443 ml, 5.72 mmol) was added. The reaction was stirred for 20 minutes and then quenched at −78° C. with 5% AcOH in MeOH. The reaction was then diluted with saturated aqueous ammonium chloride and placed at room temperature. The reaction was then diluted with DCM and saturated aqueous sodium bicarbonate and the layers were separated. The aqueous layer was extracted two times with dichloromethane, and the organic layers were combined, dried over anhydrous sodium sulfate, filtered and concentrated. The resulting ester was used without further purification. To a solution of lithium aluminum hydride (109 mg, 2.87 mmol) in THF (30 ml) at −78° C. was added a solution of the ester prepared above (450 mg, 1.797 mmol) in THF (7.0 mL). The reaction was permitted to warm to −30° C. and stirred for 45 minutes. The reaction was then quenched with 0.9 mL of a 9:1 THF/H2O solution followed by 2 N NaOH (0.3 mL). The reaction was placed at rt and water (1.0 mL) was added followed by THF (9 mL). The reaction was stirred for 5 minutes and then charged with magnesium sulfate (ca. 1.0 g). The resulting mixture was filtered through a pad of Celite® and the filtrate was concentrated. The resulting residue was purified by silica gel flash chromatography (ethanol-dichloromethane, 0 to 7%) to afford (3-bromo-5-chloro-pyridin-4-yl)-methanol; $^1$H NMR (400 MHz, CDCl$_3$) δ ppm 4.94 (s, 2H), 8.52 (s, 1H), 8.62 (s, 1H).

b) 4-Chloro-5-(5-chloro-4-hydroxymethyl-pyridin-3-yl)-1-methyl-1,3-dihydro-indol-2-one

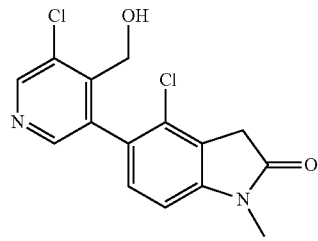 [SMILES: CN1C(=O)Cc2c1ccc(-c1cncc(Cl)c1CO)c2Cl]

To 4-chloro-1-methyl-5-(4,4,5,5-tetramethyl-[1,3,2]dioxaborolan-2-0)-1,3-dihydro-indol-2-one, prepared as described in Example 27a (80 mg, 0260 mmol) was added (3-bromo-5-chloro-pyridin-4-yl)-methanol (69.4 mg, 0.312 mmol) 1,2-dimethoxyethane (3 mL), and 2 M aqueous sodium carbonate (0.325 ml, 0.650 mmol). The reaction mixture was degassed and placed under an argon atmosphere, at which time resin bound tetrakis(triphenylphosphine)palladium(0), specifically polystyrene triphenylphosphine palladium (0) [PS—PPh$_3$-Pd(0) (Biotage), 0.11 nm mmol/g loading, (118 mg, 0.013 mmol)] was added. The reaction vessel was sealed and was heated by microwave irradiation at 120° C. for 2 hours. The reaction mixture was then cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was semi-purified by silica gel flash chromatography (ethanol-dichloromethane, 10 to 100%). The resulting residue was purified by semi-preparative reverse phase HPLC (10 to 45% acetonitrile/water w/0.1% NH$_4$OH) to afford 4-chloro-5-(5-chloro-4-hydroxymethyl-pyridin-3-yl)-1-methyl-1,3-dihydro-indol-2-one; HRMS: (ESI) m/z 323.0358 (M+H)+; $^1$H NMR (400 MHz, CDCl$_3$) δ ppm 3.28 (s, 3H), 3.62 (5, 2H), 4.48 (d, J=12.3 Hz, 1H), 4.76 (d, J=12.4 Hz, 1H), 6.87 (d, J=8.0 Hz, 1H), 7.30 (d, J=8.0 Hz, 1H), 8.41 (s, 1H), 8.69 (s, 1H).

Example 44 a) 4-Benzyloxy-1-methyl-1H-indole

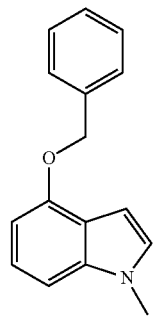 [SMILES: Cn1ccc2c(OCc3ccccc3)cccc21]

To a solution of 4-benzyloxy-1H-indole (CAS#20289-26-3, 10.85 g, 48.6 mmol) in N,N-dimethylformamide (200 mL)

at 0° C., was added sodium hydride (60% dispersion in oil, 2.24 g, 55.9 mmol). The reaction was permitted to stir for 15 minutes at 0° C. Then iodomethane (3.19 mL, 51.0 mmol) was added to the reaction mixture. The reaction was put at room temperature and permitted to stir 30 minutes. The reaction was then quenched with saturated aqueous ammonium chloride. The mixture was diluted with water and extracted with diethyl ether. The layers were separated and the aqueous layer was then extracted two additional times with diethyl ether. The organic layers were combined, dried over anhydrous sodium sulfate, filtered, and concentrated to afford 4-benzyloxy-1-methyl-1H-indole; MS: (ES+) m/z 238.4 (M+H)+.

b) 4-Benzyloxy-5-bromo-1-methyl-1,3-dihydro-indol-2-one

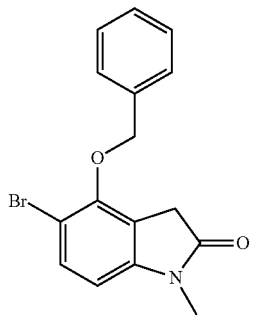 [SMILES: CN1C(=O)Cc2c1ccc(Br)c2OCc1ccccc1]

To a solution of potassium bromide (3.08 g, 25.8 mmol) in water (50 mL) was added bromine (0.667, 12.92 mmol). A separate flask containing 4-benzyloxy-1-methyl-1H-indole (1.46 g, 6.15 mmol) was charged with tert-butanol (50 ml). The mixture was heated to 50° C. until homogeneous. Then water (50 mL) was added to the solution. The mixture was cooled to −10° C. and 50 mL of the bromine solution prepared above was added dropwise over 1 hour. During the addition, the temperature was maintained at −10° C. After addition was complete, the reaction was neutralized with saturated aqueous sodium bicarbonate and quenched with saturated aqueous sodium thiosulfate. The reaction mixture was then diluted with dichloromethane and saturated aqueous sodium bicarbonate and the layers were separated. The aqueous layer was extracted two additional times with dichloromethane and the organic layers were combined, dried over anhydrous sodium sulfate, filtered, and concentrated. The resulting residue was dissolved in acetic acid (20 mL) and zinc dust (1.58 g, 24.33 mmol) was added. The reaction was permitted to stir for 30 minutes at room temperature. Then the reaction mixture was then diluted with dichloromethane (100 mL) and filtered. To the filtrate, ice-water was added, followed by solid sodium carbonate until the pH of reaction mixture to was ca. 8. The resulting layers were separated and the aqueous layer was extracted two additional times with dichloromethane. The organic layers were combined, dried over anhydrous sodium sulfate, filtered, and concentrated. The resulting residue was purified by silica gel flash chromatography (ethyl acetate-heptane, 0 to 60%) to afford 4-benzyloxy-5-bromo-1-methyl-1,3-dihydro-indol-2-one. MS: (ES+) m/z 332.0 (M+H)+.

c) 4-Benzyloxy-1-methyl-5-pyridin-3-yl-1,3-dihydro-4-indol-2-one

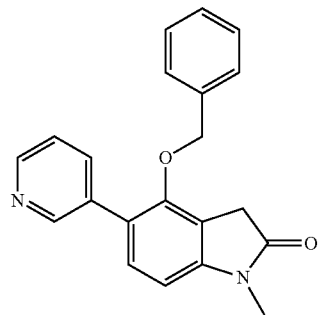 [SMILES: CN1C(=O)Cc2c1ccc(-c1cccnc1)c2OCc1ccccc1]

To 4-benzyloxy-5-bromo-1-methyl-1,3-dihydro-indol-2-one (100 mg, 0.301 mmol) was added 3-pyridineboronic acid (CAS#1692.25-7, 44.4 mg, 0.361 mmol), 1,2-dimethoxyethane (2 mL) and 2 M aqueous sodium carbonate (0.376 ml, 0.753 mmol). The reaction mixture was degassed and placed under an argon atmosphere, at which time resin bound tetrakis(triphenylphosphine)palladium(0), specifically polystyrene triphenylphosphine palladium (0) [PS—PPh3-Pd(0) (Biotage), 0.11 mmol/g loading, (82 mg, 0.0093 mmol)] was added. The reaction vessel was sealed and was heated by microwave irradiation at 130° C. for 2.5 hours. The reaction mixture was cooled to room temperature, diluted with dichloromethane and filtered through glass wool. The filtrate was further diluted with saturated aqueous sodium bicarbonate and the layers were separated. The aqueous layer was extracted two times with dichloromethane, and the organic layers were combined, dried over anhydrous sodium sulfate, filtered and concentrated. The resulting residue was purified by silica gel flash chromatography (ethyl acetate-dichloromethane, 0 to 100%) to afford 4-benzyloxy-1-methyl-5-pyridin-3-yl-1,3-dihydro-indol-2-one; HRMS: (ESI) m/z 331.1447 (M+H)+; $^1$H NMR (400 MHz, DMSO-d$_6$) δ ppm 3.16 (s, 3H), 3.77 (s 2H), 4.93 (s, 2H), 6.88 (d J=8.08 Hz, 1H), 7.16-7.21 (m, 2H), 7.27-7.31 (m, 3H), 7.35 (d, J=8.08 Hz, 1H), 7.41 (qd, 1H), 7.86 (dt, J=7.83, 2.02 Hz, 1H), 5.52 (dd, J=4.80, 1.77 Hz, 1H), 8.67 (dd, J=2.27, 0.76 Hz, 1H).

Example 45 a) 4-Hydroxy-1-methyl-5-pyridin-3-yl-1,3-dihydro-indol-2-one

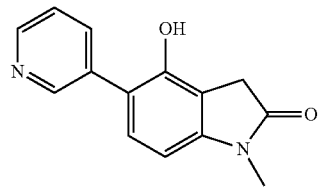 [SMILES: CN1C(=O)Cc2c1ccc(-c1cccnc1)c2O]

To a solution of 4-benzyloxy-1-methyl-5-pyridin-3-yl-1,3-dihydro-indol-2-one (0.3 g, 0908 mmol) in ethanol (20 mL), was added 10% palladium on carbon (0.2 g, 0.28 mmol). The atmosphere over the reaction mixture was evacuated and the reaction was placed under an atmosphere of hydrogen gas via a balloon. The reaction was permitted to stir for 1 hour. The reaction mixture was then filtered through a plug of Celite®. The Celite pad was washed with hot ethanol (200 ml). The combined filtrate was then concentrated to afford 4-hydroxy-1-methyl-5-pyridin-3-yl-1,3-dihydro-indol-2-one; MS: (ES+) m/z 241.1 (M+H)+.

b) 4-Ethoxy-1-methyl-5-pyridin-3-yl-1,3-dihydro-indol-2-one

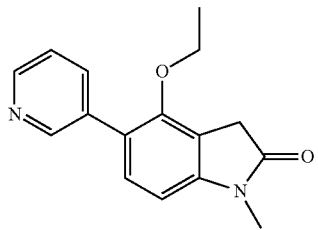 [SMILES: CCOc1c(-c2cccnc2)ccc2c1CC(=O)N2C]

A microwavable vial was charged with 4-hydroxy-1-methyl-5-pyridin-3-yl-1,3-dihydro-indol-2-one (48.1 mg, 0.2 mmol), toluene (2 ml), and ethanol (23.3 μL, 0.4 mmol). Cyanomethylene-tri-n-butylphosphorane (CAS#157141-27-0, 169 mg, 0.700 mmol) was then added to the vial. The reaction vial was sealed and was heated by microwave irradiation at 105° C. for 1 hour. The reaction mixture was cooled to room temperature and diluted with dichloromethane and brine. The layers were separated and the aqueous layer was extracted an additional two times with dichloromethane. The organic layers were combined dried over anhydrous sodium sulfate, filtered and concentrated. The resulting residue was purified by silica gel flash chromatography (ethyl acetate-heptane, 0 to 100%). Further purification was accomplished via reverse phase HPLC (10 to 40% acetonitrile/water w/0.1% NH$_4$OH) to afford 4-ethoxy-1-methyl-5-pyridin-3-yl-1,3-dihydro-indol-2-one; HRMS: (ESI) m/z 269.1289 (M+H)+, $^1$H NMR (400 MHz, CD$_2$Cl$_2$) δ ppm 1.16 (t, J=6.95 Hz, 3H), 3.20 (s, 3H), 3.60 (s, 2H), 3.85 (q, J=6.91 Hz, 2H), 6.68 (d, J=8.08 Hz, 1H), 7.28 (d, J=8.08 Hz, 1H), 7.32 (dd, J=7.83, 4.80 Hz, 1H), 7.85 (dt, J=7.89, 1.99 Hz, 1H), 8.51 (dd. J4.80, 1.77 Hz, 1H), 8.71 (d, J=2.78 Hz, 1H).

Example 46 a) 3-Bromo-5-oxiranyl-pyridine

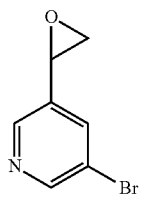

To a solution of trimethylsulfoxonium iodide (CAS#1774-47-6, 11.83 g, 53.8 mmol) in methyl sulfoxide (80 mL), was added slowly sodium hydride (60% dispersion in oil, 1.989 g, 49.7 mmol). The reaction was permitted to stir for 15 min at room temperature. A solution of 5-bromo-pyridine-3-carbaldehyde (CAS#135124-70-8, 5.0 g, 26.9 mmol) in dimethylsulfoxide (20 mL) was added slowly to the reaction mixture. The reaction permitted to stir for 10 minutes after the addition was complete. The reaction was cooled to 0° C., quenched with brine, and diluted with diethyl ether. The layers were separated and the aqueous layer was extracted two additional times with diethyl ether. The organic layers were combined, dried over anhydrous sodium sulfate, filtered and concentrated. The resulting residue was purified by silica gel flash chromatography (ethyl acetate-heptane, 0 to 60%) to afford 3-bromo-5-oxiranyl-pyridine; MS: (ES+) m/z 200.0 (M+H)+.

b) 3-Bromo-5-oxetan-2-yl-pyridine

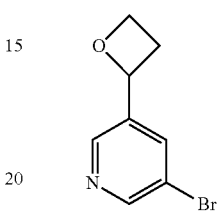

To a suspension of trimethylsulfoxonium iodide (CAS#1774-47-6, 6.38 g, 29.0 mmol) in tert-butanol (20 mL), was added potassium tert-butoxide (3.25 g, 29.0 mmol). The reaction was heated to 50° C. and permitted to stir for 15 min. A solution of 3-bromo-5-oxiranyl-pyridine (2.9 g, 14.50 mmol) in tert-butanol (20 mL) was then added slowly to the reaction. The reaction was permitted to stir at 50° C. for 16 hr. The reaction mixture was cooled to 0° C., quenched with brine, and diluted with diethyl ether. The layers were separated and the aqueous layer was extracted with diethyl ether two additional times. The organic layers were combined, dried over anhydrous sodium sulfate, filtered and concentrated. The resulting residue was purified by silica gel flash chromatography (ethyl acetate-heptane, 0 to 60%) to afford 3-bromo-5-oxetan-2-yl-pyridine; MS: (ES+) m/z 214.3 (M+H)+.

c) (R)- and (S)-1-methyl-5-(5-oxetan-2-yl-pyridin-3-yl)-1,3-dihydro-indol-2-one

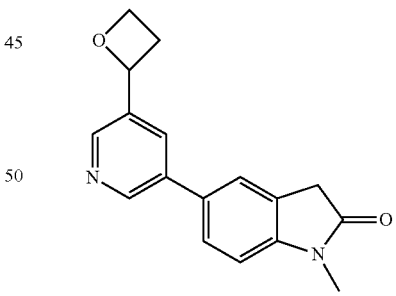

The above compounds was prepared in a similar fashion as described in Example 4; HRMS: (ESI) m/z 281.1295 (M+H)+; $^1$H NMR (400 MHz, CDCl$_3$) δ ppm 2.65-2.78 (m, 1H), 3.17-3.27 (m, 1H), 3.29 (s, 3H), 3.64 (s, 2H), 466-4.82 (m, 1H), 4.88-5.05 (m, 1H), 6.00 (t, J=7.52 Hz, 1H), 6.99 (d, J=8.08 Hz, 1H), 7.44-7.68 (m, 2H), 8.31 (br. s., 1H), 8.64 (d, J=1.64 Hz, 1H), 8.81 (d, J=2.02 Hz, 1H). Resolution of the enantiomers of the title compound was achieved via chiral chromatography by using a ChiralPak IA column with 70/30 isopropanol/heptane as mobile phase to provide (R)- or (S)-1-methyl-5-(5-oxetan-2-yl-pyridin-3-yl)-1,3-dihydro-indol- 2-one (t=23.5 min) and (R)- or (S)-1-methyl-5-(5-oxetan-2-yl-pyridin-3-yl)-1,3-dihydro-indol-2-one (t=35.4 min).

By repeating the procedures described in the examples above, using appropriate starting materials, the following compounds of Formula I, as identified in Table 2, were obtained.

Example 47

1,3-Dimethyl-5-pyridin-3-yl-1,3-dihydro-benzoimidazol-2-one

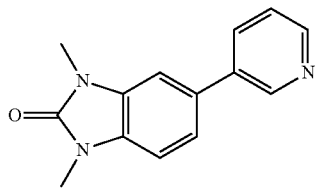

a) 5-Bromo-1,3-dimethyl-1,3-dihydro-benzoimidazol-2-one

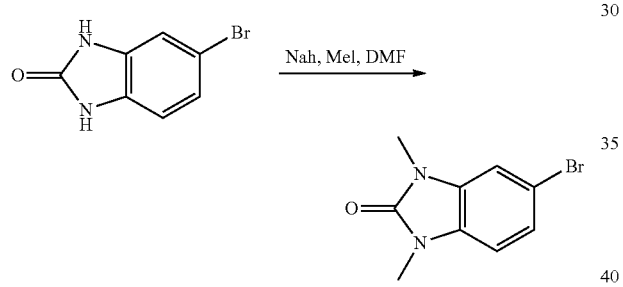

Sodium hydride (60% in mineral oil, 256 mg, 6.4 mmol) was added to a solution of 5-Bromo-1,3-dihydro-1,3-dihydro-benzoimidazol-2-one (427 mg, 2 mmol) in DMF (20 mL) at room temperature. After 10 min, iodomethane (710 mg, 5 mmol) was added dropwise, and the resulting mixture was stirred at room temperature for overnight (15 hrs). The reaction was quenched with water (100 mL) and extracted with ethyl acetate (125 mL×3). The combined extracts were washed with water (100 mL×2), saturated aqueous NaCl solution (100 mL), dried with MgSO$_4$. After concentration, a pale yellow solid was obtained (539 mg) without further purification.

b) 1,3-Dimethyl-5-pyridin-3-yl-1,3-dihydro-benzoimidazol-2-one

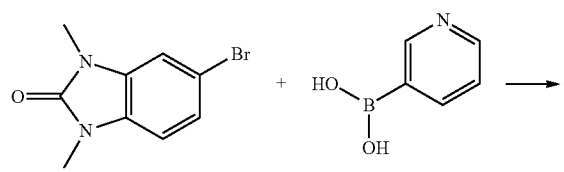

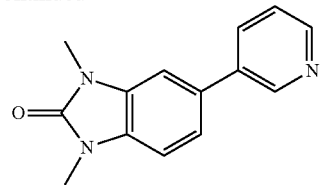 [SMILES: Cn1c(=O)n(C)c2cc(-c3cccnc3)ccc21]

A mixture of 5-Bromo-1,3-dimethyl-1,3-dihydro-benzoimidazol-2-one (121 mg, 0.5 mmol), 3-pyridyl boronic acid (68 mg, 0.55 mmol), polymer-supported Pd(PPh$_3$)$_4$ (0.09 mmol/g, 278 mg, 0.025 mmol) and Na$_2$CO$_3$ (2 M in water, 0.55 mL, 1.1 mmol) in DME (3.3 mL) was heated to reflux for 1 hr. After filtration and concentration, the residue was purified by flash column (MeOH—CH2Cl2, v/v, 0-7.5%) and yielded the title compound (38 mg). MS (ESI) m/z 240.0 (M+H), retention time 1.00 min. $^1$H NMR (400 MHz, CD$_2$Cl$_2$) δ ppm 3.47 (s, 3H), 3.49 (s, 3H), 7.13 (d, J=8.1 Hz, 1H), 7.25 (s, 1H), 7.38-7.40 (m, 1H), 7.41-7.44 (m, 1H), 7.95-7.98 (m, 1H), 8.60 (m, 1H), 8.90 (s, 1H).

Example 48

3-Methyl-6-pyridin-3-yl-3H-benzooxazol-2-one

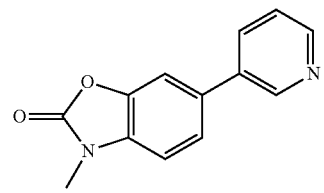 [SMILES: Cn1c(=O)oc2cc(-c3cccnc3)ccc21]

a) 3-Methyl-3H-benzooxazal-2-one

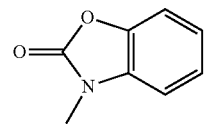

A suspension of o-aminophenol (1.5 g, 13.7 mmol). K$_2$CO$_3$ (3.79 g, 27.4 mmol) in dimethyl carbonate (96.3 g, 90 mL, 1069 mmol) was heated to 90° C. for 1 week. After filtration and concentration, a brownish solid (2 g) was obtained without further purification. $^1$H NMR (400 MHz, CD$_2$Cl$_2$) δ ppm 3.42 (s, 3H), 7.03 (m, 1H), 7.15-7.19 (m, 1H), 7.24-7.27 (m, 2H).

b) 6-Bromo-3-methyl-3H-benzooxazol-1-one

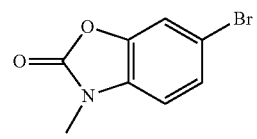

A mixture of 3-Methyl-3H-benzooxazol-2-one (449 mg, 3 mmol), NBS (561 mg, 3.15 mmol), AIBN (10 mg, catalytic amount, 0.061 mmol) in CCl$_4$ (20 mL) was refluxed for 48 hrs. After filtration, the filtrates were diluted with ethyl acetate and washed with water. The organic layer was dried over MgSO$_4$, filtered and concentrated to a reddish brown solid (667 mg) without further purification.

c) 3-Methyl-6-pyridin-3-yl-3H-benzooxazol-2-one

A suspension of 6-Bromo-3-methyl-3H-benzooxazol-2-one (115 mg, 0.5 mmol), 3-pyridyl boronic acid (68 mg, 0.55 mmol), polymer-supported Pd(PPh$_3$)$_4$ (0.09 mmol/g, 278 mg, 0.025 mmol) and Na$_2$CO$_3$ (2 M in water, 0.55 mL, 1.1 mmol) in DME (3.3 mL) was heated to reflux for 1.5 hr. After filtration and concentration, the residue was purified by flash column (MeOH—CH$_2$Cl$_2$, v/v, 0-7%) and yielded the title compound (60 mg). MS (ESI) m/z 227.0 (M+H), retention time 1.04 min. $^1$H NMR (400 MHz, CD$_2$Cl$_2$) δ ppm 3.47 (s, 3H), 7.15 (d, J=8.6 Hz, 1H), 7.41-7.44 (m, 1H), 7.49 (s, 1H), 7.50 (d, J=7 Hz, 1H), 7.91 (d, J=7.9 Hz, 1H), 8.61 (s, 1H), 8.87 (s, 1H).

Example 49

3-Methyl-6-pyridin-3-yl-3H-benzothiazol-2-one

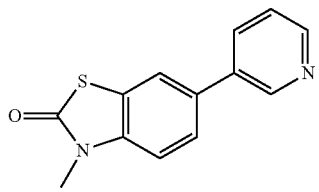 [SMILES: Cn1c(=O)sc2cc(-c3cccnc3)ccc21]

a) 6-Bromo-3-methyl-3H-benzothiazol-2-one

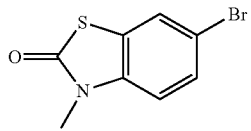

iodomethane (543 uL, 1.234 g, 8.7 mmol) was added dropwise to a suspension of 6-Bromo-3-hydro-3H-benzothiazol-2-one (1 g, 4.35 mmol), K$_2$CO$_3$ (1.5 g, 10.9 mmol) in DMSO (15 mL) at room temperature. The resulting mixture was stirred for overnight. Water (20 mL) and ethyl acetate (25 mL×3) were added, and the organic layer was separated, washed with brine and dried over anhydrous Na$_2$SO$_4$. After filtration and concentration, a colorless solid was obtained (1.4 g). $^1$H NMR (400 MHz, CDCl$_3$) δ ppm 3.42 (s, 3H), 6.89 (d J=8.5 Hz, 1H), 7.43 (dd, J=2, 8.5 Hz, 1H), 7.54 (d, J=2 Hz, 1H).

b) 3-Methyl-6-pyridin-3-yl-3H-benzothiazol-2-one

A suspension of 6-Bromo-3-methyl-3H-benzothiazol-2-one (200 mg, 0.82 mmol), 3-pyridyl boronic acid (78 mg, 0.63 mmol), polymer-supported Pd(PPh$_3$)$_4$ (0.11 mmol/g, 115 mg, 0.0126 mmol) and Na$_2$CO$_3$ (2 M in water, 0.65 mL, 1.3 mmol) in DME (7 mL) was heated to reflux for overnight. After filtration and concentration, the residue was purified by flash column (MeOH—CH$_2$Cl$_2$, v/v, 0-4%) and yielded the title compound (200 mg). MS (ESI) m/z 243.0 (M+H, $^1$H NMR (400 MHz, CD$_2$Cl$_2$) δ ppm 3.52 (s, 3H), 7.23 (d, J=8.4 Hz, 1H), 7.43-7.46 (m, 1H), 7.63 (d, J=8.4 Hz, 1H), 7.73 (s, 1H), 7.93-7.96 (m, 1H), 8.62 (m, 1H), 8.88 (s, 1H).

Example 60

6-(5-aminopyridin-3-yl)-3-methylbenzo[d]thiazol-2(3H)-one

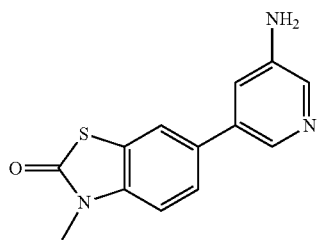 [SMILES: Cn1c(=O)sc2cc(-c3cncc(N)c3)ccc21]

a) 3-Methyl-6-(4,4,5,5-tetramethyl-[1,3,2]dioxaborolan-2-yl)-3H-benzothiazol-2-one

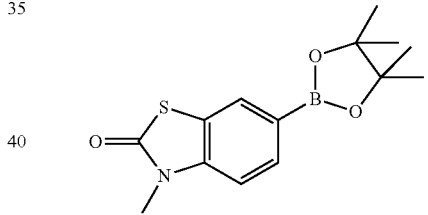

A mixture of 6-Bromo-3-methyl-3H-benzothiazol-2-one (1220.5 mg, 5 mmol), 4,4,4',4',5,5,5',5'-octamethyl-2,2'-bi(1,3,2-dioxaborolane) (1396.7 mg, 5.5 mmol), PdCl2(dppf).CH$_2$Cl$_2$ (183 mg, 0.25 mmol), potassium acetate (980 mg, 10 mmol) in 1,4-dioxane (15 mL) was heated to 80° C. for 5 hrs. After concentration, the residue was purified by flash column (ethyl acetate/heptane, v/v, 10-30%) and yielded the title compound (1.3 g). MS (ESI) m/z 292.0 (M+H)$^+$.

b) Synthesis of 6-(5-aminopyridin-3-yl)-3-methyl-benzo[d]thiazol-2(3H)-one

A mixture of 3-Methyl-6-(4,4,5,5-tetramethyl-[1,3,2]dioxaborolan-2-yl)-3H-benzothiazol-2-one (873.5 mg, 3 mmol), 5-Bromo-pyridin-3-ylamine (519 mg, 3 mmol), Pd$_2$(dba)$_3$ (24.7 mg, 0.06 mmol), S—PHOS (62 mg, 0.15 mmol), K$_3$PO$_4$ (1.27 g, 6 mmol) in toluene (15 mL) was heated to 95° C. for overnight. After filtration, concentration, the residue was purified by flash column (MeOH/CH$_2$Cl$_2$, v/v, 1.5-3%) and yielded yellow solid (380 mg). MS (ESI) m/z 258.0 (M+H)$^+$. $^1$H NMR (400 MHz, CDCl$_3$) δ ppm 3.49 (s, 3H), 3.78 (brs, 2H), 7.10-7.12 (m, 1H), 7.12 (s, 1H), 7.51 (dd, J=8, 2 Hz, 1H), 7.60 (d, J=2 Hz, 1H), 8.08 (d, J=2.6 Hz, 1H), 8.23 (d. J=2 Hz, 1H).

Example 51

N-(5-(3-methyl-2-oxo-2,3-dihydrobenzo[d]thiazol-6-yl)pyridin-3-yl)ethanesulfonamide

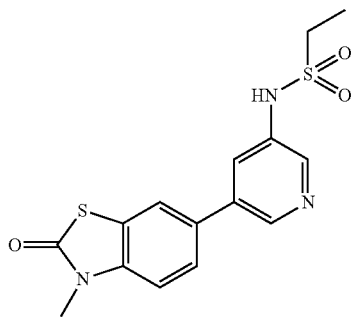 [SMILES: CCS(=O)(=O)Nc1cncc(-c2ccc3c(c2)sc(=O)n3C)c1]

General sulfonylation procedure: EtSO$_2$Cl (51.4 mg, 0.4 mmol) was added dropwise to a solution of 6-(5-aminopyridin-3-yl)-3-methylbenzo[d]thiazol-2(3H)-one (Example 50: 28 mg, 0.1 mmol) in pyridine (2 mL) at 0° C. The resulting mixture was slowly warmed up to room temperature and stirred for additional 3 hrs at this temperature. After concentration, the residue was purified by flash column (MeOH/CH$_2$Cl$_2$, v/v, 1-3%) and yielded yellow solid (20 mg), MS (ESI) m/z 350.4 (M±H)$^+$. $^1$H NMR (400 MHz, MeOD) δ ppm 1.35 (t, J=7.4 Hz, 3H), 3.22 (q, J=7.4 Hz, 2H), 3.51 (q, 3H), 7.38 (d, J=8 Hz, 1H), 7.68 (d, J=8 Hz, 1H), 7.87 (s, 1H), 7.95 (s, 1H), 8.40 (s, 1H), 8.58 (s, 1H).

Example 52

N-(5-(3-methyl-2-oxo-2,3-dihydrobenzo[d]thiazol-6-yl)pyridin-3-yl)cyclopropanesulfonamide

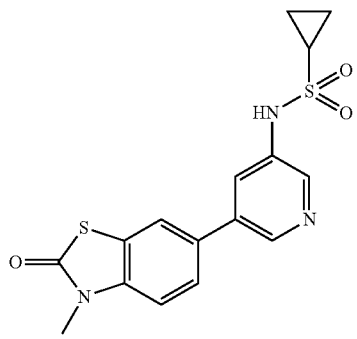 [SMILES: Cn1c(=O)sc2cc(-c3cncc(NS(=O)(=O)C4CC4)c3)ccc21]

The entitled compound was prepared as in Example 51 using the general sulfonylation procedure. MS (ESI) m/z 360.0 (M+H)$^+$ retention time 1.00 min. $^1$H NMR (400 MHz, CD$_2$Cl$_2$) δ ppm, 0.97-1.17 (m, 4H), 2.47 (m, 1H), 3.44 (s, 3H), 6.52 (brs, 1H), 7.08 (d, J=8 Hz, 1H), 7.48 (d. J=8 Hz, 1H), 7.58 (s, 1H), 7.84 (s, 1H), 8.37 (s, 1H), 8.59 (s, 1H).

TABLE 2

| Compound # (Prepared According to Example #) | Structure and Name | NMR and/or ESMS |
| --- | --- | --- |
| 1a (Example 1) | 5-(5-Methanesulfonyl-pyridin-3-yl)-1-methyl-1,3-dihydro-indol-2-one | HRMS (ESI) m/z 303.0812 (M + H)$^+$; 1H NMR (400 MHz, CDCl$_3$) δ ppm 3.18 (s, 3 H), 3.29 (s, 3 H), 3.64 (s, 2 H), 6.98 (d, J = 8.1 Hz, 1 H), 7.49-7.63 (m, 2 H), 8.41 (t, J = 2.2 Hz, 1 H), 9.09 (d, J = 2.3 Hz, 1 H), 9.10 (d, J = 2.3 Hz, 1 H). |
| 1b (Example 1) | 1-Methyl-5-(4-methyl-pyridin-3-yl)-1,3-dihydro-indol-2-one | HRMS: (ESI) m/z 239.1818 (M + H)$^+$; $^1$H NMR (400 MHz, CD$_2$Cl$_2$) δ ppm 2.31 (s, 3 H), 3.22 (s, 3 H), 3.55 (s, 2 H), 6.92 (d, J = 8.1 Hz, 1 H), 7.09-7.35 (m, 3 H), 8.29-8.49 (m, 2 H). |

TABLE 2-continued

| Compound # (Prepared According to Example #) | Structure and Name | NMR and/or ESMS |
|---|---|---|
| 2a (Example 2) | 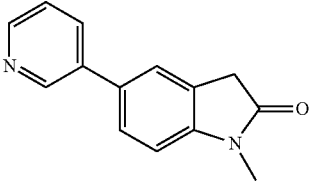 [SMILES: CN1C(=O)Cc2cc(-c3cccnc3)ccc21]  1-Methyl-5-pyridin-3-yl-1,3-dihydro-indol-2-one | MS: (ES+) m/z 225 (M + H); $^1$H NMR (400 MHz, DMSO-d$_6$) δ ppm 3.18 (s, 3 H), 3.64 (s, 2 H), 7.12 (d, J = 8.8 Hz, 1 H), 7.47 (ddd, J = 8.0, 4.8, 0.8 Hz, 1 H), 7.65-7.69 (m, 2 H), 8.05 (ddd, J = 7.9, 2.5, 1.7 Hz, 1 H), 8.53 (dd, J = 4.7, 1.6 Hz, 1 H), 8.87 (d, J = 1.6 Hz, 1 H). |
| 2b (Example 2) | 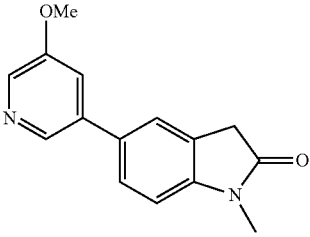  5-(5-Methoxy-pyridin-3-yl)-1-methyl-1,3-dihydro-indol-2-one | MS: (ES+) m/z 255 (M + H); $^1$H NMR (400 MHz, DMSO-d$_6$) of the trifluoracetic acid salt: δ ppm 3.18 (s, 3 H), 3.65 (s, 2 H), 3.95 (s, 3 H), 7.13 (d, J = 8.9 Hz, 1 H), 7.73 (s, 1 H), 7.74-7.77 (m, 2 H), 8.33 (d, J = 2.7 Hz, 1 H), 8.55 (d, J = 1.8 Hz, 1 H). |
| 3c (Example 3) | 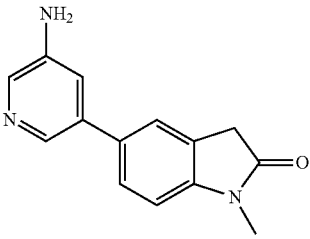  5-(5-Amino-pyridin-3-yl)-1-methyl-1,3-dihydro-indol-2-one | HRMS: (ESI) m/z 240.1139 (M + H)$^+$; $^1$H NMR (400 MHz, DMSO-d$_6$) δ ppm 3.16 (s, 3 H), 3.62 (s, 2 H), 5.36 (s, 2 H), 7.07 (d, J = 8.3 Hz, 1 H), 7.11 (t, J = 2.3 Hz, 1 H), 7.48-7.57 (m, 2 H), 7.89 (d, J = 2.5 Hz, 1 H), 8.00 (d, J = 2.0 Hz, 1 H). |
| 3d (Example 3) | 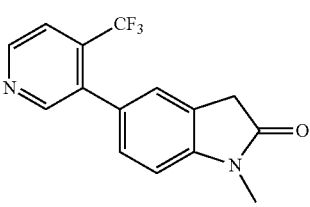 [SMILES: CN1C(=O)Cc2cc(-c3cnccc3C(F)(F)F)ccc21]  1-Methyl-5-(4-trifluoromethyl-pyridin-3-yl)-1,3-dihydro-indol-2-one | HRMS: (ESI) m/z 293.0904 (M + H)$^+$; $^1$H NMR (400 MHz, CDCl$_3$) δ ppm 3.28 (s, 3 H), 3.60 (s, 2 H), 6.91 (d, J = 7.8 Hz, 1 H), 7.17-7.33 (m, 2 H), 7.64 (d, J = 5.3 Hz, 1 H), 8.66 (s, 1 H), 8.79 (d, J = 5.1 Hz, 1 H). |
| 3e (Example 3) | 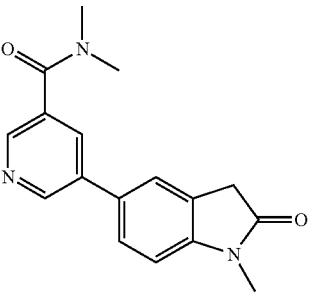 [SMILES: CN(C)C(=O)c1cncc(-c2ccc3c(c2)CC(=O)N3C)c1]  N,N-Dimethyl-5-(1-methyl-2-oxo-2,3-dihydro-1H-indol-5-yl)-nicotinamide | HRMS: (ESI) m/z 296.1401 (M + H)+; $^1$H NMR (400 MHz, CDCl$_3$) δppm 3.08 (br. s., 3 H), 3.18 (br. s., 3 H), 3.27 (s, 3 H), 3.62 (s, 2 H), 6.95 (d, J = 8.1 Hz, 1 H), 7.43-7.58 (m, 2 H), 7.95 (t, J = 2.0 Hz, 1 H), 8.63 (d, J = 1.8 Hz, 1 H), 8.86 (d, J = 2.3 Hz, 1 H). |

| Compound # (Prepared According to Example #) | Structure and Name | NMR and/or ESMS |
|---|---|---|
| 3f (Example 3) | N-Isopropyl-5-(1-methyl-2-oxo-2,3-dihydro-1H-indol-5-yl)-nicotinamide | HRMS: (ESI) m/z 310.1560 (M + H)+; $^1$H NMR (400 MHz, DMSO-d$_6$) δppm 1.21 (d, J = 6.57 Hz, 6 H), 3.18 (s, 3 H), 3.65 (s, 2 H), 4.06-4.22 (m, 1 H), 7.14 (d, J = 8.8 Hz, 0 H), 7.70-7.80 (m, 2 H), 8.39 (d, J = 4.3 Hz, 1 H), 8.50 (d, J = 7.8 Hz, 1 H), 8.92 (d, J = 2.0 Hz, 1 H), 8.98 (d, J = 2.3 Hz, 1 H). |
| 3g (Example 3) | 1-Methyl-5-[5-(morpholine-4-sulfonyl)-pyridin-3-yl]-1,3-dihydro-indol-2-one | HRMS: (ESI) m/z 374.1175 (M + H)$^+$; $^1$H NMR (400 MHz, CDCl$_3$) δ ppm 3.07-3.15 (m, 4 H) 3.29 (s, 3 H), 3.65 (s, 2 H), 3.75-3.84 (m, 4 H), 6.98 (d, J = 8.1 Hz, 1 H), 7.53 (s, 1 H), 7.56 (d, J = 8.1 Hz, 1 H), 8.21 (s, 1 H), 8.92 (d, J = 1.8 Hz, 1 H), 9.05 (d, J = 1.5 Hz, 1 H). |
| 3h (Example 3) | 5-(1-Methyl-2-oxo-2,3-dihydro-1H-indol-5-yl)-pyridine-3-sulfonic acid dimethylamide | HRMS: (ESI) m/z 332.1066 (M + H)$^+$; $^1$H NMR (400 MHz, DMSO-d$_6$) δ ppm 2.72 (s, 6 H), 3.18 (s, 3 H), 3.64 (s, 2 H), 7.14 (d, J = 8.8 Hz, 1 H), 771-7.92 (m, 2 H), 8.25 (t, J = 2.1 Hz, 1 H), 8.85 (d, J = 2.0 Hz, 1 H), 9.19 (d, J = 2.0 Hz, 1 H). |
| 3i (Example 3) | 5-(1-Methyl-2-oxo-2,3-dihydro-1H-indol-5-yl)-pyridine-3-sulfonic acid diethylamide | HRMS: (ESI) m/z 360.1381 (M + H)$^+$; $^1$H NMR (400 MHz, DMSO-d$_6$) δ ppm 1.09 (t, J = 7.2 Hz, 6 H), 3.18 (s, 3 H), 3.26 (q, J = 7.1 Hz, 4 H), 3.65 (s, 2 H), 7.14 (d, J = 8.8 Hz, 1 H), 7.73-7.82 (m, 2 H), 8.31 (t, J = 2.1 Hz, 1 H), 8.90 (d, J = 2.0 Hz, 1 H), 9.14 (d, J = 2.3 Hz, 1 H). |

TABLE 2-continued

| Compound # (Prepared According to Example #) | Structure and Name | NMR and/or ESMS |
|---|---|---|
| 4a (Example 4) | 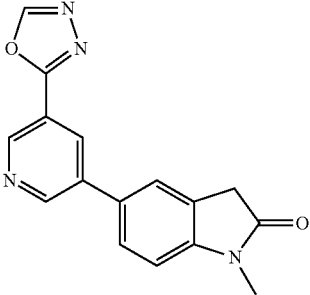 [SMILES: CN1C(=O)Cc2cc(-c3cncc(-c4nnco4)c3)ccc21]<br>1-Methyl-5-(5-[1,3,4]oxadiazol-2-yl-pyridin-3-yl)-1,3-dihydro-indol-2-one | HRMS: (ESI) m/z 293.1037 (M + H)+; $^1$H NMR (400 MHz, CDCl$_3$) δppm 3.29 (s, 3 H), 3.65 (s, 2 H), 6.98 (d, J = 8.1 Hz, 1 H), 7.48-7.68 (m, 2 H), 8.43-8.68 (m, 2 H), 9.01 (s, 1 H), 9.24 (s, 1 H). |
| 4b (Example 4) | 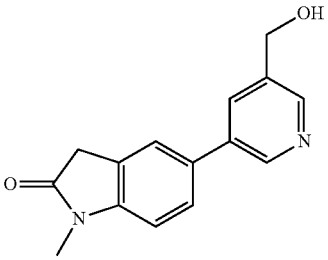 [SMILES: CN1C(=O)Cc2cc(-c3cncc(CO)c3)ccc21]<br>5-(5-Hydroxymethyl-pyridin-3-yl)-1-methyl-1,3-dihydro-indol-2-one | HRMS: (ESI) m/z 255.1134 (M + H)+; $^1$H NMR (400 MHz, DMSO-d$_6$) δppm 3.15 (s, 3 H), 3.62 (s, 2 H), 4.59 (d, J = 5.6 Hz, 2 H), 5.39 (t, J = 5.8 Hz, 1 H), 7.10 (d, J = 8.8 Hz, 1 H), 7.64 (s, 1 H), 7.65 (s, 1 H), 7.94 (t, J = 2.2 Hz, 1 H), 8.46 (d, J = 2.0 Hz, 1 H), 8.73 (d, J = 2.3 Hz, 1 H). |
| 4c (Example 4) | 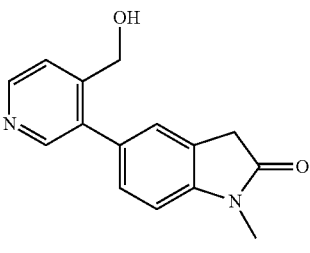 [SMILES: CN1C(=O)Cc2cc(-c3cnccc3CO)ccc21]<br>5-(4-Hydroxymethyl-pyridin-3-yl)-1-methyl-1,3-dihydro-indol-2-one | HRMS: (ESI) m/z 255.1130 (M + H)$^+$; $^1$H NMR (400 MHz, CDCl$_3$) δ ppm 3.16 (s, 3 H), 3.61 (s, 2 H), 4.47 (d, J = 5.6 Hz, 2 H), 5.39 (t, J = 5.4 Hz, 1 H), 7.07 (d, J = 8.6 Hz, 1 H), 7.23-7.36 (m, 2 H), 7.57 (d, J = 5.1 Hz, 1 H), 8.36 (s, 1 H), 8.54 (d, J = 5.1 Hz, 1 H). |
| 4d (Example 4) | 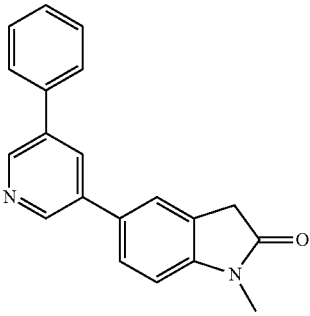 [SMILES: CN1C(=O)Cc2cc(-c3cncc(-c4ccccc4)c3)ccc21]<br>1-Methyl-5-(5-phenylpyridin-3-yl)indolin-2-one | HRMS: (ESI) m/z 301.1340 (M + H)$^+$; $^1$H NMR (400 MHz, CDCl$_3$) δ ppm 3.29 (s, 3 H), 3.64 (s, 2 H), 6.97 (d, J = 8.1 Hz, 1 H), 7.44-7.62 (m, 5 H), 7.62-7.73 (m, 2 H), 8.10 (s, 1 H), 8.73-8.87 (m, 2 H). |

TABLE 2-continued

| Compound # (Prepared According to Example #) | Structure and Name | NMR and/or ESMS |
|---|---|---|
| 4e (Example 4) | 5-(5-Hydroxypyridin-3-yl)-1-methylindolin-2-one | HRMS: (ESI) m/z 241.0976 (M + H)+; $^1$H NMR (400 MHz, DMSO-$d_6$) δ ppm 3.15 (s, 3 H), 3.61 (s, 2 H), 7.08 (d, J = 8.1 Hz, 1 H), 7.27-7.39 (m, 1 H), 7.51-7.73 (m, 2 H), 8.08 (d, J = 2.8 Hz, 1 H), 8.31 (d, J = 2.0 Hz, 1 H), 9.97 (s, 1 H). |
| 5a (Example 5) | 1-Methyl-5-(5-trifluoromethyl-pyridin-3-yl)-1,3-dihydro-indol-2-one | MS: (ES+) m/z 293 (M + H)+; $^1$H NMR (400 MHz, DMSO-$d_6$) δ ppm 3.16 (s, 3 H), 3.62 (s, 2 H), 7.11 (d, J = 8.7 Hz, 1 H), 7.75-7.81 (m, 2H), 8.39 (s, 1 H), 8.87 (s, 1 H), 9.15 (s, 1 H). |
| 5b (Example 5) | 5-(5-Benzyloxy-pyridin-3-yl)-1-methyl-1,3-dihydro-indol-2-one | MS: (ES+) m/z 331 (M + H)+; $^1$H NMR (400 MHz, DMSO-$d_6$) δ ppm 3.15 (s, 3 H), 3.62 (s, 2 H), 5.29 (s, 2 H), 7.09 (d, J = 8.6 Hz, 1 H), 7.34 (d, J = 7.1 Hz, 1 H), 7.40 (t, J = 7.3 Hz, 2 H), 7.44-7.51 (m, 2 H), 7.69 (br. s., 2 H), 7.82 (s, 1 H), 8.35 (s, 1 H), 8.52 (s, 1 H). |
| 5c (Example 5) | 3-(1-Methyl-2-oxo-2,3-dihydro-1H-indol-5-yl)-isonicotinonitrile | MS: (ES+) m/z 250 (M + H)+; $^1$H NMR (400 MHz, DMSO-$d_6$) δ ppm 3.20 (s, 3 H), 3.67 (s, 2 H), 7.20 (d, J = 8.0 Hz, 1 H), 7.59 (s, 1 H), 7.62 (d, J = 8.0 Hz, 1 H), 7.97 (dd, J = 5.1, 0.82 Hz, 1 H), 8.79 (d, J = 5.0 Hz, 1 H), 8.89 (d, J = 0.8 Hz, 1 H). |

TABLE 2-continued

| Compound # (Prepared According to Example #) | Structure and Name | NMR and/or ESMS |
|---|---|---|
| 5d (Example 5) | 1-Methyl-5-(5-(morpholine-4-carbonyl)-pyridin-3-yl]-1,3-dihydro-indol-2-one | MS: (ES+) m/z 338 (M + H)+; $^1$H NMR (400 MHz, DMSO-d$_6$) δ ppm 3.15 (s, 3 H), 3.34 (s, 4 H), 3.59-3.63 (m, 4 H), 7.09 (d, J = 8.7 Hz, 1 H), 7.67-7.71 (m, 2 H), 8.04 (t, J = 2.1 Hz, 1 H), 8.52 (d, J = 1.9 Hz, 1 H), 8.91 (d, J = 2.3 Hz, 1 H). |
| 5e (Example 5) | 5-(1-Methyl-2-oxo-2,3-dihydro-1H-indol-5-yl)-nicotinonitrile | MS: (ES+) m/z 250 (M + H)+; $^1$H NMR (400 MHz, DMSO-d$_6$) δ ppm 3.18 (s, 3 H), 3.65 (s, 2 H), 7.15 (d, J = 8.5 Hz, 1 H), 7.77-7.81 (m, 2 H), 8.63 (t, J = 2.2 Hz, 1 H), 8.96 (d, J = 1.9 Hz, 1 H), 9.18 (d, J = 2.4 Hz, 1 H). |
| 5f (Example 5) | [5-(1-Methyl-2-oxo-2,3-dihydro-1H-indol-5-yl)-pyridin-3-yl]-acetonitrile | MS: (ES+) m/z 264 (M + H)+; $^1$H NMR (400 MHz, DMSO-d$_6$) δ ppm 3.15 (s, 3 H), 3.62 (s, 2 H), 4.13 (s, 2 H), 7.10 (d, J = 8.5 Hz, 1 H), 7.61-7.68 (m, 2 H), 8.00 (s, 1 H), 8.48 (s, 1 H), 8.80 (s, 1 H). |
| 5g (Example 5) | 5-(5-Chloro-pyridin-3-yl)-1-methyl-1,3-dihydro-indol-2-one | MS: (ES+) m/z 259 (M + H)+; $^1$H NMR (400 MHz, DMSO-d$_6$) δ ppm 3.18 (s, 3 H), 3.64 (s, 2 H), 7.13 (d, J = 9.0 Hz, 1 H), 7.73-7.77 (m, 2 H), 8.22 (t, J = 2.2 Hz, 1 H), 8.58 (d, J = 2.3 Hz, 1 H), 8.86 (d, J = 2.0 Hz, 1 H). |

TABLE 2-continued

| Compound # (Prepared According to Example #) | Structure and Name | NMR and/or ESMS |
|---|---|---|
| 6d (Example 6) | 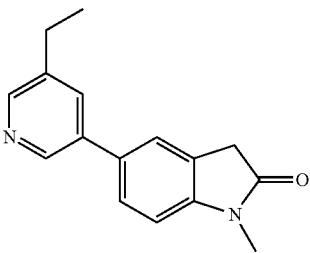 [SMILES: CCc1cncc(-c2ccc3c(c2)CC(=O)N3C)c1]<br>5-(5-Ethyl-pyridin-3-yl)-1-methyl-1,3-dihydro-indol-2-one | HRMS: (ESI) m/z 253.1340 (M + H)+; $^1$H NMR (400 MHz, CDCl$_3$) δ ppm 1.33 (t, J = 7.6 Hz, 3 H), 2.74 (q, J = 7.6 Hz, 2 H), 3.27 (s, 3 H) 3.61 (s, 2 H), 6.93 (d, J = 8.1 Hz, 1 H), 7.41-7.57 (m, 2 H), 7.67 (s, 1 H), 8.44 (s, 1 H), 8.65 (s, 1 H). |
| 7c (Example 7) | 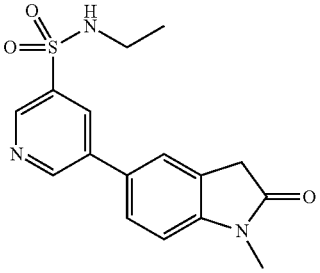 [SMILES: CCNS(=O)(=O)c1cncc(-c2ccc3c(c2)CC(=O)N3C)c1]<br>5-(1-Methyl-2-oxo-2,3-dihydro-1H-indol-5-yl)-pyridine-3-sulfonic acid ethylamide | HRMS: (ES+) m/z 332.1068 (M + H)+; $^1$H NMR (400 MHz, DMSO-d$_6$) δ ppm 1.00 (t, J = 7.2 Hz, 3 H), 2.83-2.92 (m, 2 H), 3.18 (s, 3 H), 3.65 (s, 2 H), 7.15 (d, J = 8.1 Hz, 1 H), 7.72-7.77 (m, 2 H), 7.80 (t, J = 5.6 Hz, 1 H), 8.33 (t, J = 2.3 Hz, 1 H), 8.86 (d, J = 2.0 Hz, 1 H), 9.12 (d, J = 2.3 Hz, 1 H). |
| 16c (Example 16) | 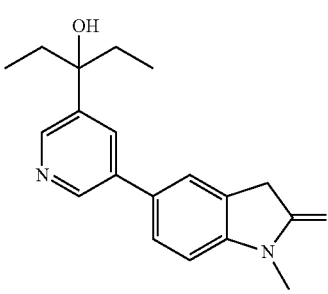<br>5-[5-(1-Ethyl-1-hydroxy-propyl)-pyridin-3-yl]-1-methyl-1,3-dihydro-indol-2-one | HRMS: (ESI) m/z 311.1768 (M + H)+; $^1$H NMR (400 MHz, CDCl$_3$) δ ppm 0.84 (t, J = 7.45 Hz, 6 H), 1.85 (s, 1 H), 1.89-2.00 (m, 4 H), 3.28 (s, 3 H), 3.63 (s, 2 H), 6.96 (d, J = 8.08 Hz, 1 H), 7.52 (s, 1 H), 7.55 (d, J = 8.08 Hz, 1 H), 8.11 (s, 1 H), 8.62 (s, 1 H), 8.72 (s, 1 H). |
| 19c (Example 19) | 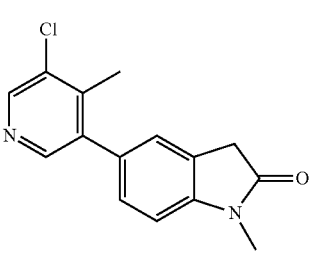 [SMILES: Cc1c(Cl)cncc1-c1ccc2c(c1)CC(=O)N2C]<br>5-(5-Chloro-4-methyl-pyridin-3-yl)-1-methyl-1,3-dihydro-indol-2-one | HRMS: (ES+) m/z 273.0796 (M + H)+; $^1$H NMR (400 MHz, CDCl$_3$) δ ppm 2.36 (s, 3 H), 3.28 (s, 3 H), 3.61 (s, 2 H), 6.93 (d, J = 8.1 Hz, 1 H), 7.16-7.25 (m, 2 H), 8.33 (s, 1 H), 8.53 (s, 1 H) |

TABLE 2-continued

| Compound # (Prepared According to Example #) | Structure and Name | NMR and/or ESMS |
|---|---|---|
| 23a (Example 23) | 1-Methyl-5-(5-pyrimidin-5-yl-pyridin-3-yl)-1,3-dihydro-indol-2-one | HRMS: (ESI) m/z 303.1246 (M + H)+; 1H NMR (400 MHz, DMSO-d6) δ ppm 3.18 (s, 3 H), 3.65 (s, 2 H), 7.15 (d, J = 8.59 Hz, 1 H), 7.78-7.87 (m, 2 H), 8.49 (t, J = 2.15 Hz, 1 H), 8.97 (dd, J = 4.93, 2.15 Hz, 2 H), 9.27 (s, 1 H), 9.34 (s, 2 H) |
| 23b (Example 23) | 7-Chloro-1-methyl-5-pyridin-3-yl-1,3-dihydro-indol-2-one | HRMS: (ESI) m/z 259.0640 (M + H)+; 1H NMR (400 MHz, CD2Cl2) δ ppm 3.58 (s, 3 H), 3.59 (s, 2 H), 7.39 (s, 1 H), 7.39-7.43 (m, 1 H), 7.47 (s, 1 H), 7.88 (d, J = 8.1 Hz, 1 H), 8.57 (d, J = 6.3 Hz, 1 H), 8.80 (s, 1 H). |
| 26d (Example 26) | 6-Chloro-1-methyl-5-pyridin-3-yl-1,3-dihydro-indol-2-one | HRMS: (ESI) m/z 259.0640 (M + H)+; 1H NMR (400 MHz, DMSO-d6) δ ppm 3.17 (s, 3 H), 3.61 (s, 2 H), 7.29 (s, 1 H), 7.36 (s, 1 H), 7.50 (m, 1 H), 7.85 (m, 1 H), 8.56-8.63 (m, 2 H) |
| 26e (Example 26) | 4-Chloro-5-(5-chloro-pyridin-3-yl)-1-methyl-1,3-dihydro-indol-2-one | HRMS: (ESI) m/z 293.0251 (M + H)+; 1H NMR (400 MHz, CDCl3) δ 3.27 (s, 3 H), 3.61 (s, 2 H), 6.85 (d, J = 8.1 Hz, 1 H), 7.30 (d, J = 8.1 Hz, 1 H), 7.78 (t, J = 2.0 Hz, 1 H), 8.56 (d, J = 1.77 Hz, 1 H), 8.60 (d, J = 2.3 Hz, 1 H) |
| 26f (Example 26) | 4-Chloro-1-methyl-5-(4-methyl-pyridin-3-yl)-1,3-dihydro-indol-2-one | HRMS: (ESI) m/z 273.0796 (M + H)+; 1H NMR (400 MHz, CDCl3) δ ppm 2.22 (s, 3 H), 3.28 (s, 3 H), 3.61 (s, 2 H), 6.84 (d, J = 8.1 Hz, 1 H) 7.18 (d, J = 8.1 Hz, 1 H), 7.31 (d, J = 5.1 Hz, 1 H), 8.38 (s, 1 H), 8.53 (d, J = 5.1 Hz, 1 H). |

TABLE 2-continued

| Compound # (Prepared According to Example #) | Structure and Name | NMR and/or ESMS |
|---|---|---|
| 26g (Example 26) | 4-Chloro-1-methyl-5-(5-methyl-pyridin-3-yl)-1,3-dihydro-indol-2-one | HRMS: (ESI) m/z 273.0801 (M + H)+; $^1$H NMR (400 MHz, CDCl$_3$) δ ppm 2.45 (s, 3 H), 3.27 (s, 3 H), 3.61 (s, 2 H), 6.84 (d, J = 8.1 Hz, 1 H) 7.29 (d, J = 8.1 Hz, 1 H), 7.66 (br. s., 1 H), 8.47 (s, 1 H), 8.49 (s, 1 H). |
| 27c (Example 27) | 5-(4-Chloro-1-methyl-2-oxo-2,3-dihydro-1H-indol-5-yl)-pyridine-3-sulfonic acid dimethylamide | HRMS: (ESI) m/z 366.0692 (M + H)+; $^1$H NMR (400 MHz; CDCl$_3$) δ ppm 2.83 (s, 6 H), 3.28 (s, 3 H), 3.63 (s, 2 H), 6.89 (d, J = 8.1 Hz, 1 H) 7.34 (d, J = 7.96 Hz, 1 H), 8.19 (t, J = 2.0 Hz, 1 H), 8.88 (d, J = 1.9 Hz, 1 H), 9.00 (d, J = 1.9 Hz, 1H). |
| 27d (Examples 16a and 27) | 4-Chloro-5-[5-(1-hydroxy-1-methyl-ethyl)-pyridin-3-yl]-1-methyl-1,3-dihydro-indol-2-one | HRMS: (ESI) m/z 317.1065 (M + H)+; $^1$H NMR (400 MHz, DMSO-d$_6$) δ ppm 1.51 (s, 6 H), 3.18 (s, 3 H), 3.66 (s, 2 H), 5.27 (s, 1 H), 7.11 (d, J = 8.1 Hz, 1 H), 7.42 (d, J = 8.1 Hz, 1 H), 7.88 (t, J = 2.2 Hz, 1 H), 8.46 (d, J = 2.3 Hz, 1 H), 8.70 (d, J = 2.0 Hz, 1 H). |
| 27e (Example 27) | 4-Chloro-5-(5-hydroxymethyl-pyridin-3-yl)-1-methyl-1,3-dihydro-indol-2-one | HRMS: (ESI) m/z 289.0753 (M + H)+; $^1$H NMR (400 MHz, DMSO-d$_6$) δ ppm 3.17 (s, 3 H), 3.66 (s, 2 H), 4.60 (d, J = 5.6 Hz, 2 H), 5.38 (t, J = 5.8 Hz, 1 H), 7.11 (d, J = 8.1 Hz, 1 H), 7.40 (d, J = 8.1 Hz, 1 H), 7.76 (t, J = 2.1 Hz, 1 H), 8.48 (d, J = 2.0 Hz, 1 H), 8.53 (d, J = 2.0 Hz, 1 H). |

TABLE 2-continued

| Compound # (Prepared According to Example #) | Structure and Name | NMR and/or ESMS |
|---|---|---|
| 27f (Examples 10a and 27) | 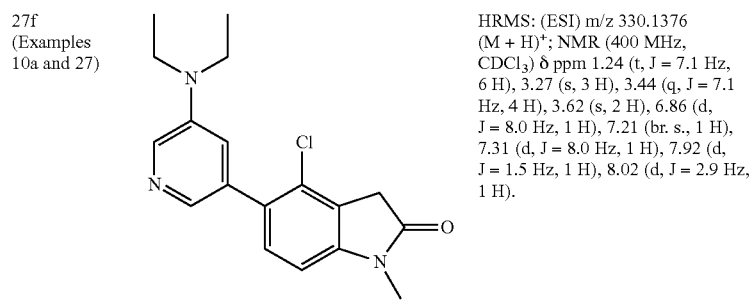<br>4-Chloro-5-(5-diethylamino-pyridin-3-yl)-1-methyl-1,3-dihydro-indol-2-one | HRMS: (ESI) m/z 330.1376 (M + H)$^+$; NMR (400 MHz, CDCl$_3$) δ ppm 1.24 (t, J = 7.1 Hz, 6 H), 3.27 (s, 3 H), 3.44 (q, J = 7.1 Hz, 4 H), 3.62 (s, 2 H), 6.86 (d, J = 8.0 Hz, 1 H), 7.21 (br. s., 1 H), 7.31 (d, J = 8.0 Hz, 1 H), 7.92 (d, J = 1.5 Hz, 1 H), 8.02 (d, J = 2.9 Hz, 1 H). |
| 27g (Examples 12a and 27) | 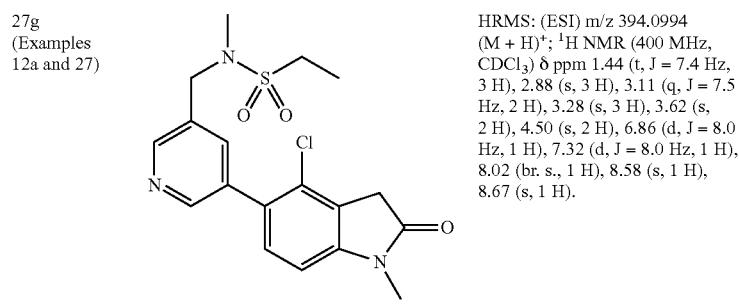<br>Ethanesulfonic acid [5-(4-chloro-1-methyl-2-oxo-2,3-dihydro-1H-indol-5-yl)-pyridin-3-ylmethyl]-methyl-amide | HRMS: (ESI) m/z 394.0994 (M + H)$^+$; $^1$H NMR (400 MHz, CDCl$_3$) δ ppm 1.44 (t, J = 7.4 Hz, 3 H), 2.88 (s, 3 H), 3.11 (q, J = 7.5 Hz, 2 H), 3.28 (s, 3 H), 3.62 (s, 2 H), 4.50 (s, 2 H), 6.86 (d, J = 8.0 Hz, 1 H), 7.32 (d, J = 8.0 Hz, 1 H), 8.02 (br. s., 1 H), 8.58 (s, 1 H), 8.67 (s, 1 H). |
| 27h (Examples 19a and 27) | 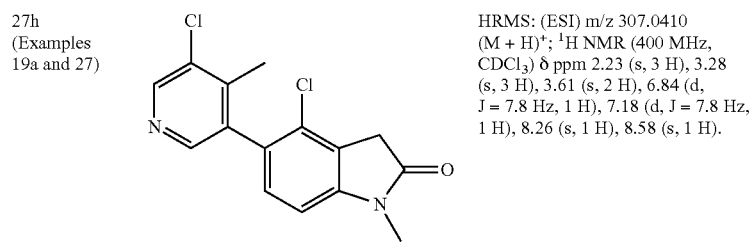<br>4-Chloro-5-(5-chloro-4-methyl-pyridin-3-yl)-1-methyl-1,3-dihydro-indol-2-one | HRMS: (ESI) m/z 307.0410 (M + H)$^+$; $^1$H NMR (400 MHz, CDCl$_3$) δ ppm 2.23 (s, 3 H), 3.28 (s, 3 H), 3.61 (s, 2 H), 6.84 (d, J = 7.8 Hz, 1 H), 7.18 (d, J = 7.8 Hz, 1 H), 8.26 (s, 1 H), 8.58 (s, 1 H). |
| 27i (Example 27) | 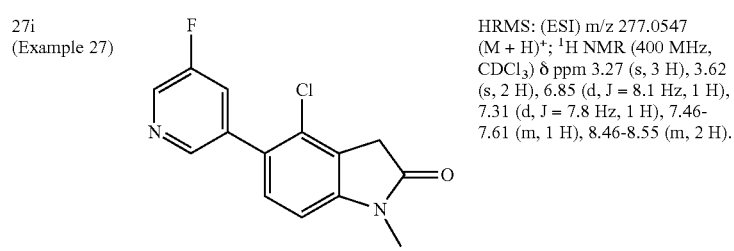<br>4-Chloro-5-(5-fluoro-pyridin-3-yl)-1-methyl-1,3-dihydro-indol-2-one | HRMS: (ESI) m/z 277.0547 (M + H)$^+$; $^1$H NMR (400 MHz, CDCl$_3$) δ ppm 3.27 (s, 3 H), 3.62 (s, 2 H), 6.85 (d, J = 8.1 Hz, 1 H), 7.31 (d, J = 7.8 Hz, 1 H), 7.46-7.61 (m, 1 H), 8.46-8.55 (m, 2 H). |

TABLE 2-continued

| Compound # (Prepared According to Example #) | Structure and Name | NMR and/or ESMS |
|---|---|---|
| 38a (Example 38) | 5-(5-Chloro-pyridin-3-yl)-4-methoxy-1-methyl-1,3-dihydro-indol-2-one | HRMS: (ESI) m/z 289.0742 (M + H)+; 1H NMR (400 MHz, DMSO-d6) d ppm 3.15 (s, 3 H), 3.81 (s, 3 H), 3.87 (s, 2 H), 6.83 (d, J = 8.1 Hz, 1 H), 7.38 (d, J = 7.8 Hz, 1 H), 7.95-7.98 (m, 1 H), 8.57 (d, J = 2.3 Hz, 1 H), 8.61 (d, J = 1.77 Hz, 1 H). |
| 38b (Example 38) | 5-(5-Fluoro-pyridin-3-yl)-4-methoxy-1-methyl-1,3-dihydro-indol-2-one | HRMS: (ESI) m/z 273.1035 (M + H)+; 1H NMR (400 MHz, DMSO-d6) δ ppm 3.14 (s, 3 H), 3.80 (s, 3 H), 3.85 (s, 2 H), 6.83 (d, 1 H), 7.37 (d, J = 8.1 Hz, 1 H), 7.78 (dt, J = 10.4, 2.8, 1.8 Hz, 1 H), 8.51 (d, J = 2.8 Hz, 1 H), 8.53 (t, J = 1.8 Hz, 1 H). |
| 38c (Examples 38 and 19a) | 5-(5-Chloro-4-methyl-pyridin-3-yl)-4-methoxy-1-methyl-1,3-dihydro-indol-2-one | HRMS: (ESI) m/z 303.0899 (M + H)+; 1H NMR (400 MHz, DMSO-d6) δ ppm 2.16 (s, 3 H), 3.15 (s, 3 H), 3.76 (s, 3 H), 3.89 (s, 2 H), 6.79 (d, J = 7.83 Hz, 1 H), 7.14 (d, J = 7.83 Hz, 1 H), 8.24 (s, 1 H), 8.55 (s, 1 H). |
| 39e (Example 39) | 1-Methyl-2-oxo-5-pyridin-3-yl-2,3-dihydro-1H-indole-7-carbonitrile | HRMS: (ESI) m/z 250.0978 (M + H)+; 1H NMR (400 MHz, (CDCl3) δ ppm 3.63 (s, 3 H), 3.65 (s, 2 H), 7.46 (dd, J = 8.0, 4.9 Hz, 1 H), 7.65 (d, J = 1.5 Hz, 1 H), 7.70 (d, J = 1.8 Hz, 1 H), 7.82-7.94 (m, 1 H), 8.66 (dd, J = 4.9, 1.4 Hz, 1 H), 8.82 (d, J = 2.3 Hz, 1 H) |
| 39f (Example 39) | 1-Methyl-2-oxo-5-pyridin-3-yl-2,3-dihydro-1H-indole-4-carbonitrile | HRMS: (ESI) m/z 250.0973 (M + H)+; 1H NMR (400 MHz, CDCl3) δ ppm 3.30 (s, 3 H), 3.79 (s, 2 H), 7.13 (d, J = 8.1 Hz, 1H), 7.48 (d, J = 8.1 Hz, 1 H), 7.50-7.54 (m, 1 H), 8.00 (d, J = 7.8 Hz, 1 H), 8.71 (d, J = 4.0 Hz, 1 H), 8.78 (d, J = 1.5 Hz, 1 H). |

TABLE 2-continued

| Compound # (Prepared According to Example #) | Structure and Name | NMR and/or ESMS |
|---|---|---|
| 40f (Example 40) | 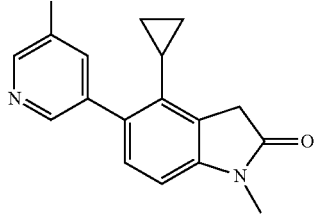<br>5-(5-Fluoro-pyridin-3-yl)-4-cyclopropyl-1-methyl-1,3-dihydro-indol-2-one | HRMS: (ESI) m/z 283.1246 (M + H)$^+$; $^1$H NMR (400 MHz, CD$_2$Cl$_2$) δ ppm 0.16-0.24 (m, 2 H), 0.72-0.81 (m, 2 H), 1.86-1.98 (m, 1 H), 3.20 (s, 3 H), 3.59 (s, 2 H), 6.80 (d, J = 8.08 Hz, 1 H), 7.21 (d, J = 8.08 Hz, 1 H), 7.44-7.51 (m, 1 H), 8.41 (d, J = 2.78 Hz, 1 H), 8.47 (t, J = 1.64 Hz, 1 H). |
| 42a (Example 42) | 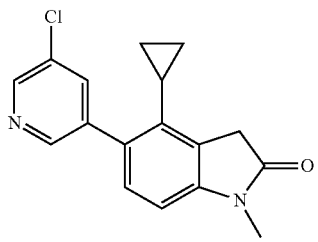<br>5-(5-Chloro-pyridin-3-yl)-4-cyclopropyl-1-methyl-1,3-dihydro-indol-2-one | HRMS: (ESI) m/z 299.0957 (M + H)$^+$; $^1$H NMR (400 MHz, CD$_2$Cl$_2$) δ ppm 0.14-0.25 (m, 2 H), 0.74-0.83 (m, 2 H), 1.85-2.00 (m, 1 H), 3.20 (s, 3 H), 3.59 (s, 2 H), 6.81 (d, J = 7.83 Hz, 1 H), 7.21 (d, J = 7.83 Hz, 1 H), 7.77 (t, J = 2.15 Hz, 1 H), 8.52 (d, J = 2.27 Hz, 1 H), 8.54 (d, J = 2.02 Hz, 1 H) |
| 45f (Example 45) | 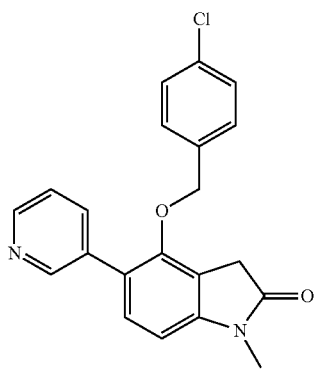 [SMILES: CN1C(=O)Cc2c1ccc(-c1cccnc1)c2OCc1ccc(Cl)cc1]<br>4-(4-Chloro-benzyloxy)-1-methyl-5-pyridin-3-yl-1,3-dihydro-indol-2-one | HRMS: (ESI) m/z 365.1055 (M + H)$^+$; $^1$H NMR (400 MHz, CD$_2$Cl$_2$) δ ppm 3.20 (s, 3 H), 3.52 (s, 2 H), 4.74 (s, 2 H), 6.73 (d, J = 8.08 Hz, 1 H), 7.06 (d, J = 8.34 Hz, 2 H), 7.24 (d, J = 8.34 Hz, 2 H), 7.31 (d, J = 7.83 Hz, 1 H), 7.39 (dd, J = 7.83, 5.05 Hz, 1 H), 7.92 (d, J = 7.83 Hz, 1 H), 8.54 (d, J = 6.32 Hz, 1 H), 8.73 (s, 1 H). |
| 45g (Example 45) | 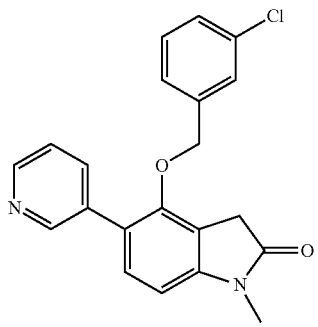 [SMILES: CN1C(=O)Cc2c1ccc(-c1cccnc1)c2OCc1cccc(Cl)c1]<br>4-(3-Chloro-benzyloxy)-1-methyl-5-pyridin-3-yl-1,3-dihydro-indol-2-one | HRMS: (ESI) m/z 365.1058 (M + H)$^+$; $^1$H NMR (400 MHz, CD$_2$Cl$_2$) δ ppm 3.20 (s, 3 H), 3.52 (s, 2 H), 4.72 (s, 2 H), 6.73 (d, J = 8.08 Hz, 1 H), 7.02 (d, J = 7.33 Hz, 1 H), 7.10 (s, 1 H), 7.18-7.34 (m, 4 H), 7.82 (d, J = 7.83 Hz, 1 H), 8.53 (d, J = 4.55 Hz, 1 H), 8.70 (s, 1 H). |

TABLE 2-continued

| Compound # (Prepared According to Example #) | Structure and Name | NMR and/or ESMS |
|---|---|---|
| 45h (Example 45) | 4-(2-Chloro-benzyloxy-1-methyl-5-pyridin-3-yl-1,3-dihydro-indol-2-one | HRMS: (ESI) m/z 365.1055 (M + H)$^+$; $^1$H NMR (400 MHz, CD$_2$Cl$_2$) δ ppm 3.20 (s, 3 H), 3.52 (s, 2 H), 4.86 (s, 2 H), 6.73 (d, J = 8.08 Hz, 1 H), 7.15-7.33 (m, 6 H), 7.85 (dt, J = 7.89, 1.99 Hz, 1 H), 8.52 (d, J = 6.06 Hz, 1 H), 8.72 (d, J = 1.77 Hz, 1 H). |
| 45i (Example 45) | 1-Methyl-5-pyridin-3-yl-4-(thiophen-2-ylmethoxy)-1,3-dihydro-indol-2-one | HRMS: (ESI) m/z 337.1010 (M + H)$^+$; $^1$H NMR (400 MHz, CD$_2$Cl$_2$) δ ppm 3.19 (s, 3 H), 3.44 (s, 2 H), 4.86 (s, 2 H), 6.72 (d, J = 7.83 Hz, 1 H), 6.79 (d, J = 3.03 Hz, 1 H), 6.90 (dd, J = 5.05, 3.54 Hz, 1 H), 7.27 (dd, J = 5.18, 1.14 Hz, 1 H), 7.30 (d, J = 7.83 Hz, 1 H), 7.37 (dd, J = 7.58, 5.31 Hz, 1 H), 7.91 (d, J = 7.83 Hz, 1 H), 8.54 (d, J = 4.29 Hz, 1 H), 8.72 (s, 1 H). |
| 45j (Example 45) | 1-Methyl-5-pyridin-3-yl-4-(thiazol-2-ylmethoxy)-1,3-dihydro-indol-2-one | HRMS: (ESI) m/z 338.0959 (M + H)$^+$; $^1$H NMR (400 MHz, CD$_2$Cl$_2$) δ ppm 3.20 (s, 3 H), 3.55 (s, 2 H), 5.06 (s, 2 H), 6.74 (d, J = 7.83 Hz, 1 H), 7.25-7.39 (m, 3 H), 7.68 (d, J = 3.28 Hz, 1 H), 7.87 (d, J = 7.83 Hz, 1 H), 8.54 (br. s., 1 H), 8.73 (br. s., 1 H). |

TABLE 2-continued

| Compound # (Prepared According to Example #) | Structure and Name | NMR and/or ESMS |
|---|---|---|
| 45k (Example 45) | 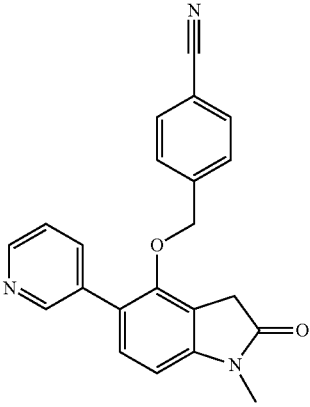 [SMILES: CN1C(=O)Cc2c1ccc(-c1cccnc1)c2OCc1ccc(C#N)cc1]<br>4-(1-Methyl-2-oxo-5-pyridin-3-yl-2,3-dihydro-1H-indol-4-yloxymethyl)-benzonitrile | HRMS: (ESI) m/z 356.1400 (M + H)$^+$; $^1$H NMR (400 MHz, CD$_2$Cl$_2$) δ ppm 3.20 (s, 3 H), 3.53 (s, 2 H), 4.81 (s, 2 H), 6.73 (d, J = 8.08 Hz, 1 H), 7.25 (d, J = 8.59 Hz, 2 H), 7.27-7.33 (m, 2 H), 7.57 (d, J = 8.34 Hz, 2 H), 7.80 (d, J = 8.34 Hz, 1 H), 8.52 (dd, J = 4.80, 1.52 Hz, 1 H), 8.71 (d, J = 1.52 Hz, 1 H). |
| 45l (Example 45) | 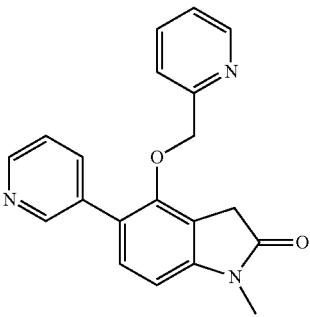<br>1-Methyl-5-pyridin-3-yl-4-(pyridin-2-ylmethoxy)-1,3-dihydro-indol-2-one | HRMS: (ESI) m/z 332.1396 (M + H)$^+$; $^1$H NMR (400 MHz, DMSO-d$_6$) δ ppm 3.16 (s, 3 H), 3.79 (s, 2 H), 5.06 (s, 2 H), 6.88 (d, J = 7.83 Hz, 1 H), 7.26-7.33 (m, 2 H), 7.35 (d, J = 8.08 Hz, 1 H), 7.40 (dd, J = 7.58, 4.55 Hz, 1 H), 7.75 (td, J = 7.71, 1.77 Hz, 1 H), 7.89 (dt, J = 7.83, 2.02 Hz, 1 H), 8.46-8.53 (m, 2 H), 8.67 (d, J = 2.27 Hz, 1 H). |
| 45m (Example 45) | 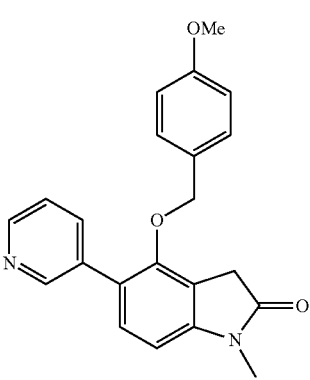 [SMILES: COc1ccc(COc2c(-c3cccnc3)ccc3c2CC(=O)N3C)cc1]<br>4-(4-Methoxy-benzyloxy)-1-methyl-5-pyridin-3-yl-1,3-dihydro-indol-2-one | HRMS: (ESI) m/z 361.1540 (M + H)$^+$; $^1$H NMR (400 MHz, CD$_2$Cl$_2$) δ ppm 3.19 (s, 3H), 3.46 (s, 2 H), 3.77 (s, 3 H), 4.64 (s, 2 H), 6.70 (d, J = 8.08 Hz, 1 H), 6.78 (d, J = 8.59 Hz, 2 H), 7.02 (d, J = 8.84 Hz, 2 H), 7.24-7.36 (m, 2 H), 7.84 (dt, J = 7.83, 1.89 Hz, 1 H), 8.53 (d, J = 6.57 Hz, 1 H), 8.72 (d, J = 1.52 Hz, 1 H). |

TABLE 2-continued

| Compound # (Prepared According to Example #) | Structure and Name | NMR and/or ESMS |
|---|---|---|
| 45n (Example 45) | 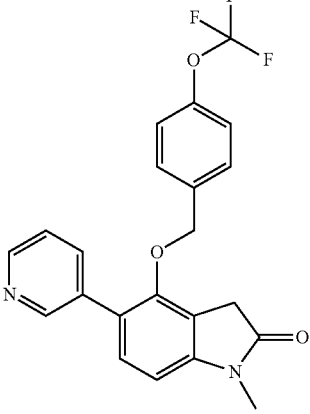\n\n1-Methyl-5-pyridin-3-yl-4-(4-trifluoromethoxy-benzyloxy)-1,3-dihydro-indol-2-one | HRMS: (ESI) m/z 415.1268 (M + H)$^+$; $^1$H NMR (400 MHz, CD$_2$Cl$_2$) δ ppm 3.20 (s, 3 H), 3.53 (s, 2 H), 4.74 (s, 2 H), 6.73 (d, J = 7.83 Hz, 1 H), 7.04-7.22 (m, 4 H), 7.25-7.40 (m, 2 H), 7.80 (dt, J = 7.83, 1.89 Hz, 1 H), 8.53 (d, J = 6.32 Hz, 1 H), 8.72 (s, 1 H). |
| 45o (Example 45) | 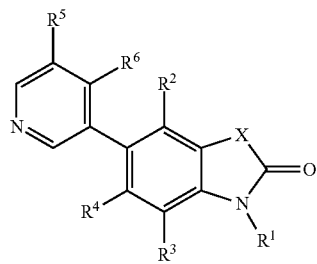\n\n4-(Methoxy-d3)-1-methyl-5-pyridin-3-yl-1,3-dihydro-indol-2-one | HRMS: (ESI) m/z 258.1319 (M + H)$^+$; $^1$H NMR (400 MHz, DMSO-d$_6$) δ ppm 3.14 (s, 3 H), 3.84 (s, 2 H), 6.82 (d, J = 8.08 Hz, 1 H), 7.30 (d, J = 8.08 Hz, 1 H), 7.43 (dd, J = 7.83, 4.80 Hz, 1 H), 7.84 (dt, J = 7.96, 2.02, 1.89 Hz, 1 H), 8.51 (dd, J = 4.80, 1.77 Hz, 1 H), 8.63 (d, J = 3.03 Hz, 1 H). |

It can be seen that the compounds of the invention are useful as inhibitors of aldosterone Synthase activity and therefore useful in the treatment of diseases and conditions mediated by Aldosterone synthase such as the metabolic disorders disclosed herein.

It will be understood that the invention has been described by way of example only and modifications may be made whilst remaining within the scope and spirit of the invention.

The invention claimed is:
1. A compound of Formula I:

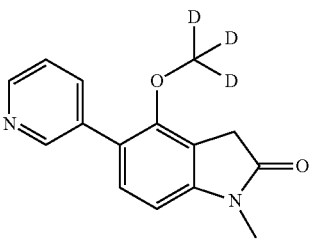 [SMILES: [2H]C([2H])([2H])Oc1c(-c2cccnc2)ccc2c1CC(=O)N2C]

(I)

a pharmaceutically acceptable salt thereof, wherein:
X is CH$_2$;
each R$^1$ are independently C$_{1-7}$alkyl or C$_{3-8}$cycloalkyl;
each of R$^2$ and R$^6$ are independently hydrogen, halogen, cyano, hydroxy-C$_{1-7}$alkyl, —OR$^7$, C$_{3-8}$cycloalkyl, halo-C$_{1-7}$alkyl or —CH$_2$—NR$^8$—SO$_2$—R$^{10}$;
R$^3$ and R$^4$ are independently hydrogen, halogen or cyano;
R$^5$ is C$_{1-7}$alkyl, cyano, hydroxy, hydroxy-C$_{1-7}$alkyl, hydroxy-C$_{3-8}$cycloalkylalkyl, C$_{1-7}$alkoxy-C$_{3-8}$alkyl, C$_{6-10}$aryl, C$_{3-8}$cycloalkyl, halo-C$_{1-7}$alkyl, —NR$^8$R$^9$, —CH$_2$—NR$^8$—C(O)NR$^8$R$^9$, —CH$_2$—NR$^8$—SO$_2$—R$^{10}$, —C(O)—R$^{10}$, —SO$_2$R$^{10}$, —C(O)—NR$^8$R$^9$, —SO$_2$—NR$^8$R$^9$, —NR$^8$C(O)—R$^{10}$, —CH$_2$CN, or —NR$^8$—SO$_2$—R$^{10}$;
R$^7$ is C$_{1-7}$alkyl, C$_{3-8}$cycloalkyl-C$_{1-7}$alkyl, C$_{6-10}$aryl-C$_{1-7}$alkyl, or —C(O)—R$^{10}$; in which C$_{6-10}$aryl, C$_{1-7}$alkyl and C$_{3-8}$cycloalkyl are optionally substituted with C$_{1-7}$alkoxy, halo, halo-C$_{3-8}$alkoxy, C$_{1-7}$alkyl, OH or halo-C$_{1-7}$alkyl;
each of R$^8$, R$^9$ are independently hydrogen, C$_{1-7}$alkyl, halo-C$_{1-7}$alkyl, or C$_{6-10}$aryl-C$_{1-7}$alkyl;
R$^{10}$ is hydrogen, C$_{1-7}$alkyl, halo-C$_{1-7}$alkyl, C$_{6-10}$aryl-C$_{1-7}$alkyl, or —NR$^8$R$^9$;
or a pharmaceutically acceptable salt thereof.
2. The compound according to claim 1, wherein:
X is CH$_2$;
each R$^1$ are independently C$_{1-7}$alkyl or C$_{3-8}$cycloalkyl;
each of R$^2$ and R$^6$ are independently hydrogen, halogen, cyano, C$_{1-7}$alkyl, hydroxy-C$_{1-7}$alkyl, —OR$^7$, C$_{3-8}$cycloalkyl, halo-C$_{1-7}$alkyl or —CH$_2$—NR$^8$—SO$_2$—R$^{10}$;

$R^3$ and $R^4$ are independently hydrogen, halogen or cyano;

$R^5$ is $C_{1-7}$alkyl, cyano, hydroxy, hydroxy-$C_{1-7}$alkyl, hydroxy-$C_{3-8}$cycloalkylalkyl, $C_{1-7}$alkoxy-$C_{3-8}$alkyl, $C_{6-10}$aryl, $C_{3-8}$cycloalkyl, halo-$C_{1-7}$alkyl, —$NR^8R^9$, —$CH_2$—$NR^8$—$C(O)NR^8R^9$, —$CH_2$—$NR^8$—$SO_2$—$R^{10}$, —$C(O)$—$R^{10}$, —$SO_2R^{10}$, —$C(O)$—$NR^8R^9$, —$SO_2$—$NR^8R^9$, —$NR^8C(O)$—$R^{10}$, —$CH_2CN$, or —$NR^8$—$SO_2$—$R^{10}$;

$R^7$ is $C_{1-7}$alkyl, $C_{3-8}$cycloalkyl-$C_{1-7}$alkyl, $C_{6-10}$aryl-$C_{1-7}$alkyl, or —$C(O)$—$R^{10}$; in which $C_{6-10}$aryl, $C_{1-7}$alkyl, and $C_{3-8}$cycloalkyl are optionally substituted with $C_{1-7}$alkoxy, halo, halo-$C_{3-8}$alkoxy, $C_{1-7}$alkyl, OH or halo-$C_{1-7}$alkyl;

each of $R^8$, $R^9$ are independently hydrogen, $C_{1-7}$alkyl, halo-$C_{1-7}$alkyl, or $C_{6-10}$aryl-$C_{1-7}$alkyl;

$R^{10}$ is hydrogen, $C_{1-7}$alkyl, halo-$C_{1-7}$alkyl, $C_{6-10}$aryl-$C_{1-7}$alkyl, or —$NR^8R^9$ or a pharmaceutically acceptable salt thereof.

3. The compound according to claim 1, wherein:
$R^5$ is $C_{1-7}$alkyl, cyano, hydroxy, hydroxy-$C_{1-7}$alkyl, hydroxy-$C_{3-8}$cycloalkylalkyl, $C_{1-7}$alkoxy-$C_{3-8}$alkyl, $C_{6-10}$aryl, $C_{3-8}$cycloalkyl, halo-$C_{1-7}$alkyl, —$NR^8R^9$, —$CH_2$—$NR^8$—$C(O)NR^8R^9$, —$CH_2$—$NR^8$—$SO_2$—$R^{10}$, —$C(O)$—$R^{10}$, —$SO_2R^{10}$, —$C(O)$—$NR^8R^9$, —$SO_2$—$NR^8R^9$, —$NR^8C(O)$—$R^{10}$, —$CH_2CN$, or —$NR^8$—$SO_2$—$R^{10}$, or pharmaceutically acceptable salt thereof.

4. The compound according to claim 1, wherein:
$R^1$ is methyl;
$R^2$ is hydrogen, halogen, —$OR^7$ or $C_{1-7}$alkyl;
$R^3$ and $R^4$ are hydrogen;
$R^5$ is $C_{1-7}$alkyl, hydroxy, hydroxy-$C_{1-7}$alkyl, benzyloxy, $C_{6-10}$aryl, $C_{3-8}$cycloalkyl, —$CH_2NR^8SO_2R^{10}$, —$SO_2NR^8R^{10}$, or —$NR^8R^9$;
$R^6$ is hydrogen or $C_{1-7}$alkyl;
$R^7$ is $C_{1-7}$alkyl, or $C_{6-10}$aryl-$C_{1-7}$alkyl; and
each of $R^8$, $R^9$ and $R^{10}$ are independently $C_{1-7}$alkyl or H, or a pharmaceutically acceptable salt thereof.

5. The compound according to claim 1, wherein:
$R^1$ is methyl; and
$R^2$ is hydrogen, chloro, methyl, methoxy or —O-benzyl, or a pharmaceutically acceptable salt thereof.

6. The compound according to claim 1, wherein $R^2$ is chloro, or a pharmaceutically acceptable salt thereof.

7. The compound according to claim 1, wherein $R^2$ is —$OR^7$, wherein $R^7$ is selected from the group consisting of:

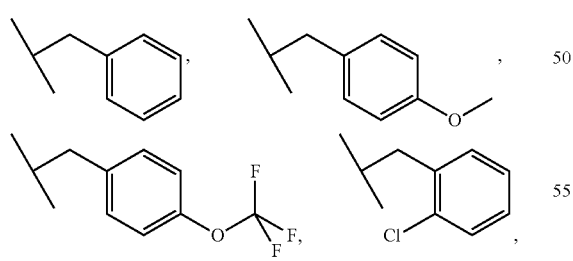

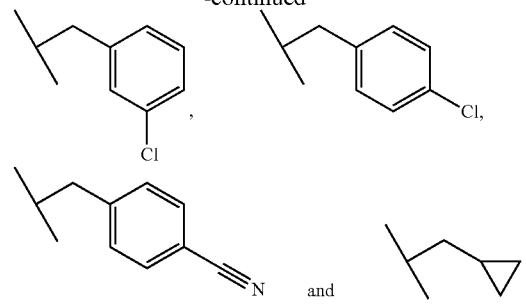

or a pharmaceutically acceptable salt thereof.

8. The compound according to claim 1, wherein $R^5$ is selected from the group consisting of:

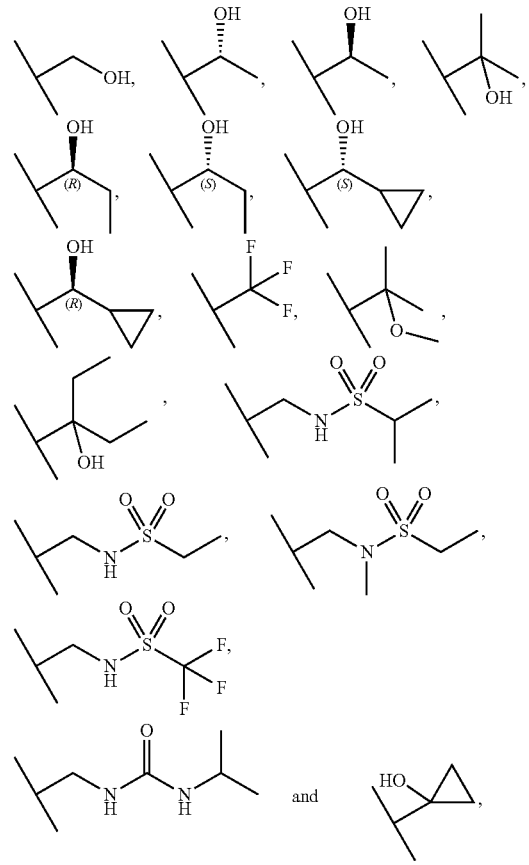

or a pharmaceutically acceptable salt thereof.

9. A pharmaceutical composition comprising a therapeutically effective amount of the compound according to claim 1 and one or more pharmaceutically acceptable carriers.

* * * * *